(12) United States Patent
Castillo et al.

(10) Patent No.: US 10,507,248 B2
(45) Date of Patent: **\*Dec. 17, 2019**

(54) HYDROPHOBIC CORE CARRIER COMPOSITIONS FOR DELIVERY OF THERAPEUTIC AGENTS, METHODS OF MAKING AND USING THE SAME

(71) Applicant: PharmaIn Corporation, Bothell, WA (US)

(72) Inventors: Gerardo M. Castillo, Bothell, WA (US); Elijah M. Bolotin, Bothell, WA (US)

(73) Assignee: PharmaIN Corporation, Bothell, WA (US)

( * ) Notice: Subject to any disclaimer, the term of this patent is extended or adjusted under 35 U.S.C. 154(b) by 126 days.

This patent is subject to a terminal disclaimer.

(21) Appl. No.: 15/672,802

(22) Filed: Aug. 9, 2017

(65) Prior Publication Data

US 2017/0368190 A1 Dec. 28, 2017

Related U.S. Application Data

(63) Continuation of application No. 14/087,523, filed on Nov. 22, 2013, now Pat. No. 9,737,615, which is a
(Continued)

(51) Int. Cl.
*A61K 38/00* (2006.01)
*A61K 38/18* (2006.01)
(Continued)

(52) U.S. Cl.
CPC ...... *A61K 47/6907* (2017.08); *A61K 31/4439* (2013.01); *A61K 38/1808* (2013.01);
(Continued)

(58) Field of Classification Search
None
See application file for complete search history.

(56) References Cited

U.S. PATENT DOCUMENTS 4,857,311 A   8/1989 Domb et al.
5,118,666 A   6/1992 Habener
(Continued)

FOREIGN PATENT DOCUMENTS

EP    0381446 B1    8/1994
JP    2002-194080 A    7/2002
(Continued)

OTHER PUBLICATIONS

Final Official Action dated Mar. 12, 2015, issued in corresponding Japanese Application No. 2013-094413, filed Dec. 19, 2006, 6 pages.
(Continued)

*Primary Examiner* — Kevin S Orwig
(74) *Attorney, Agent, or Firm* — Christensen O'Connor Johnson Kindness PLLC

(57) ABSTRACT

The present invention relates, in part, to a biocompatible hydrophobic-core carrier comprising a carrier, and a plurality of hydrophobic groups covalently linked to the polymeric carrier. The hydrophobic groups are capable of dissociably linking load molecules such as therapeutic agents. The hydrophobic-core carrier may also comprise protective side chains, orienting molecules, and targeting molecules.

32 Claims, 49 Drawing Sheets

Related U.S. Application Data continuation of application No. 11/613,183, filed on Dec. 19, 2006, now abandoned.

(60) Provisional application No. 60/813,629, filed on Dec. 19, 2005.

(51) Int. Cl.

| | | |
|---|---|---|
| A61K 47/30 | (2006.01) | |
| A61K 47/69 | (2017.01) | |
| A61K 47/64 | (2017.01) | |
| A61K 38/22 | (2006.01) | |
| A61K 38/26 | (2006.01) | |
| A61K 31/4439 | (2006.01) | |
| A61K 47/60 | (2017.01) | |

(52) U.S. Cl.
CPC ...... *A61K 38/1841* (2013.01); *A61K 38/2207* (2013.01); *A61K 38/26* (2013.01); *A61K 47/60* (2017.08); *A61K 47/645* (2017.08)

(56) References Cited

U.S. PATENT DOCUMENTS

| | | |
|---|---|---|
| 5,120,712 A | 6/1992 | Habener |
| 5,527,524 A | 6/1996 | Tomalia et al. |
| 5,554,388 A | 9/1996 | Illum |
| 5,593,658 A | 1/1997 | Bogdanov et al. |
| 5,605,672 A | 2/1997 | Bogdanov et al. |
| 5,614,492 A | 3/1997 | Habener |
| 5,631,018 A | 5/1997 | Zalipsky et al. |
| 5,661,025 A | 8/1997 | Szoka, Jr. et al. |
| 5,663,387 A | 9/1997 | Singh |
| 5,681,544 A | 10/1997 | Schmitt-Willich et al. |
| 5,681,811 A | 10/1997 | Ekwuribe |
| 5,714,166 A | 2/1998 | Tomalia et al. |
| 5,744,166 A | 4/1998 | Illum |
| 5,763,585 A | 6/1998 | Nag |
| 5,837,747 A | 11/1998 | Soon-Shiong et al. |
| 5,871,710 A | 2/1999 | Bogdanov et al. |
| 5,891,418 A | 4/1999 | Sharma |
| 5,958,909 A | 9/1999 | Habener |
| 5,977,084 A | 11/1999 | Szoka, Jr. et al. |
| 6,006,753 A | 12/1999 | Efendic |
| 6,051,549 A | 4/2000 | Roberts et al. |
| 6,113,946 A | 9/2000 | Szoka, Jr. et al. |
| 6,124,273 A | 9/2000 | Drohan et al. |
| 6,162,462 A | 12/2000 | Bolotin et al. |
| 6,274,175 B1 | 8/2001 | Gombotz et al. |
| 6,284,727 B1 | 9/2001 | Kim et al. |
| 6,338,859 B1 | 1/2002 | Leroux et al. |
| 6,348,069 B1 | 2/2002 | Vacanti et al. |
| 6,365,173 B1 | 4/2002 | Domb et al. |
| 6,395,299 B1 | 5/2002 | Babich et al. |
| 6,443,898 B1 | 9/2002 | Unger et al. |
| 6,447,753 B2 | 9/2002 | Edwards et al. |
| 6,458,373 B1 | 10/2002 | Lambert et al. |
| 6,468,532 B1 | 10/2002 | Hsei et al. |
| 6,492,560 B2 | 12/2002 | Wilbur et al. |
| 6,509,323 B1 | 1/2003 | Davis et al. |
| 6,521,736 B2 | 2/2003 | Watterson et al. |
| 6,576,254 B1 | 6/2003 | Uchegbu |
| 6,579,851 B2 | 6/2003 | Goeke et al. |
| 6,583,111 B1 | 6/2003 | DiMarchi et al. |
| 6,586,524 B2 | 7/2003 | Sagara et al. |
| 6,589,549 B2 | 7/2003 | Shih et al. |
| 6,627,228 B1 | 9/2003 | Milstein et al. |
| 6,703,037 B1 | 3/2004 | Hubbell et al. |
| 6,703,359 B1 | 3/2004 | Young et al. |
| 6,706,689 B2 | 3/2004 | Coolidge et al. |
| 6,747,006 B2 | 6/2004 | Efendic |
| 6,828,303 B2 | 12/2004 | Kim et al. |
| 6,849,708 B1 | 2/2005 | Habener |
| 6,894,024 B2 | 5/2005 | Coolidge et al. |
| 6,899,883 B2 | 5/2005 | Dupre |
| 6,982,248 B2 | 1/2006 | Coolidge et al. |
| 6,992,060 B2 | 1/2006 | Brand |
| 6,998,137 B2 | 2/2006 | Shih et al. |
| 7,101,843 B2 | 9/2006 | Glaesner et al. |
| 7,138,105 B2 | 11/2006 | Bolotin |
| 7,138,486 B2 | 11/2006 | Habener |
| 7,144,863 B2 | 12/2006 | DeFelippis et al. |
| 7,199,217 B2 | 4/2007 | DiMarchi et al. |
| 7,259,233 B2 | 8/2007 | Dodd et al. |
| 7,521,527 B2 | 4/2009 | Dong et al. |
| 7,534,449 B2 | 5/2009 | Saltzman et al. |
| 7,589,169 B2 | 9/2009 | Bolotin |
| 7,632,806 B2 | 12/2009 | Juul-Mortensen et al. |
| 7,635,463 B2 | 12/2009 | Bolotin et al. |
| 7,790,140 B2 | 9/2010 | Bolotin |
| 7,790,681 B2 | 9/2010 | Hathaway et al. |
| 7,807,780 B2 | 10/2010 | Waugh et al. |
| 7,875,700 B2 | 1/2011 | Radhakrishnan et al. |
| 7,960,336 B2 | 6/2011 | Castillo et al. |
| 7,981,444 B2 | 7/2011 | Tomalla et al. |
| 7,985,424 B2 | 7/2011 | Tomalla et al. |
| 8,008,255 B2 | 8/2011 | Ong et al. |
| 8,092,788 B2 | 1/2012 | Dake et al. |
| 8,231,859 B2 | 7/2012 | Bolotin et al. |
| 8,257,682 B2 | 9/2012 | Bolotin et al. |
| 8,277,776 B2 | 10/2012 | Bolotin et al. |
| 8,563,527 B2 | 10/2013 | Castillo et al. |
| 8,999,930 B2 | 4/2015 | Castillo et al. |
| 9,089,636 B2 | 7/2015 | Gonnelli |
| 2003/0119734 A1 | 6/2003 | Flink et al. |
| 2003/0220251 A1 | 11/2003 | Knudsen et al. |
| 2004/0092432 A1 | 5/2004 | During et al. |
| 2004/0162241 A1 | 8/2004 | Efendic |
| 2004/0197369 A1 | 10/2004 | Hubbell et al. |
| 2004/0209803 A1 | 10/2004 | Baron et al. |
| 2004/0220105 A1 | 11/2004 | Jensen et al. |
| 2004/0235726 A1 | 11/2004 | Jakubowski et al. |
| 2005/0008661 A1 | 1/2005 | Fereira et al. |
| 2005/0014681 A1 | 1/2005 | Minamitake et al. |
| 2005/0143303 A1 | 6/2005 | Quay et al. |
| 2005/0148497 A1 | 7/2005 | Khan et al. |
| 2005/0215475 A1 | 9/2005 | Ong et al. |
| 2005/0260259 A1 | 11/2005 | Bolotin |
| 2006/0003935 A1 | 1/2006 | Pan et al. |
| 2006/0057137 A1 | 3/2006 | Steiness |
| 2006/0128627 A1 | 6/2006 | Goke et al. |
| 2006/0183682 A1 | 8/2006 | Juul-Mortensen |
| 2006/0199763 A1 | 9/2006 | Knudsen et al. |
| 2006/0233857 A1 | 10/2006 | Amsden et al. |
| 2006/0247167 A1 | 11/2006 | Schlein et al. |
| 2006/0286129 A1 | 12/2006 | Sarubbi |
| 2007/0041951 A1 | 2/2007 | Egan et al. |
| 2007/0141006 A1 | 6/2007 | Livoreil et al. |
| 2007/0141145 A1 | 6/2007 | Castillo et al. |
| 2009/0176892 A1 | 7/2009 | Castillo et al. |

FOREIGN PATENT DOCUMENTS

| | | |
|---|---|---|
| JP | 2005-524657 A | 8/2005 |
| WO | 97/33552 A1 | 9/1997 |
| WO | 98/42383 A1 | 10/1998 |
| WO | 03/072143 A1 | 9/2003 |
| WO | 2004/022004 A2 | 3/2004 |
| WO | 2004/026912 A1 | 4/2004 |
| WO | 2004/022004 A3 | 12/2004 |
| WO | 2005/065714 A1 | 7/2005 |
| WO | 2005/084180 A2 | 9/2005 |
| WO | 2005/084180 A3 | 12/2005 |
| WO | 2005/115492 A1 | 12/2005 |
| WO | 2007/024899 A2 | 3/2007 |
| WO | 2007/030706 A1 | 3/2007 |
| WO | 2007/038964 A1 | 4/2007 |
| WO | 2007/048190 A1 | 5/2007 |
| WO | 2007/056681 A2 | 5/2007 |
| WO | 2007/076371 A2 | 7/2007 |
| WO | 2007/082331 A1 | 7/2007 |

(56) References Cited

FOREIGN PATENT DOCUMENTS

| | | |
|---|---|---|
| WO | 2007/024899 A3 | 11/2007 |
| WO | 2007/056681 A3 | 4/2008 |

OTHER PUBLICATIONS

Official Action dated Mar. 12, 2015, issued in corresponding Japanese Application No. 2014-082502, filed Dec. 19, 2006, 3 pages.
Ahren et al. "Improved glucose tolerance and insulin secretion by inhibition of dipeptidyl peptidase IV in mice." Eur. J. Pharmacol. 2000; 404(1-2): 239-245.
Berklow et al. Eds. The Merck Manual of Diagnosis and Therapy. Merck Laboratories. Merck & Co. Inc. Rahway, NJ. 1992.
Brand et al. "Pharmacological treatment of chronic diabetes by stimulating pancreatic beta-cell regeneration with systemic co-administration of EGF and gastrin." Pharmacol Toxicol. 2002; 91(6): 414-420.
Bulotta et al. "Cultured pancreatic ductal cells undergo cell cycle re-distribution and beta-cell-like differentiation in response to glucagon-like peptide-1." J. Mol. Endocrinol. 2002; 29(3): 347-360.
Buteau et al. "Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells." Diabetologia. 1999; 42(7): 856-864.
Cadranel et al. [Long-term efficacy and tolerability of omeprazole in 20 patients with severe Zollinger-Ellison syndrome] Gastroenterol Clin. Biol. 1989; 13(8-9): 654-662. (French with English Summary).
Caliceti et al. "Pharmacokinetic and biodistribution properties of poly(ethylene glycol)-protein conjugates." Advanced Drug Delivery Reviews. 2003; 55: 1261-1277.
Castillo et al. "Long-acting GLP-1: formulation and in vitro evaluation." Diabetes. Jun. 2007; Supplement 1, vol. 56, p. A127.
Castillo et al. "PGC-GLP-1: Pharmacokinetics in rodents." Diabetes. Jun. 2007; Supplement 1, vol. 56, p. A554.
Chen et al. "A novel gene delivery system using EGF receptor-mediated endocytosis." FEBS Lett. 1994; 338(2): 167-9.
Chowdhury et al. "Fate of DNA targeted to the liver by asialoglycoprotein receptor-mediated endocytosis in vivo. Prolonged persistence in cytoplasmic vesicles after partial hepatectomy" J Biol Chem. 1993; 268(15): 11265-71.
Cras-Meneur et al. "Epidermal growth factor increases undifferentiated pancreatic embryonic cells in vitro: a balance between proliferation and differentiation." Diabetes 2001; 50(7): 1571-1579.
Crutzfeldt et al. "Is Hypergastrinaemia dangerous to man?" Scan J Gastroenterol Suppl. 1991; 180: 179-191.
Dash et al. "Synthetic polymers for vectorial delivery of DNA: characterisation of polymer-DNA complexes by photon correlation spectroscopy and stability to nuclease degradation and disruption by polyanions in vitro." Journal of Controlled Release. 1997; 48: 269-276.
Druncker. "Enhancing incretin action for the treatment of type 2 diabetes." Diabetes Care. 2003; 26(10): 2929-2940.
Erbacher et al. "The reduction of the positive charges of polylysine by partial gluconoylation increases the transfection efficiency of polylysine/DNA complexes." Biochim Biophys Acta. 1997; 1324(1): 27-36.
Ettaro et al. "Cost-of-illness studies in diabetes mellitus." Pharmacoeconomics. 2004; 22(3): 149-64.
European search report and opinion dated Apr. 24, 2013 for EP Application No. 09700547.4.
Feng et al. "Tissue distribution and plasma clearance of heparin-binding EGF-like growth factor (HB-EGF) in adult and newborn rats." Peptides. 2006; 27: 1589-1596.
Gilles et al. "Stability of water-soluble carbodiimides in aqueous solution." Analy Biochem. 1990; 184(2): 244-8.

Hakanson et al. "Evidence that gastrin enhances 45Ca uptake into bone through release of a gastric hormone." Regul Pept. 1990; 28(1): 107-118.
Halter et al. "Effect of acid inhibition on the growth of parietal cells." Scand J Gastroenterol Suppl. 1986; 125: 9-13.
Hansen et al. "Pharmcokinetics and organ metabolism of carboxyamidated and glycine-extended gastrins in pigs." Am J Physiol. 1996; 271: G156-163.
Hrkach et al. "Poly(L-lactic acid-co-amino acid) Graft Copolymers: A Class of Functional Biodegradable Biomaterials. Hydrogel and Biodegradable Polymers for Bioapplications." Acs. Symposium Series No. 627. Ottenbrite, et al. Eds. American Chemical Society. Chapter 8. 1996; 93-101.
Hrkach et al. "Synthesis of poy(L-lactic acid-co-L-lysine) graft copolymers." Macromolecules. 1995; 28: 4736-9.
Hudecz et al. "Influence of carrier on biodistribution and in vitro cytotoxicity of methotrexate-branched polypeptide conjugates." Bioconjug Chem. 1993; 4(1): 25-33.
Huotari et al. "Growth factor-mediated proliferation and differentiation of insulin-producing INS-1 and RINm5F cells: identification of betacellulin as a novel beta-cell mitogen." Endocrinology. 1998; 139(4): 1494-1499.
Im et al. "Irreversible inactivation of rat gastric (H+-K+)-ATPase in vivo by omeprazole." Biochem Biophys Res Commun. 1985; 126(1): 78-82.
International search report dated Nov. 23, 2007 for PCT Application No. PCT/US2006/062328.
International search report dated Feb. 24, 2009 for PCT Application No. PCT/US2009/030678.
International search report dated Feb. 26, 2009 for PCT Application No. PCT/US2009/030471.
International Search Report for PCT/US03/05937 completed on Jun. 16, 2003 and dated Jul. 24, 2003 (4 pages).
Keeling et al. "Studies on the mechanism of action of omeprazole." Biochem Pharmacol. 1985; 34(16): 2967-2973.
Kilnkenberg-Knol. "The role of omeprazole in healing and prevention of reflux disease." Hepatogastroenterology. 1992; 39: 27-30.
Kollen et al. "Gluconoylated and glycosylated polylysines as vectors for gene transfer into cystic fibrosis airway epithelial cells." Hum Gene Ther. 1996; 7(13): 1577-86.
Koop et al. "Serum gastrin levels during long-term omeprazole treatment." Aliment Pharmacol Ther. 1990; 4(2): 131-138.
Krakowski et al. "Transgenic expression of epidermal growth factor and keratinocyte growth factor in beta-cells results in substantial morphological changes" J Endocrinol. 1999; 162: 167-175.
Lamberts et al. "Long-term omeprazole treatment in man: effects on gastric endocrine cell populations." Digestion. 1988; 39(2): 126-135.
Lapidot et al. "Use of esters of N-hydroxysuccinimide in the synthesis of N-acylamino acids." J Lipid Res. 1967; 8(2): 142-145.
Larson et al. "Omeprazole-induced hypergastrinemia: role of gastric acidity." J Surg Res. 1986; 40(5): 504-509.
Larson et al. "Relationship of omeprazole-induced hypergastrinemia to gastric pH." Surgery. 1986; 100(2): 175-180.
Lev-Ran et al. "Origin of urinary epidermal growth factor in humans: excretion of endogenous EGF and infused [131I]-human EGF and kidney histochemistry." Clin Exp Pharmacol Physiol. 1992; 19(10): 667-673.
Medarova et al. "Noninvasive magnetic resonance imaging of microvascular changes in type 1 diabetes." Diabetes. Aug. 2007; 56(11):2677-2682.
Nielsen et al. "Pharmacology of exenatide (synthetic exendin-4) for the treatment of type 2 diabetes." Curr. Opinion Investig. Drugs. 2003; 4(4): 401-405.
Otto et al. "Recognition and separation of isoenzymes by metal chelates: Immobilized metal ion affinity partitioning of lactate dehydrogenase isoenzymes." Journal of Chromatography. 1993; 644: 25-33.
Perry et al. "The glucagon-like peptides: a double-edged therapeutic sword?" Trends in Pharmacol. Sci. 2003; 24(7): 377-383.

(56) References Cited

OTHER PUBLICATIONS

PharmaIn—Enabling and improving human therapeutics. PharmaIn Introduction. Oct. 2009. Available at http://www.pharmain.com/PDF/PharmaIN%20BD%20Presentation%20Slides_16OCT09.pdf. Accessed Mar. 24, 2010.

Porath et al. "Metal chelate affinity chromatography, a new approach to protein fractionation." Nature. Dec. 18, 1975; 258(5536): 598-9.

Reichstetter et al. "Long acting GLP-1 for the treatment of type 1 diabetes." Diabetes. Jun. 2007; Supplement 1, vol. 56, p. A73.

Reichstetter et al. "Long acting GLP-1 for the treatment of type 2 diabetes." Diabetes. Jun. 2007; Supplemental 1, vol. 56, p. A144.

Schentag et al. "Pharmacokinetics and pharmacodynamics of acid-suppressive agents in patients with gastroesophageal reflux disease." Am J Hosp Pharm. 1993; 50: S7-10.

Scrocchi et al. "Identification of glucagon-like peptide 1 (GLP-1) actions essential for glucose homeostasis in mice with disruption of GLP-1 receptor signaling." Diabetes. 1998; 47(4): 632-639.

Senekowitsch-Schmidtke et al. "In vivo evaluation of epidermal growth factor (EGF) receptor density on human tumor xenografts using radiolabeled EGF and anti-(EGF receptor) mAb 425." Cancer Immunol Immunother. 1996; 42(2): 108-114.

Shapiro et al. "Clinical islet transplant: current and future directions towards tolerance." Immunol. Rev. 2003; 196: 219-36.

Sifton. Physician Desk Reference. Medical Economics Company, Inc. Montvale, NJ. 2001.

Song et al. "Expansion of Pdx1-expressing pancreatic epithelium and islet neogenesis in transgenic mice overexpression transforming growth factor alpha." Gastroenterology. 1999; 117(6): 1416-1426.

Sparado et al. "A convenient manual trinitrobenzenesulfonic acid method for monitoring amino acids and peptides in chromatographic column effluents." Analy Biochem. 1979; 96: 317-321.

Suarez-Pinzon et al. "Combination therapy with epidermal growth factors and gastrin increases beta-cells mass and reverses hyperglycemia in diabetic NOD mice." Diabetes. 2005; 54(9): 2596-2601.

Suginoshita et al. "Liver targeting of interferon-$\beta$ with a liver-affinity polysaccharide based on metal coordination in mice" Journal of Pharmacology and Experimental Therapeutics. 2001; 298(2): 805-11.

Terpe. "Overview of tag protein fusions: from molecular and biochemical fundamentals to commercial systems." Appl. Microbiol Biotechnol. 2003; 60: 523-33.

Urusova et al. "GLP-1 inhibition of pancreatic islet cell apoptosis." Trends Endocrinol Metab. 2004; 15(1): 27-33.

Van Nieuwenhove et al. "Gastrin stimulates epithelial cell proliferation in the esophagus of rats." Virchows Arch. 1998; 432(4): 371-375.

Wagner. "Delivery of drugs, protein and genes into cells using transferrin as a ligand for receptor-mediated endocytosis." Advanced drug delivery reviews. 1994; 14: 113-135.

Wang et al. "Pancreatic gastrin stimulates islet differentiation of transforming growth factor alpha-induced ductular precursor cells." J Clin Invest. 1993; 92(3): 1349-1356.

Wiedeman et al. "Dipeptidyl peptidase IV inhibitors for the treatment of impaired glucose tolerance and type 2 diabetes." Curr. Opinion Investig. Drugs. 2003; 4(4): 412-420.

Xu et al. "Exendin-4 stimulates both beta-cell replication and neogenesis, resulting in increased beta-cell mass and improved glucose tolerance in diabetic rats" Diabetes. 1999; 48(12): 2270-2276.

Yamamoto et al. "Recombinant human betacellulin promotes the neogenesis of beta-cells and ameliorates glucose intolerance in mice with diabetes induced by selective alloxan perfusion." Diabetes. 2000; 49(12): 2021-2027.

Yu et al. "Pharmacokinetic and pharmacodynamic evaluation of a novel proton pump inhibitor, YH1885, in healthy volunteer." J Clin Pharmacol. 2004; 44(1): 73-82.

Zhou et al. "DNA transfection mediated by cationic liposomes containing lipopolylysine: characterization and mechanism of action." Biochim Biophys Acta. 1994; 1189(2); 195-203.

Zhou et al. "Lipophilic polylysines mediate efficient DNA transfection in mammalian cells." Biochim Biophys Acta. 1991; 1065(1): 8-14.

European search report and opinion dated Apr. 26, 2013 for EP Application No. 6846696.0.

Kang, H.W., et al., "Targeting of MPEG-Protected Polyamino Acid Carrier to Human E-Selectin In Vitro," Amino Acids 23(1-3):301-308, Jan. 2002.

Partial European Search Report dated Dec. 21, 2018, issued in corresponding European Application No. 18194631.0, filed Dec. 19, 2006, 20 pages.

1.

2.

3.

1.

2.

3.

1.

2.

3.

HYDROPHOBIC CORE CARRIER COMPOSITIONS FOR DELIVERY OF THERAPEUTIC AGENTS, METHODS OF MAKING AND USING THE SAME

CROSS-REFERENCES TO RELATED APPLICATIONS

This application claims priority as a continuation of U.S. patent application Ser. No. 14/087,523, filed Nov. 22, 2013, which is a continuation under 35 U.S.C. 120 of U.S. patent application Ser. No. 11/613,183, filed Dec. 19, 2006, which claims the benefit of priority under 35 U.S.C. section 119(e) to U.S. Provisional Application 60/813,629 filed on Dec. 19, 2005.

GOVERNMENT LICENSE RIGHTS

This invention was made with government support under DK069727, awarded by the National Institutes of Health. The government has certain rights in the invention.

BACKGROUND

The development of new drugs, formulations and other systems for administration of physiologically active peptides, proteins, organic drugs, other therapeutics and materials is driven by the need to achieve the desirable physiological effects. With respect to peptides and proteins, many of them have been observed to be unstable in the gastrointestinal tract and therefore may need to be stabilized or protected or delivered via systemic circulation. In addition, peptides and proteins that have low molecular masses tend to have short biological half-lives due to their efficient removal from systemic circulation via kidneys. For example, a fraction of these peptides and proteins can also be removed via reticuloendothelial uptake due to recognition by monocyte/macrophages or as a result of opsonization by complement components. Many peptides and proteins can also lose their activity in vivo due to proteolysis (peptide bond cleavage).

In part to circumvent these undesirable effects, a drug delivery system may be used. There are several drug delivery strategies that can be useful for peptide and protein delivery in vivo. First, a continuous systemic infusion of drug via a pump can be employed. This strategy is proven efficient in clinical practice but may be impractical for outpatients requiring high levels of mobility, associated disadvantages of quality of life and potential intravenous (I.V.) line infections.

Second, peptides and proteins can be included in an implantable pump comprised of a capsule with a membrane allowing diffusion of the drug, for example, at a desirable release rate. Due to limited volume of these capsules, peptides and proteins are often used in a concentrated formulation which leads to a loss of solubility due to aggregation and potential loss of specific activity. In most cases, the drug is usually released into the extracellular space and distributed in lymphatics. Overall concentration of peptide or protein may be affected by local lymph node activity and the efficacy of lymph node drainage of the implantation site. There is also a potential of host reaction to capsule material but in general, this side effect is infrequent.

Third, the drug release system can be made biodegradable as a result of encapsulation or inclusion into degradable drug delivery vehicles or carriers, e.g. polymeric matrices, particles or membrane vesicles (liposomes). These delivery systems are usually either implantable or injectable. Implantable drug delivery systems are often placed under the epidermis where the components of the system are usually slowly degraded as a result of biological activity of surrounding cells (i.e. as a result of the release of enzymes degrading chemical bonds that hold these implants together).

U.S. Pat. No. 5,871,710 to Bogdanov et al. which hereby incorporated by reference discloses a biocompatible graft co-polymer adduct including a polymeric carrier, a protective chain linked to the polymeric carrier, a reporter group linked to the carrier or to the carrier and protective chain, and a reversibly linked Pt(II) compound for diagnosis. However, Bogdanov et al. does not disclose a therapeutic agent delivery composition that works for a wide variety of therapeutic agents and has a means of adjusting the release rates. U.S. Pat. No. 7,138,105 to Bolotin which hereby incorporated by reference discloses a biocompatible graft co-polymer comprising of a metal bridge flanked by two metal binding molecule wherein one of the metal binding molecule is part of or covalently linked to the therapeutic agent. The bridge provides a link between the carrier and therapeutic agent capable of binding metals.

There still exists a need for a sustained release therapeutic agent delivery system that works for a wide range of therapeutic agents and where the release rate is readily controlled. The instant application discloses a biocompatible composition comprising of a hydrophobic core that can reversibly bind a therapeutic agent wherein the extent of hydrophobicity of the core can be altered to control the release rate of the reversibly bound therapeutic agent.

SUMMARY

It is an object of the present invention to provide a sustained release therapeutic agent delivery system that is safe, biocompatible, readily prepared from known chemistries and compounds, amenable to a wide variety of therapeutic agents, and where the release rate can be readily adjusted by simple mechanisms of altering physical characteristics of the delivery system.

It is a further object of the present invention that the sustained release delivery system includes a targeting moiety for efficient delivery of the therapeutic agent to a site in need thereof.

It is another object of the present invention to provide a method of treating a disorder by delivering a therapeutic agent to a patient in need thereof in a controlled manner and at a release rate that is safe and effective and readily adjusted to be so.

It is another object of the present invention to provide a method of solubilizing poorly soluble molecules for drug delivery.

The subject invention results from the realization that the hydrophobic interactions between carrier systems of the present invention and therapeutic agents may be readily adjusted to control the release of the therapeutic agent, or in a broader sense, a "load molecule." Carriers that are safe and non-immunogenic may be prepared that have both high loading capacity and adjustable release rates by controlling the hydrophobic character of the carrier.

In part, the present invention is directed towards novel drug delivery systems or imaging agent, and methods of making and using the same.

The present invention is primarily directed to a hydrophobic-core carrier composition comprising hydrophobic groups covalently attached to a carrier and an active agent of interest (load molecule) bound to the hydrophobic groups by hydrophobic interaction.

In one embodiment, the present invention relates to a biocompatible hydrophobic-core carrier composition comprising: (i) a polymeric carrier comprising a backbone wherein the carrier is polylysine, polyaspartic acid, polyglutamic acid, polyserine, polythreonine, polycysteine, polyglycerol, polyethyleneimines, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, or carboxymethylated oligosaccharides; and (ii) a plurality of hydrophobic groups capable of binding a load molecule and covalently linked to the polymeric carrier, wherein each hydrophobic group has a molecular weight of less than 1,000 Daltons independent of the carrier molecular weight, wherein the hydrophobic group is linear alkyl, branched alkyl, phenyl, naphthyl, cholesterol, vitamin D, and/or vitamin E.

In another embodiment, the present invention relates to a biocompatible hydrophobic-core carrier composition comprising (i) a carrier comprising a backbone; (ii) a plurality of hydrophobic groups capable of binding a load molecule, wherein each hydrophobic group is covalently linked to the carrier, and each has a molecular weight of less than about 1,000 Daltons independent of the polymeric carrier weight; and (iii) a plurality of polymeric protective side chains, wherein each protective side chain is covalently linked to the carrier and each has a molecular weight between about 400 and 20,000 Daltons independent of the carrier weight. In a further embodiment, the aforementioned composition further comprises a second set of hydrophobic groups with a covalently linked protective side chain, wherein the hydrophobic groups have a first and second end, the first end is covalently linked to the carrier, the second end is covalently linked to the protective side chain; the hydrophobic groups of this second set have a molecular weight of less than 1,000 Daltons independent of the carrier and protective side chain weights; and the protective side chain linked to the hydrophobic group has a molecular weight between 400 and 20,000 Daltons independent of the hydrophobic group weight.

In another embodiment, the present invention relates to a biocompatible hydrophobic-core carrier composition comprising (i) a carrier comprising a backbone; (ii) a plurality of hydrophobic groups capable of binding a load molecule, wherein each hydrophobic group is covalently linked to the carrier, and each has a molecular weight of less than about 1,000 Daltons independent of the backbone weight; and (iii) a second set of a plurality of hydrophobic groups with a covalently linked protective side chain, wherein the hydrophobic groups have a first and second end, the first end is covalently linked to the carrier, the second end is covalently linked to the protective side chain; the hydrophobic group has a molecular weight of less than 1,000 Daltons independent of the carrier and protective side chain weights; and the protective side chain linked to the hydrophobic group has a molecular weight between 400 and 20,000 Daltons independent of the hydrophobic group weight.

In another embodiment, the present invention relates to a biocompatible hydrophobic-core carrier composition, comprising: (i) a carrier comprising a backbone; and (ii) a plurality of hydrophobic groups with a covalently linked protective side chain, wherein the hydrophobic group has a first and second end; the first end is covalently linked to the carrier, the second end is covalently linked to the protective side chain; the hydrophobic group has a molecular weight between 150 to 1000 Daltons independent of the carrier and protective side chain weights, and; the protective side chain has a molecular weight between about 400 and 20,000 Daltons independent of the carrier and hydrophobic group weights.

In a further embodiment the present invention relates to any of the aforementioned compositions, wherein the hydrophobic group comprises an alkyl group. In a further embodiment, the alkyl group comprises a branched alkyl group. In a further embodiment, the alkyl group comprises a double bond. In a further embodiment, the alkyl group comprises an ethyl or propyl group. In a further embodiment, the alkyl group is a butyl, pentyl, or hexyl group. In a further embodiment, the alkyl group is $CH_3(CH_2)_nCH_2—$, $CH_3(CH_2)_nCH_2NH—$, $CH_3(CH_2)_nCO—$, $CH_3(CH_2)_nCH_2O—$, $CH_3(CH_2)_nCH_2S—$, $—OC(CH_2)_nCH_2—$, $—OC(CH_2)_nCH_2NH—$, $—OC(CH_2)_nCO—$, $—OC(CH_2)_nCH_2O—$, $—OC(CH_2)_nCH_2S—$, $—HNC(CH_2)_nCH_2—$, $—HNC(CH_2)_nCH_2NH—$, $—HNC(CH)_nCO—$, $—HNC(CH_2)_nCH_2O—$, $—HNC(CH_2)_nCH_2S—$, $—OCH_2(CH_2)_nCH_2—$, $—OCH_2(CH_2)_nCH_2NH—$, $—OCH_2(CH_2)_nCO—$, $—OCH_2(CH_2)_nCH2O-$, or $—OCH_2(CH_2)_nCH_2S—$ group; wherein "n" is 4-34, inclusive. In a further embodiment the present invention relates to the aforementioned compositions with hydrophobic chain covalently linked to protective side chains, wherein the hydrophobic chain with covalently attached protective side chain is independently selected from the group consisting of $—(CH_2)_4NHCO(CH_2)_nOC-A-OR_3$, $—(CH_2)_4NHCO(CH_2)_n$ $NHCO(CH_2)_yCO-A-OR_3$, $—CH_2OOC(CH_2)_nOC-A-OR_3$, $—CH_2OOC(CH_2)_nNHCO(CH_2)_yCO-A-OR_3$, $—CH(CH_3)OOC(CH_2)_nOC-A-OR_3$, $—CH(CH_3)00C(CH_2)nNHCO(CH_2)yCO-A-OR_3$, $—CH_2COOC(CH_2)_nCO-A-OR_3$, $—CH_2COOC(CH_2)_nNHCO(CH_2)_yCO-A-OR_3$, $—CH_2CONH(CH_2)_nNHC$ $OCH_2CH_2-A-OR_3$, $—CH_2CONH(CH_2)_nNHCO(CH_2)_yCO-A-OR_3$, $—(CH_2)_2COOC(CH_2)_n-A-OR_3$, $—(CH_2)_2COOC(CH_2)_n NHCO(CH_2)_yCO-A-OR_3$, $—(CH_2)_2CONH$ $(CH_2)_nNHCOCH_2CH_2-A-OR_3$, $—(CH_2)_2CONH$ $(CH_2)_nNHCO(CH_2)_yCO-A-OR_3$, $—(C_6H_4)OCO(CH_2)_nCO-A-OR_3$, and $—(C_6H_4)OCO(CH_2)_nNHCO(CH_2)_yCO-A-OR_3$, wherein n is 2-22; y is 2-6; $R_3$ is H, $(CH_2)_pCH_3$ or $(CH_2)_pCOOH$, wherein p is 0-7; and A is $[OCH_2CH_2]_x$ or $[OCHCH_3CH_2]_x$, wherein x is 17-250, or various combinations of $[OCH_2CH_2]$ and $[OCHCH_3CH_2]$ with a total of 17-250 units. In another embodiment, the hydrophobic group comprises an aromatic ring compound. In a further embodiment, the aromatic ring is phenyl. In a further embodiment, the aromatic ring is naphthyl. In a further embodiment, the aromatic ring compound is cholesterol. In a further embodiment, the aromatic ring compound is fluorescien and the carboxyl group in fluorescien will act as orienting molecule.

In another embodiment, the present invention relates to any of the aforementioned compositions with protective chain, wherein the protective side chain comprises anyone from a group consisting of polyethyleneglycol, polypropylene glycol, a co-polymer of polyethyleneglycol and polypropyleneglycol, methoxypolyethyleneglycol, methoxypolypropyleneglycol, or a co-polymer of methoxypolyethyleneglycol and methoxypolypropyleneglycol. In a further embodiment, the protective side chain comprises a block co-polymer of polyethyleneglycol and one of the group of polyamino acids, polysaccharides, polyamidoamines, polyethyleneamines, or polynucleotides. In a further embodiment, the protective side chain comprises a co-polymer of polyethyleneglycol including a monoester of a dicarboxylic acid. In a further embodiment, the protective side chain comprises a sialic acid chain. In a further embodiment, the protective side chain has a molecular weight of 500-20,000 daltons. In a further embodiment, the protective side chain comprises a monoesterified derivative thereof, preferably methoxypolyethyleneglycol-ester, methoxypolypropyleneglycol-ester, or a co-polymer of methoxypolyethyleneglycol and methoxypolypropyleneglycol-ester. In a further embodiment, the protective side chain comprises anyone of; polyethyleneglycol monoamine, methoxypolyethyleneglycol monoamine, polypropyleneglycol monoamine, methoxypolypropyleneglycol monoamine, polyethyleneglycol hydrazine, methoxypolyethyleneglycol hydrazine, polypropyleneglycol hydrazine, methoxypolypropyleneglycol hydrazine, polyethyleneglycol imidazolide, methoxypolyethyleneglycol imidazolide, polypropyleneglycol imidazolide, methoxypolypropyleneglycol imidazolide, polyethyleneglycol diacid, methoxypolyethyleneglycol diacid, polypropyleneglycol diacid, methoxypolypropyleneglycol diacid, wherein the terminal amine, hydrazine, imidazolide, or acid is used to attached to the carrier, hydrophobic group, or targeting molecule. In a further embodiment, the protective side chain comprises methoxy polyethylene glycol) imidazolide block-copolymer of poly (ethylene glycol) and one or several polymers represented by polyaminoacid, poly-lactideglycolide co-polymer, polysaccharide, polyamidoamine, polyethyleneimine or polynucleotide (see polymeric carrier) where these blocks are preferably alternated to give a preferably linear block-copolymer. In a further embodiment, the protective side chain is linked to the carrier or hydrophobic group by preferably a single linkage.

In another embodiment, the present invention relates to anyone of the aforementioned compositions with protective chain and carrier, wherein the carrier comprises anyone of the group consisting of; solid support, nanoparticle, and microparticle. In a further embodiment the carrier comprises a block co-polymer. In a further embodiment the carrier comprises a polymeric carrier. In a further embodiment, the polymeric carrier is selected from the group consisting of polyamino acids, polyethyleneimines, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, and carboxymethylated oligosaccharides. In a further embodiment, the polymeric carrier is a polyamino acid having 2 to 560 amino acid units. In a further embodiment, the polymeric carrier is a polyamino acid having a molecular weight of 1,000-100,000 daltons. In a further embodiment the polymeric carrier is a polyamino acid consisting of a single species of amino acid. In a further embodiment, the polymeric carrier is a polyamino acid comprising of at least two different species of amino acids. In a further embodiment the polymeric carrier is a polyamino acid and wherein the polyamino acid is a block co-polymer. In a further embodiment the polymeric carrier is a polyamino acid and wherein the polyamino acid comprises polyamino acid fragments linked by cleavable bonds. In a further embodiment the cleavable bonds are S—S bonds. In a further embodiment the polymeric carrier is a polyamino acid selected from the group consisting of poly-L-lysine, poly-D-lysine, poly-alpha,beta-(2-aminoethyl)-D,L aspartamide, poly-L-aspartic acid, poly-D-aspartic acid, poly-L-glutamic acid, poly-D-glutamic acid, poly-L-serine, poly-D-serine, poly-L-threonine, poly-D-threonine, poly-L-tyrosine, or poly-D-tyrosine. In a further embodiment the polymeric carrier is a polyamino acid and the polyamino acid is non-proteinaceous.

In another embodiment, the present invention relates to any of the aforementioned compositions further comprising of targeting molecules covalently attached to the protective chains, hydrophobic groups or the carrier. In a further embodiment, the present invention relates to any of the aforementioned compositions with targeting molecule, wherein the targeting molecule is selected from the group consisting of an antibody, fragment of an antibody, chimeric antibody, enzyme, quasi-substrate of enzymes, lectin, saccharide ligand, peptide, protein, receptor ligand, cell surface binding protein, cell surface binding peptide, cell surface binding compound, extracellular matrix binding peptide, extracellular matrix binding protein, extracellular matrix binding compounds.

In another embodiment, the present invention relates to any of the aforementioned compositions further comprising of orienting molecules covalently attached to the carrier. In a further embodiment the present invention relates to any of the aforementioned compositions with orienting molecule, wherein the orienting molecule comprises anyone of peptide, sulfate moiety, sulfonate moiety, phosphate moiety, phosphonate moiety, bisphosphonate moiety, carboxyl moiety, amino moiety, lysine, and arginine. In a further embodiment, the present invention relates to any of the aforementioned compositions with orienting molecule, wherein the orienting molecule comprises a metal ion that can form a bridge between the polymeric backbone and load molecule.

In another embodiment, the present invention relates to any of the aforementioned compositions further comprising load molecule, wherein load molecule is any molecule that can reversibly bind any of the aforementioned compositions. In a further embodiment, the present invention relates to any of the aforementioned compositions further comprising any combination of load molecules dissociably linked to the hydrophobic groups, targeting molecules, orienting molecules, and/or protective sidechains. In a further embodiment, the load molecule is an imaging agent. In a further embodiment, the load molecule is a therapeutic agent. In a further embodiment, the therapeutic agent is cytokine, lymphokine, hormone, hormone agonist, hormone antagonist, antibiotic, analgesic, toxin, photo-toxin, cytostatic agent, cytotoxic agent, psychotropic agent, steroidal anti-inflammatory agent, non-steroidal anti-inflammatory agent, immunosuppressive agent, anti-bacterial agent, anti-viral drug, anti-fungal drug, chelator, vitamin, protease inhibitor, pesticide, aminoglycoside, polymyxin, ACE inhibitor, peptide, protein, antibody, antibody fragment, recombinant peptide, peptide isolated from plants, peptide isolated from fungi, peptide isolated from animals, peptide isolated from bacteria, peptide isolated from viruses, peptides isolated from cells in culture, synthetic peptide, peptidomimetic compound, organic compound, synthetic organic compound, organic compound isolated from plants, organic compound isolated from fungi, organic compound isolated from animals, organic compound isolated from bacteria, organic compound isolated from viruses, organic compound isolated from cells in culture, organometallic compound, deoxyribonucleic acid, ribonucleic acid, oligonucleotide, nucleic acid derivative, oligosaccharide, carbohydrate; lipid; photo-sensitive organic compound, and proteoglycan.

In another embodiment, the present invention relates to any of the aforementioned compositions with load molecule, wherein the load molecule is a therapeutic agent selected from the group consisting of glucagon-like-peptide, glucagon-like-peptide derivatives, exenatide, glucagon-like-peptide-1, glucagon-like-peptide-2, leptin fragment, Gastric inhibitory polypeptide (GIP), Epidermal Growth Factor (EGF) receptor ligand, EGF, Transforming Growth Factor alpha (TGF-alpha), Betacellulin, Gastrin/Cholecystokinin receptor ligand, Gastrin, Cholecystokinin, lysostaphin, interferon, interferon gamma, interferon beta, interferon alpha, interleukin-1, interleukin-2, interleukin-4, interleukin-6, interleukin-8, interleukin-10, interleukin-12, tumor necrosis factor, tumor necrosis factor alpha, tumor necrosis factor beta, auristatin, nisin, insulin, insulin-like growth factor, growth hormone, growth hormone releasing hormone (GHRH), nerve growth factor, brain-derived neurotrophic factor, enzymes, endostatin, angiostatin, trombospondin, urokinase, streptokinase, blood clotting factor VII, blood clotting factor VIII, granulocyte-macrophage colony-stimulating factor (GM-CSF), granulocyte colony-stimulating factor (G-CSF), thrombopoietin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastin, prostaglandins, epoprostenol, prostacyclin, cyclosporine, vasopressin, terlipressin, desmopressin, cromolyn sodium (sodium or disodium chromoglycate), vasoactive intestinal peptide (VIP), vancomycin, antimicrobials, polymyxin b, anti-fungal agents, anti-viral agents, enfuvirtide, doxorubicin, etoposide, fentanyl, ketamine, and vitamins. In a further embodiment, the therapeutic agent is glucagon-like-peptide-1. In a further embodiment, the therapeutic agent is glucagon-like-peptide-2. In a further embodiment, the therapeutic agent is lysosthaphin. In a further embodiment, the therapeutic agent is interferon. In a further embodiment, the therapeutic agent is interferon alpha. In a further embodiment, the therapeutic agent is interferon beta. In a further embodiment, the therapeutic agent is interferon gamma. In a further embodiment, the therapeutic agent is nisin. In a further embodiment, the therapeutic agent is Epidermal Growth Factor (EGF) receptor ligand. In a further embodiment, the therapeutic agent is EGF. In a further embodiment, the therapeutic agent is Transforming Growth Factor alpha (TGF-alpha). In a further embodiment, the therapeutic agent is betacellulin. In a further embodiment, the therapeutic agent is Gastrin/Cholecystokinin receptor ligand. In a further embodiment, the therapeutic agent is Gastrin. In a further embodiment, the therapeutic agent is Cholecystokinin.

In another embodiment the present invention relates to a method of treating a patient for insulin-insufficient diabetes comprising; (i) administering a therapeutically effective amount of hydrophobic-core carrier composition with load molecule described above, wherein the load molecule is GLP-1, EGF receptor ligand, EGF, TGF-alpha, Betacellulin, Gastrin/Cholecystokinin receptor ligand, Gastrin, or Cholecystokinin, and optionally (ii) administering a therapeutically effective amount of protom pump inhibitor. In further embodiment, the proton pump inhibitor is omeprazole.

In another embodiment the present invention relates to a method of treating a patient for insulin-insufficient diabetes comprising; (i) administering a therapeutically effective amount of hydrophobic-core carrier composition with load molecule described above, wherein the load molecule is GLP-1, (ii) administering a therapeutically effective amount of hydrophobic-core carrier composition with load molecule described above, wherein the load molecule is Gastrin/Cholecystokinin receptor ligand, Gastrin, or Cholecystokinin, and optionally (iii) administering therapeutically effective amount of protom pump inhibitor. In further embodiment, the proton pump inhibitor is omeprazole.

In another embodiment the present invention relates to a method of treating a patient for insulin-insufficient diabetes comprising; (i) administering a therapeutically effective amount of hydrophobic-core carrier composition with load molecule described above, wherein the load molecule is EGF receptor ligand, EGF, TGF-alpha, or Betacellulin, (ii) administering a therapeutically effective amount of hydrophobic-core carrier composition with load molecule described above, wherein the load molecule is Gastrin/Cholecystokinin receptor ligand, Gastrin, or Cholecystokinin, and optionally (iii) administering therapeutically effective amount of protom pump inhibitor. In further embodiment, the proton pump inhibitor is omeprazole.

In another embodiment the present invention relates to a method of treating a patient for an infection comprising administering to the patient in need thereof a therapeutically effective amount of any of the hydrophobic-core carrier compositions described above, wherein the load molecule is lysostaphin.

These embodiments of the present invention, other embodiments, and their features and characteristics, will be apparent from the description, drawings and claims that follow.

with 2 mg GLP-1 alone or 2 mg GLP-1 in PGC-HC formulation. Terminal blood draws were done at given time points. The total GLP1 (carrier bound and unbound) is measured by Elisa kit from Linco measured by Elisa kit from Linco (LINCO Research, St. Charles, Mo.).

Figure 44:
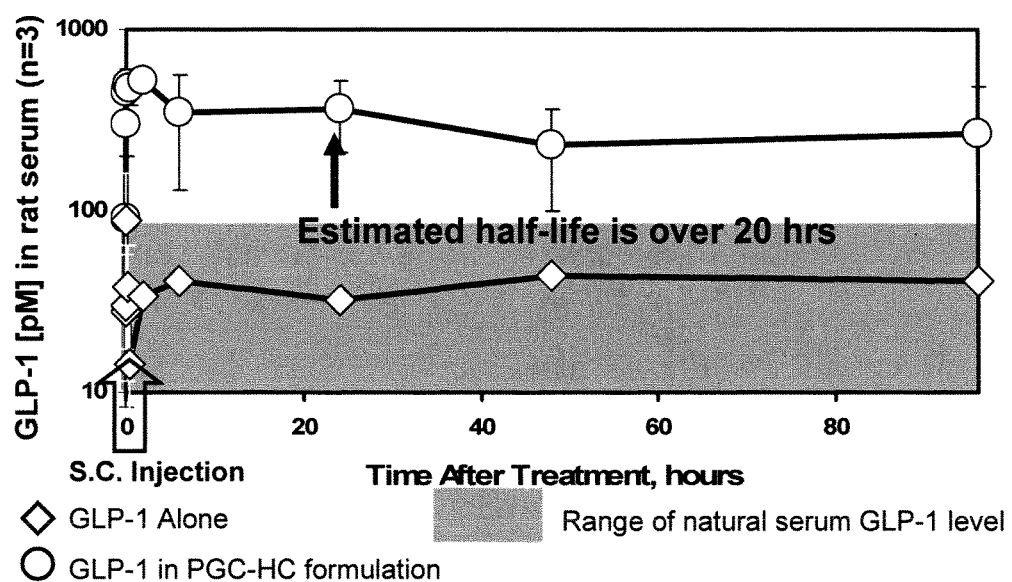

FIG. 44. Time dependent decrease in total GLP1 in the blood after subcutaneous (s.c.) administration of GLP1 and formulated GLP1 (PGC-HC18 containing 2% by weight of GLP1). The PGC-HC18 used in the formulation is a 20 kDa polylysine where 55% of the amino groups were reacted with PEG succinate of 5 kDa molecular weight and the remaining aminogroups were reacted with stearic acid or C18. The elimination half-life of GLP1 administered alone is just a few minutes while the formulated GLP1 has half-life of at least 20 hours. Pre-cannulated male Sprague Dawley rats were injected s.c. with 1 ug GLP-1 alone or 1 ug GLP-1 in PGC-HC formulation. Blood draws were done through the jugular vein cannula and serum was stored at −80° C. until analysis. The total GLP 1 (PGC-HC18 bound and unbound) are measured by Elisa kit from Linco (LINCO Research, St. Charles, Mo.).

Figure 45:
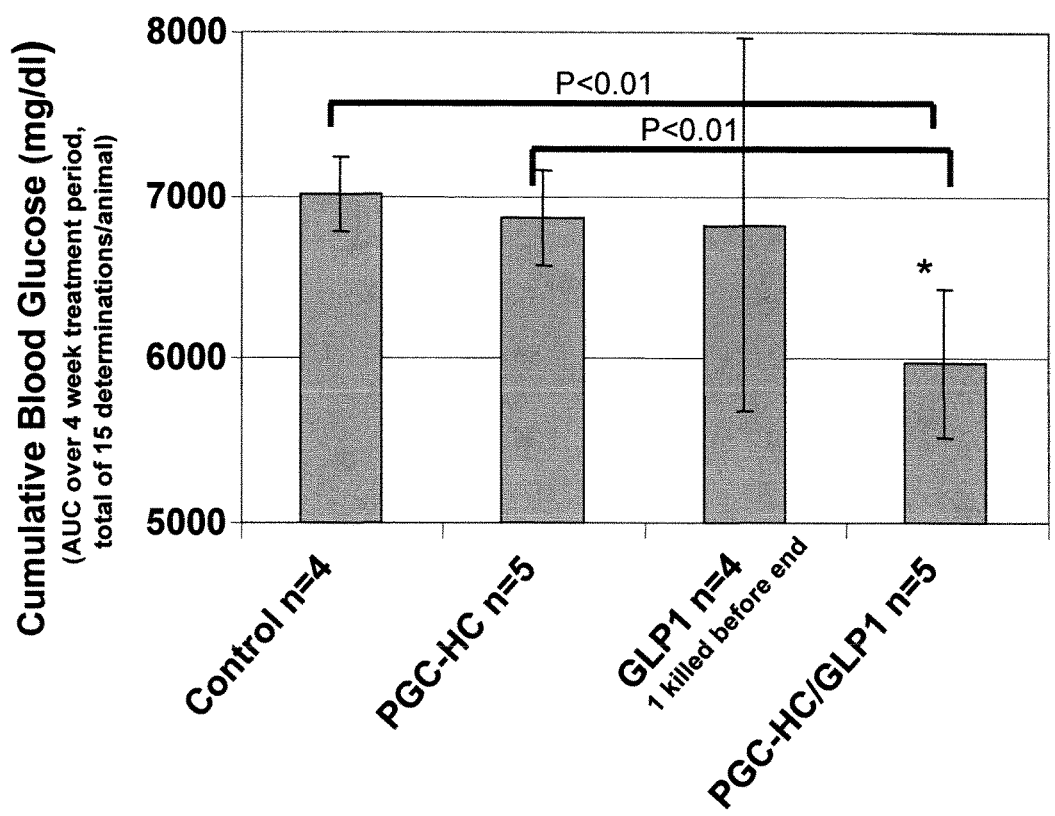

FIG. 45. This shows the average total of 15 glucose sampling over a 4 week-treatment period that started 13 days after diabetes induction with 60 mg/kg streptozotocin. Prior to treatment the blood glucose levels taken every 2 days for 6 days prior to treatment are between 300-600 mg/dl. After randomization the average blood sugar level of each group are between 421 and 433 mg/dl. Rats were treated every 2 days subcutaneously. Control group received saline, Carrier control received PGC-HC18 only (1 mg in PBS), GLP-1 group received 20 ug GLP-1, and PGC-HC18/GLP-1 received 1 mg PGC-HC18 loaded with 20 ug GLP-1. The PGC-HC 18 used in the formulation is a 20 kDa polylysine where 55% of the amino groups were reacted with PEG succinate of 5 kDa molecular weight and the remaining aminogroups were reacted with stearic acid or C18. One of the GLP-1 animals needed to be sacrificed at 2 week time point due to severe diabetes associated with severe weight loss. Non-fasting sugar levels taken every 2 days were added together to obtain area under the curve (AUC) for each animal to average out cyclical variability in each animal. There is significant difference between formulated GLP-1-treated animals and Control or PGC-HC only treated animals (* $P<0.01$).

Figure 46:
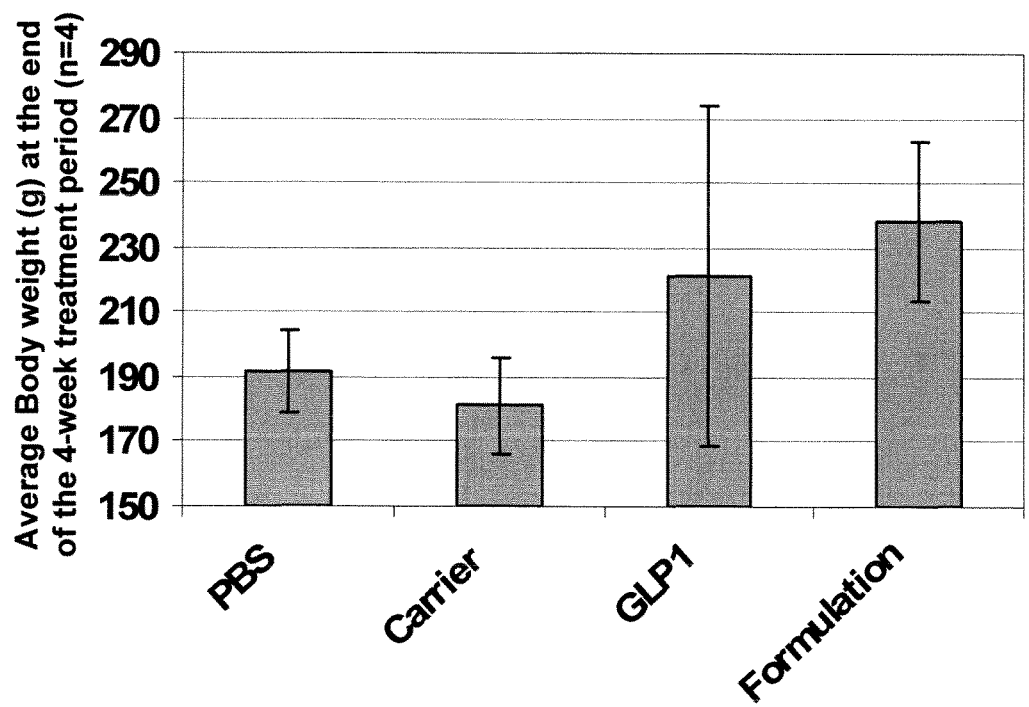

FIG. 46. This is a graph showing the average body weight of streptozotocin diabetic rats at the end of the 4 week treatment period (+/−standard deviation; n=4) that started at $13^{th}$ day after diabetes induction with 60 mg/kg streptozotocin. The starting weights of all animals prior to streptozotocin treatment are within 240 to 260 grams. Control group received saline, Carrier control received PGC-HC18 only (1 mg in PBS), GLP-1 group received 20 ug GLP-1, and PGC-HC18/GLP-1 received 1 mg PGC-HC18 loaded with 20 ug GLP-1. The PGC-HC18 used in the formulation is a 20 kDa polylysine where 55% of the amino groups were reacted with PEG succinate of 5 kDa molecular weight and the remaining aminogroups were reacted with stearic acid or C18. The streptozotocin-diabetic rats treated with PBS or carrier alone lost significantly more weight than animals treated with formulation (P<0.01). The group of animals treated with GLP 1 alone without the carrier showed greater variability in response compared to those rats treated with GLP-1 formulation.

Figure 47:
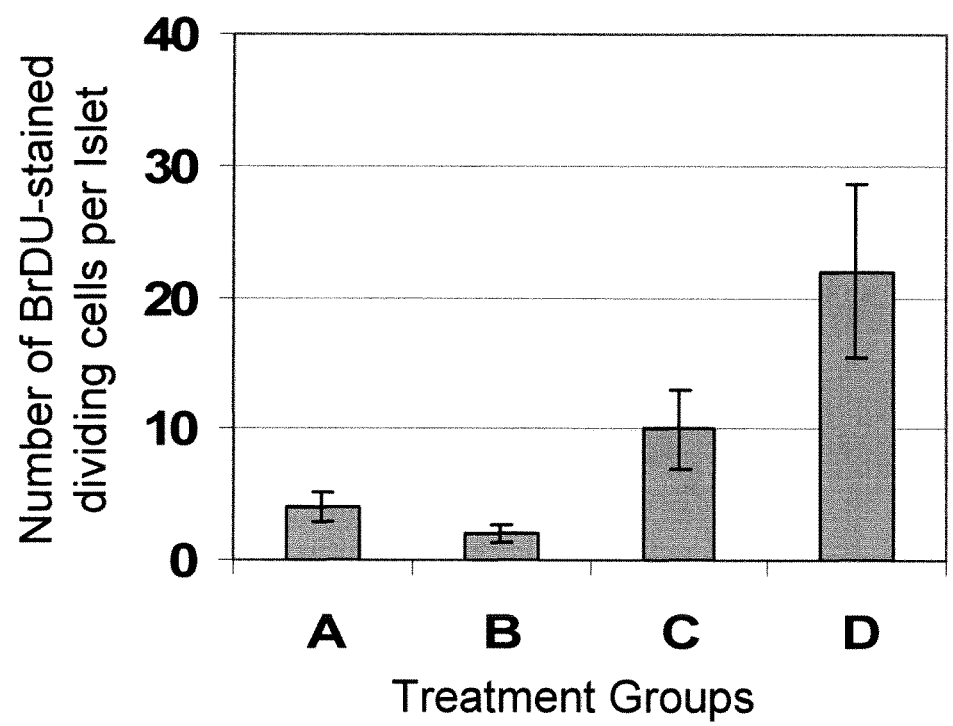

FIG. 47. The graph was derived from histology sections of rat pancreata of streptozotocin diabetic rats at the end of the 4 week treatment period (+/−standard deviation; n=4) that started at 13th day after diabetes induction with 60 mg/kg streptozotocin. Rat pancreata were stained with anti-BrdU-antibody and hematoxylin and photographed at magnification of 250×. The islets were located and the number of BrDU positive nuclei in each islet was counted. Control group received saline (A), Carrier control received PGC-HC18 only (1 mg in PBS) (B), GLP-1 group received 20 ug GLP-1 (C), and PGC-HC18/GLP-1 received 1 mg PGC-HC18 loaded with 20 ug GLP-1 (D). The PGC-HC18 used in the formulation is a 20 kDa polylysine where 55% of the amino groups were reacted with PEG succinate of 5 kDa molecular weight and the remaining aminogroups were reacted with stearic acid or C18. The anti-BrdU-antibody staining shows significantly more cell divisions are occurring in the islets of the GLP-1 and GLP-1/PGC-HC18 formulation treated rats (C and D) as compared with the PBS or empty carrier treated rats (A and B). Additionally, there are more BrdU positive cells in the exocrine tissue of GLP-1/PGC-HC18 formulation treated rats (not shown), which might indicate neogenesis of islet cells from ductal progenitors.

Figure 34:
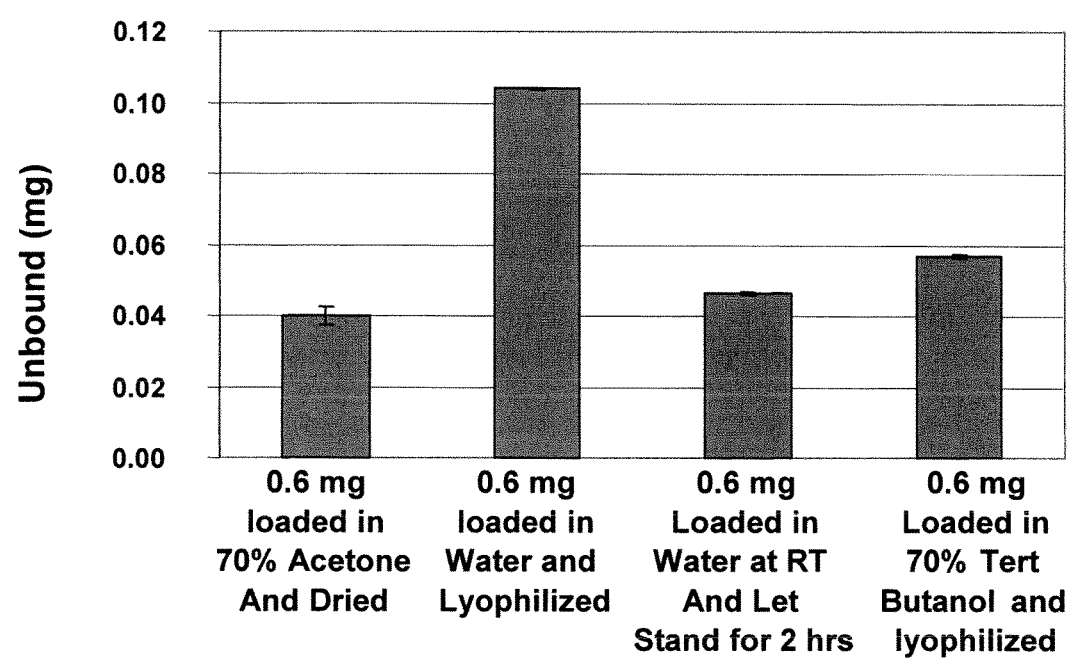
FIG. 34. This is a figure showing the loading efficiency of hydrophobic carrier under various conditions (n=6). The y-axis is the amount that did not bind the carrier. In this figure. 10 mg of PGC-HC24 (20PLPEG5-55 C24; this is a 20 kDa polylysine where 55% of the amino groups were reacted with PEG succinate of 5 kDa molecular weight and the remaining aminogroups were reacted with lignoceric acid or C24) was loaded with 0.6 mg of GLP 1 under various conditions indicated in the x-axis. After loading, all samples were made up to 1 ml PBS (pH 7.4) and filtered through 100 kDa molecular cut-off cellulose filter (Millipore, Bedford, Mass.) and the free GLP-1 in the each filtrate was quantified using reverse phase HPLC. The filter does not bind GLP-1 as determined by control sample without carrier (not shown). The condition that shows highest loading is the 70% acetone followed by drying. This specific loading process (with acetone) is also expected to work for other proteins whereas the other processes, especially the water loadings may vary from protein to protein. This process exploits the ability of the solvent to expose hydrophobic portion of the protein and the hydrophobic portion of the carrier. For large protein 10-30 kDa, the risk of denaturation can be minimize by decreasing the amount of organic solvent.
Figure 48:
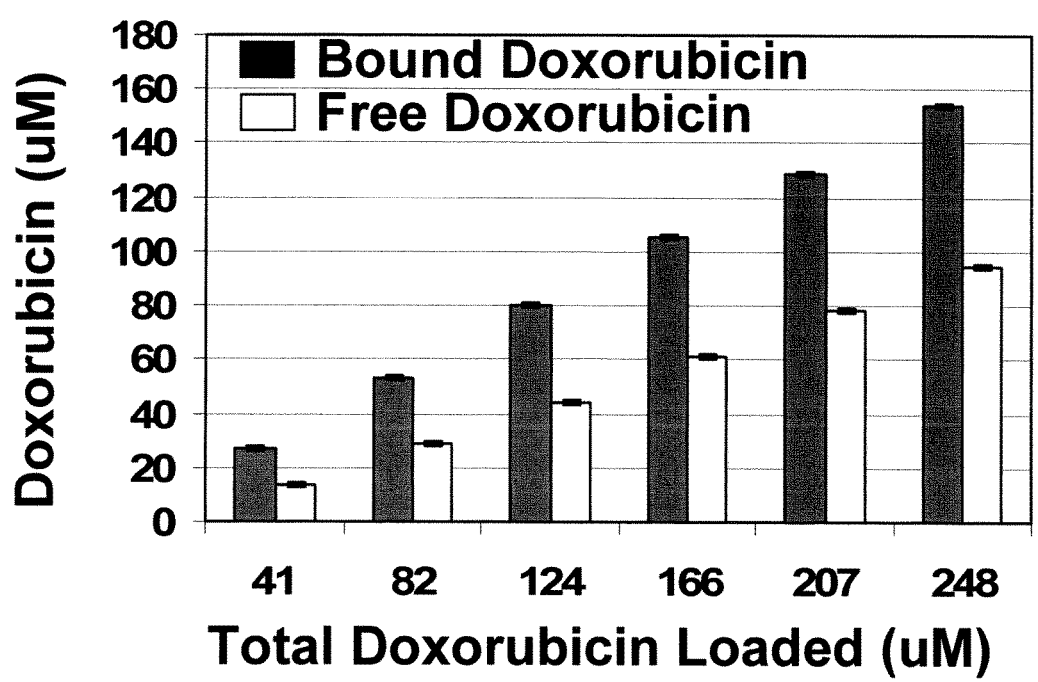

FIG. 48. This shows that PGC-HC18 binds organic compounds (e.g. doxorubicin) with 6-7 sites with Kd of 315 uM. PGC-HC18 is a 20 kDa polylysine where 55% of the amino groups were reacted with PEG succinate of 5 kDa molecular weight and the remaining aminogroups were reacted with stearic acid or C18. Doxorubicin is an anticancer drug. In this experiment 8 mg of hydrophobic core carrier was loaded (as described in FIG. 34, acetone method) with varying amounts of doxorubicin. Each loaded carrier was dissolved in 1 ml PBS and allowed to equilibrate for 2 hours. Each solution containing free and bound doxorubicin was filtered through 100 kDa molecular cut off filter and each filtrate containing free doxorubicin was quantified by reverse phase HPLC. The bound doxorubicin determined from the total doxorubicin used during loading minus the free doxorubicin determined by HPLC.

Figure 49:
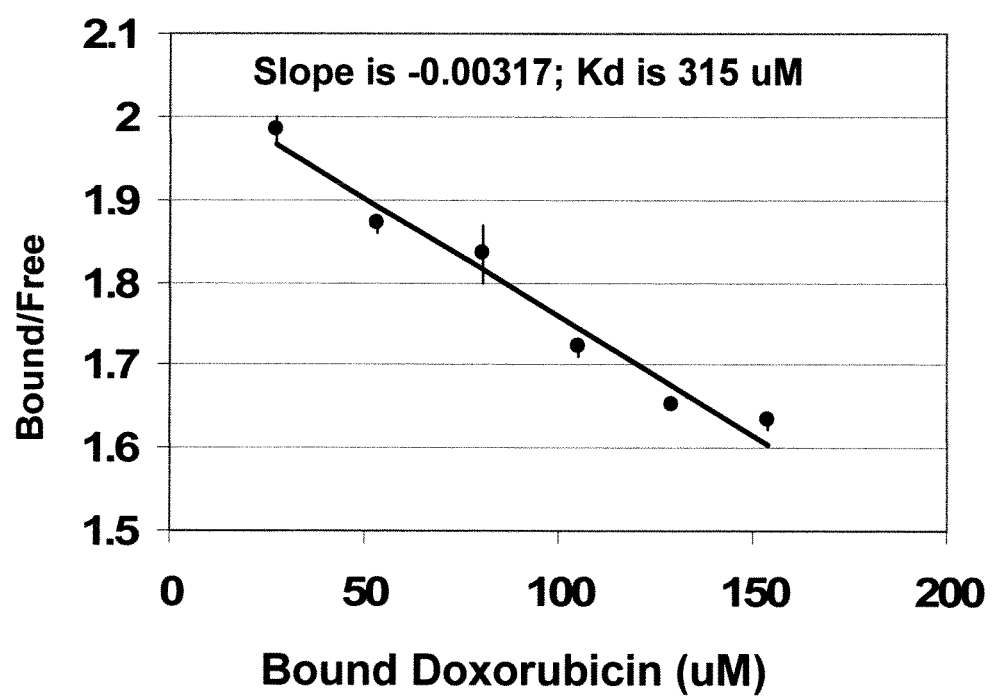

FIG. 49 shows the results of loading of doxorubicin to PGC-HC18. PGC-HC18 is a 20 kDa polylysine where 55% of the amino groups were reacted with PEG succinate of 5 kDa molecular weight and the remaining aminogroups were reacted with stearic acid or C18. Doxorubicin is an anticancer drug. This graph shows the amount of PGC-HC18 bound and free doxorubicin when 8 mg of PGC-HC 18 was loaded with various amount of doxorubicin (x-axis) using the acetone method described in FIG. 34. After loading, each loaded carrier was dissolved in 1 ml PBS and allowed to equilibrate for 2 hours. The mixture of PGC-HC18 bound and the free doxorubicin was separated by filtration through regenerated cellulose filter. The filtrate representing the free doxorubicin were quantified by reverse phase HPLC (n=3). The bound doxorubicin determined from the total doxorubicin used during loading minus the free doxorubicin determined by HPLC.

DETAILED DESCRIPTION OF THE INVENTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element.

The term "and/or" as used herein should be understood to mean either one, both, or any combination thereof. By way of example, "A and/or B" includes "A" or "B" or "A and B."

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, "about" or "comprising essentially of" mean ±15% of the indicated value or range, unless otherwise indicated.

The use of the alternative (e.g., "or") should be understood to mean either one, both, or any combination thereof of the alternatives.

The term "hydrophobic groups" as used herein refers to a molecule or several molecules or chemical moieties which are non-polar and provides a hydrophobic environment for load molecule to interact in order to avoid the surrounding water environment. The hydrophobic attraction is the major driving force in the folding of macromolecules, the binding of substrates to enzymes, and the formation of membranes that define the boundaries of cells and their internal compartments. Non-polar molecules are driven together in water not primarily because they have a high affinity for each other in the absence of water but because in the presence of water, they will be excluded from water because water bonds strongly to itself. Hydrophobic groups may be hydrocarbon chains and/or ring compounds that do not have positive or negative charge after incorporation into the carrier and are capable of binding to molecules by interaction that does not involve charge interactions. It is understood that some molecules can gain or lose charge with changes in pH, and this invention includes composition that contains no charge or is hydrophobic during binding to the therapeutic agent or load molecules. It is also understood that the hydrophobic group counts as a separate entity from the polymeric carrier, such that, for example, when the polymeric carrier is a polyamino acid, the natural R group on the polyamino acid is not counted as a hydrophobic group. However, the R group may be derivatized to add a hydrophobic group. For example, a hydrophobic group may be added to a polylysine carrier through amidation of the butyl amine R group. Occasionally, hydrophobic group may contain, at one end of the molecule, an amino or carboxyl groups designed as orienting molecule which should be considered separate from hydrophobic group (e.g. a fluorescein molecule with carboxyl group).

The term "orienting molecule" is used herein to refers to any molecular structure which assist the binding of the load molecule to the hydrophobic core composition of the present invention in such a way that the load molecule orients in a certain manner while interacting with the hydrophobic groups of the composition. Orienting molecule is normally attached to the polymeric carrier backbone. Orienting molecule, in most cases, enhances or strengthens the binding of load molecule to the carrier in addition to its orienting role. Orienting molecule may be selected from the group consisting of a peptide, sulfate, sulfonate, phosphate, phosphonate, bisphosphonate, lysine, and arginine. Orienting molecule may also comprise of a metal ion that can form a bridge between the polymeric backbone and load molecule. Orienting molecule may also be an amino or carboxyl moiety covalently anchored to the polymeric carrier.

The term "derivative" or "analog" as used herein refers to a compound whose core structure is the same as, or closely resembles that of, a parent compound, but which has a chemical or physical modification, such as a different or additional groups; the term includes co-polymers of parent compounds that can be linked to other atoms or molecules. The term also includes a peptide with at least 50% sequence identity with the parent peptide. The term also includes a peptide with additional groups attached to it, such as fatty acids and/or additional amino acids, compared to the parent peptide. The term also includes a polymer with additional group attached to it, such as alkoxy group, compared to the parent polymer. The term also includes branched or un-branched alkyl chain with additional group(s) attached to it compared to the parent chain.

The term "targeting moiety," "targeting molecules," or "targeting group" refers to any molecular structure which assists the construct of the composition in localizing at a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, peptides, and proteins may serve as targeting moieties. A "target" is a site to which targeted constructs or the hydrophobic core compositions bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). In still other embodiments, a target may refer to a molecular structure to which a targeting moiety binds, such as a hapten epitope, receptor, dsDNA fragment, carbohydrate or enzyme. Additionally, a target may be a type of tissue, e.g., neuronal tissue, intestinal tissue, pancreatic tissue etc.

The term "load molecule" as used herein encompasses any molecule that can be loaded in to the hydrophobic core composition of the present invention including diagnostic agents and therapeutic agents.

The term "therapeutic agents" as used herein refer to any chemical moiety that is a biologically, physiologically, or pharmacologically active substance that acts locally or systemically in a subject. Examples of therapeutic agents, also referred to as "drugs", are glucagon-like-peptide, glucagon-like-peptide derivatives, exenatide, glucagon-like-peptide-1, glucagon-like-peptide-2, leptin fragment, Gastric inhibitory polypeptide (GIP), Epidermal Growth Factor (EGF) receptor ligand, EGF, Transforming Growth Factor alpha (TGF-alpha), Betacellulin, Gastrin/Cholecystokinin receptor ligand, Gastrin, Cholecystokinin, lysostaphin, interferon, interferon gamma, interferon beta, interferon alpha, interleukin-1, interleukin-2, interleukin-4, interleukin-6, interleukin-8, interleukin-10, interleukin-12, auristatin, nisin, insulin, insulin-like growth factor 1, growth hormone, growth hormone releasing hormone (GHRH), nerve growth factor, brain-derived neurotrophic factor, enzymes, endostatin, angiostatin, trombospondin, urokinase, streptokinase, blood clotting factor VII, blood clotting factor VIII, granulocyte-macrophage colony-stimulating factor (GM-CSF), granulocyte colony-stimulating factor (G-CSF), thrombopoietin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, epoprostenol, prostacyclin, cyclosporine, vasopressin, terlipressin, desmopressin, cromolyn sodium (sodium or disodium chromoglycate), vasoactive intestinal peptide (VIP), vancomycin, antimicrobials, polymyxin b, anti-fungal agents, anti-viral agents, enfuvirtide, doxorubicin, etoposide, fentanyl, ketamine, and vitamins. Further examples of therapeutic agents, also referred to as "drugs", are described in well-known literature references such as the Merck Index, the Merck manual of diagnosis and therapy, the Physicians' Desk Reference, and The Pharmacological Basis of Therapeutics, and they include, without limitation, proteins, peptides, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), siRNA, peptides, proteins, antibodies, photodynamic agents (e.g., rhodamine 123), radionuclides (e.g., 1-131, Re-186, Re-188, Y-90, Bi-212, At-211, Sr-89, Ho-166, Sm-153, Cu-67 and Cu-64), toxins (e.g., ricin), and transcription-based pharmaceuticals.

The term "therapeutically effective amount" as used herein refers to the amount of composition that will provide a therapeutic benefit to the patient. In certain embodiments, the term refers to an amount of the therapeutic agent that, when loaded to the hydrophobic carrier composition of the present invention and administered to the patient, produces some desired effect at a reasonable benefit/risk ratio applicable to any medical treatment. In certain embodiments, the term refers to that amount necessary or sufficient to eliminate, reduce or maintain (e.g., prevent the spread of) a tumor or other target of a particular therapeutic regimen. The effective amount may vary depending on such factors as the disease or condition being treated, the particular constructs being administered, the size of the subject and/or the severity of the disease or condition. One of ordinary skill in the art may empirically determine the therapeutically effective amount of a particular compound without necessitating undue experimentation. In certain embodiments, the term refers to that amount necessary or sufficient for a use of the subject compositions described herein. In the treatment of insulin-insufficient diabetes, the therapeutically effective amount is the amount of composition of the present invention with corresponding load molecule(s) that will improve glucose homeostasis or normalize blood glucose level of the patient and/or regenerate the beta-islet cells in the pancreas. The regeneration of the beta-islet cells the can be indirectly measured by monitoring blood glucose level, Hemoglobin A1c level, C-peptide level, or insulin level in the blood.

The term "diagnostic" or "diagnostic agent" is any chemical moiety that may be used for diagnosis or imaging a patient. For example, diagnostic agents include imaging agents containing radioisotopes such as indium or technetium; contrasting agents containing iodine, technetium, or gadolinium; enzymes such as horse radish peroxidase, GFP, alkaline phosphatase, or beta-galactosidase; fluorescent substances such as fluorescein, rhodamine and europium derivatives; luminescent substances such as N-methylacrydium derivatives or the like.

The term "alkyl" as used herein refers to a branched or straight chain hydrocarbon of between 4 and 36 carbon atoms, inclusive and can provide non-polar or hydrophobic environment around the carrier. Alkyl, as used herein, is also a portion of a molecule that is a branched or straight chain hydrocarbon of between 4 and 36 carbon atoms, and this portion may be flanked at both ends with nitrogen or oxygen containing moieties as a means of attachment to either the carrier and/or the protective groups.

The term "lower cycloalkyl" as used herein refers to a cyclic hydro carbon of between 4 and 6 carbon atoms, inclusive.

The terms "dissociably linked", "reversibly linked", and "bound", as used herein, refer to a non-covalent bond.

The term "carrier" of the present invention may be any substance capable of supporting hydrophobic groups which in turn can interact with the load molecule. These are substance with plurality of modifiable functional groups. Non-limiting examples of carriers include polymers and co-polymers, microparticles, nanoparticles, and solid surfaces. Microparticle includes particles with diameter of 100 nm or more, whereas nanoparticles are particles with less than 100 nm in diameter. In one aspect, the carrier is biocompatible.

The term "polymeric carrier" as used herein refers to a molecule comprised of several linked chemical moieties which may be the same or different, and serves as a site where a hydrophobic groups and/or protective chains are linked.

The term "non-proteinaceous polyamino acid" as used herein refers to a polyaminoacid that is not naturally made by a living organism unless recombinantly engineered by human. Non-limiting examples of these are poly-(L and/or D)-lysine, poly-(L and/or D)-glutamate, poly-(L and/or D)-glutamate, poly-(L and/or D)-aspartate, poly-(L and/or D)-serine, poly-(L and/or D)-threonine, poly-(L and/or D)-tyrosine, and poly-(L and/or D)-arginine.

The term "protective side chain" as used herein refers to a molecule(s) which protects a carrier molecule, a hydrophobic group, and load molecule from contact with other macromolecules due to extensive linking or binding of water to the chains. Because of this extensive binding with water molecules the protective chain also increases water solubility of the composition. This also means that protective chain provides hydrophilic property to the composition. The term "protective side chain" is used interchangeably with the terms "hydrophilic chain", "protective group" and "protective chain."

The term "aminated" as used herein refers to molecules including linked amino groups.

Introduction

In part, the present invention relates to a composition comprising (i) a carrier, (ii) hydrophobic groups covalently attached to the carrier, (iii) protective side chains covalently attached to the carrier or hydrophobic groups, and (iv) a load molecule bound to the hydrophobic group. By way of a further embodiment, the carrier may optionally contain a targeting molecule covalently attached to the carrier or to the protective side chains. By way of a further embodiment, the carrier may optionally contain an orienting molecule covalently attached to the carrier.

The carrier compositions of the present invention include polymers and co-polymers of linear or branched structure or conjugates thereof, micelles, emulsions, and solid surfaces, where the polymer(s) may self organize in supra molecular structures. The carrier includes a polymeric backbone comprising covalently bound hydrophobic groups where the groups comprise hydrocarbon chains or aromatic compounds. The hydrophobic portion of the carrier and the load molecules interact with each other in aqueous or predominantly aqueous media such as biological fluids. It may be the case that the hydrophobic groups comprise more than one kind of hydrocarbon molecule and/or aromatic molecule covalently attached to the carrier. It may also be the case that the protective groups re-enforce the binding of load molecules to the carrier containing hydrophobic groups. The load molecules bind to the hydrophobic groups in the presence or absence of organic solvents. In one the preferred embodiments the hydrophobic moiety comprises hydrocarbon chains such as, but not limited to, $CH_3(CH_2)_xCO—$, and $C_6H_5(CH_2)_xCO—$, where x is 0-34. Organic solvents that can be used to elute or extract molecules from hydrophobic-core carrier include but are not limited to acetonitrile, methanol, ethanol, and propanol. Higher amounts of organic solvents required to elute load molecules from the carrier is an indication of tight binding. The higher organic solvent required, the tighter the binding.

One embodiment of this invention is a carrier with hydrophobic groups containing phenyl rings. The choice of hydrophobic group linked to the carrier for a specific load molecule will be determined by the hydrophobicity of the load molecule. Globular proteins for examples are globular in water environment because the globular conformation is thermodynamically more stable. This stability is driven by water to keep the hydrophobic portion of the protein to stay away from the surface of the globule which is exposed to water. When globular proteins are exposed to the carrier comprising hydrophobic groups, the globular protein conformation will change to allow the core of the globular protein to interact with the hydrophobic moiety. The larger the globule the more hydrophobic character the proteins contain. Elongated proteins in water environment have less hydrophobic character than the globular proteins. Binding of load molecule to hydrophobic carrier means the ability to be retained by the carrier after washing with at least 100 fold weight equivalent of aqueous solvent. If a carrier with strong binding to the load molecule is desired, larger hydrophobic groups and more of them may be used to modify the carrier. The high affinity binding of load molecules to the carrier comprising hydrophobic groups will maintain low level of free load molecules (i.e. drugs or therapeutic agents) at any given time, and provide a protected reservoir of load molecule (i.e. carrier bound load molecule will be a reservoir). This will reduce the frequency of administration of the therapeutic agent. This is also beneficial for therapeutic agents that require low concentrations to have therapeutic effects and at the same time are toxic at high concentrations. The invention also provides a method of making and using a hydrophobic-core carrier for specific therapeutic compounds.

In one example, a composition of the present invention comprises a linear polyamino acid backbone carrier having a degree of polymerization in the range of 2-10,000 to which are covalently linked methoxypolyethyleneglycol (mPEG) protective chains with a mass of 300-20,000 Da, and hydrophobic groups, wherein the chains and hydrophobic groups are independently linked to the backbone. In another example, the degree of polymerization of the carrier is in the range of 20-1,000. In still another example, the degree of polymerization of the carrier is in the range of 50 to 300. The hydrophobic groups of the present invention may include aromatic compounds and aliphatic groups that may also contain nitrogen and/or oxygen, and may have a charge before linking to the carrier. However, after covalent linking these groups to the carrier backbone polymer, the charge disappears so as to render them hydrophobic. These hydrophobic-core carrier-protective group compositions will bind load molecules with some degree of hydrophobic character. Load molecules added in a purified state will bind to the hydrophobic portion of the carrier to provide a formulation for drug-delivery compositions. This addition or mixing of the hydrophobic-core carrier-protective group complexes with the load molecules can be performed in aqueous solution and optionally followed by lyophilization. Alternatively the mixing can be performed in a mixture of organic solvent and water. The said organic solvents are preferred to be miscible with water. After mixing, the mixture can be dried by evaporation or lyophilization (FIG. 34). The dried mixture can be turned into ready formulation by dissolving in water, buffer, or pharmaceutically acceptable diluents or excipient for administration. Once in the blood or any biological fluid, the load molecules in the composition will be released based on equilibrium association- or dissociation-constants of the load molecules and the hydrophobic-core carrier. The concentration of free load molecule will be maintained as long as there is reservoir of load molecules in the carrier. The expected acceleration of release by blood proteins will be tempered quite significantly by protective groups. In addition the release of protein from the hydrophobic-core carrier can be slow or fast depending on the number and size of the hydrophobic moieties in the carrier.

The association of load molecules with the hydrophobic groups is controlled through the choice of the hydrophobic group. In general, the longer the aliphatic carbon chains, the stronger the association. The affinity of the load molecule for the target receptors on the cells can also be used as a guide for the choice of hydrophobic groups. Ideally the affinity of the load molecule for the hydrophobic group in the carrier should be lower than the affinity of the load molecule for its biological target. In solution, there will be equilibrium between free load molecules and bound load molecules. The carrier with hydrophobic groups will be designed to have free load molecules equal to the desired therapeutic concentrations.

The hydrophobic-core carrier provides drug delivery system that allows significant increase in stability, solubility and distribution of the active molecule.

The hydrophobic-core carrier composition may further include covalently attached targeting molecules to facilitate localization of the carrier to the target tissues and organs and cells in vitro and in vivo. Additionally, the hydrophobic-core carrier composition may further include covalently attached orienting molecules to facilitate better organization of load molecules within the hydrophobic core. Orientation is desired for those load molecules that have specific protease sensitive ends (e.g. Glucagon-Like Peptide has N-terminal that is Dipeptidyl Peptidase IV (DPP-IV) sensitive). The protease sensitive ends can be place closer to the carrier core by placing an orienting molecule along the carrier. This orienting molecule can be a metal ion bridge described in the patent by Bolotin (U.S. Pat. No. 7,138,105), which is hereby incorporated by reference. Additionally, the hydrophobic carrier composition containing load molecules can further comprise a semi-permeable membrane enclosing the entire hydrophobic carrier composition containing load molecules for sub-dermal or oral administration. The semi-permeable membrane may be made up of polymer sheet with pores of sufficient size to allow the load molecule to cross the semi-permeable membrane. Another object of the present invention is to provide a method of making and using the same for the treatment of various diseases.

The hydrophobic-core carrier composition with load molecule may have a size up to several trillion kDa so as to form an extended structure of gel-like composition especially suited for oral, sub-dermal, and topical administrations. Smaller hydrophobic-core carrier composition may also be made so as to form gel. This can be accomplished by making a hydrophobic-core composition with hydrophilic protective chain to hydrophobic group weight ratio of 17 and below. For example a gel will form when a composition with polymeric carrier contains weight ratio of MPEGs (protective chains) to C18 fatty acids (forming the hydrophobic core) of 10. The hydrophobic carrier composition with load molecule may also be made into sheet like structure. This can be done by using a carrier in a form of sheet with modifiable functional groups such as amino, carboxyl, or hydroxyl groups where hydrophobic groups, protective groups, and/or orienting molecules can be attached. This hydrophobic-core carrier sheet with load molecules such as, for example, clotting factor can be used as bandage for treatment of wounds in emergency situation and in battlefields. The composition can be used for treating infections, when the load molecules are anti-infective agents.

Carrier

The carrier of the present invention may be any substance capable of supporting hydrophobic groups which in turn can interact with the load molecule. The carrier of the present invention must have a plurality of derivatizable or modifiable functional groups for the attachment of hydrophobic groups and/or protective chains. Non-limiting examples of carriers include polymers and co-polymers, microparticles, nanoparticles, and solid surfaces. In one aspect, the carrier is biocompatible.

Polymeric and Co-Polymeric Carriers

In certain embodiments, the polymeric or co-polymeric carriers of the subject compositions, e.g., which include repetitive elements shown in any of the subject formulas, have molecular weights ranging from about 500 to about 1,000,000 or more daltons, or alternatively about 5,000; 10,000; 20,000; 30,000; 40,000; or 50,000 daltons, more particularly at least about 100,000 daltons, and even more specifically at least about 250,000 daltons or even at least 500,000 daltons. Number-average molecular weight (Mw) may also vary widely, but generally fall in the range of about 500 to about 200,000 daltons, or even from about 500 to about 100,000 daltons or even from about 500 to about 50,000 daltons. In one embodiment, Mw varies between about 8,000 and 45,000 daltons. Within a given sample of a subject polymer, a wide range of molecular weights may be present. For example, molecules within the sample may have molecular weights which differ by a factor of 2, 5, 10, 20, 50, 100, or more, or which differ from the average molecular weight by a factor of 2, 5, 10, 20, 50, 100, or more.

One method to determine molecular weight is by gel permeation chromatography ("GPC") also known as gel filtration chromatography ("GFC"), e.g., mixed bed columns, $CH_2Cl_2$ solvent, light scattering detector, and offline dn/dc. Other methods are known in the art.

In certain embodiments, the intrinsic viscosities of the polymers generally vary from about 0.01 to about 2.0 dL/g in chloroform at 40° C., alternatively from about 0.01 to about 1.0 dL/g and, occasionally, from about 0.01 to about 0.5 dL/g.

In one embodiment, the carrier may be composed of polyamino acids, preferably non-proteinaceous polyamino acids, polyethyleneimines, natural saccharides, aminated and carboxylated polysaccharides, aminated and carboxylated oligosaccharides, sulfonated polysaccharides, sulfonated oligosaccharides, aminocarboxylated polysaccharides, aminocarboxylated oligosaccharides, carboxymethylated polysaccharides, carboxymethylated oligosaccharides, polyamidoamine, polyacrylic acids, polyalcohols, polyvinyl alcohol, and polythiols. All these carrier polymers have amino, carboxyl, hydroxyl, sulfonate or thiol groups that can be used to attach hydrophobic groups or protective groups essentially altering their properties and allowing them to be both soluble and hydrophobic at the same time.

The carrier may be composed of polymers comprising modifiable functional groups such as, but not limited to polybases, polyalcohols, or polyacids e.g. polylysine, polyserine, polythreonine, polyglycerol, polytyrosine, polyaspartic or polyglutamic acid, or carboxylated polylysine. These reactive or charged functional groups along the backbone are useful since they are capable of forming chemical bonds with the protective- or hydrophobic-groups or derivatives or analogs thereof. These functional groups can also be capped with small hydrophobic groups in order to remove any charge and give the backbone of the carrier a hydrophobic character.

The polyamino acid may be a polymer of a single species, or at least two different species of amino acid, or may be a block co-polymer. The polyamino acid may include but not limited to polyaminoacid fragments linked by cleavable bonds, e.g., S—S bonds. In particular, the polyamino acid may be poly-(L and/or D)-lysine, poly-(L and/or D)-glutamate, poly-(L and/or D)-glutamate, poly-(L and/or D)-aspartate, poly-(L and/or D)-serine, poly-(L and/or D)-threonine, poly-(L and/or D)-tyrosine, poly-(L and/or D)-arginine, or poly-alpha,beta-(2-aminoethyl)-(L and/or D)-aspartamide. All of these polymers have amino, carboxyl, hydroxyl, or thiol groups that can be used to attach hydrophobic groups, protective groups, or orienting molecules allowing them to be both soluble and hydrophobic at the same time. The polyamino acid carrier of the hydrophobic-core carrier composition preferably has 5-560 amino acid units, a molecular weight of 500-100,000 daltons, and is preferably non-proteinaceous.

Examples of aminated polysaccharide or oligosaccharides carrier include but are not limited to polyglucosamine (chitosan), and polygalactosamine.

Examples of carboxylated polysaccharide or oligosaccharides carrier include but are not limited to of polygluronic acid and polygalacturonic acid.

Further examples of polymeric carriers include carboxylated or carboxymethylated linear poly-L-lysine (PL) or poly-D-lysine; carboxylated or carboxymethylated polyalpha,beta-(2-aminoethyl)-D,L-aspartamide; poly-L-aspartic acid; poly-L-glutamic acid, copolymers of histidine with positively or negatively charged amino acids, carboxylated polyethyleneimines, i.e. polyethylene imines reacted with derivatives of carbonic acids; natural saccharides or products chemically derived thereof, bearing carboxylic groups, which may be exemplified by: galacturonic acid, glucuronic acid, mannuronic acid, hyaluronic acid, pectic acid, neuraminic acid, alginic acid, carrageenan; oxidized dextrans; aminated, e.g. containing linked amino groups, polysaccharides or oligosaccharides, linear or branched; poly-carboxylated, carboxymethylated, sulfated or phosphorylated polysaccharides or oligosaccharides, e.g. reacted with derivatives of carbonic, dicarbonic, sulfuric, amino sulfuric, phosphoric acids with resultant linking of carboxylic, amino carboxylic, carboxymethyl, sulfuric, amino or phosphate groups. Such oligosaccharides may be obtained by chemical alteration of, e.g., dextran, mannan, xylan, pullulan, cellulose, chitosan, agarose, fucoidan, galactan, arabinan, fructan, tan, fucan, chitin, pustulan, levan or pectin. In addition these poly- or oligosaccharides may be represented by heteropolymers or homopolymers of monosaccharides such as glucose, galactose, mannose, galactose, deoxyglucose, ribose, deoxyribose, arabinose, fucose, xylose, xylulose, ribulose, polyamidoamine, linear or branched; polyacrylic acid; polyalcohols, e.g. polyvinyl alcohol an polyxylitol, to which carboxylic or amino groups are chemically linked. The molecular weight of a polyaminoacid is preferably larger than 500 and smaller than 100,000. Polyamino acids with narrow molecular weight (MW) distribution are preferred to those with broad MW distribution. Polyaminoacids are prepared by chemical synthesis or by recombinant techniques, such as genetic engineering.

In another embodiment, the polymer acting as the carrier may be poly(ethylene glycol) (PEG) with hydrophobic groups at the far-end making up the site to which the load molecule or the active agent binds. Schematically the embodiment may be represented by the following: PEG-hydrophobic group-load molecule. Alternatively, PEG may be functionalized along its backbone allowing hydrophobic moieties to be pendant to the backbone that would allow binding of load molecule with the pendant hydrophobic moieties. This functionalization may also allow pendant protective chains as well.

In another embodiment, the polymer acting as the carrier may be polyglycerol with poly(ethylene glycol) of the formula HO-PEG-[—$CH_2CH(OH)CH_2O$-]$_n$-PEG-OH where PEG represents poly(ethylene glycol) and n is an integer from 3 to 1000.

For additional examples of polymers suitable for use in the present invention see U.S. Pat. Nos. 6,509,323; 6,492,560; 6,468,532; 6,521,736; 6,348,069; 5,871,710; and 6,051,549 incorporated herein by reference.

Another example of a carrier may be a surface of Stents to form a Drug-Eluting Stents.

Nanoparticles and Microparticles

Examples of nanoparticles and microparticles that can be used as a carrier in the present invention include porous particles having a mass density of less than 1.0 g/cm$^3$, or less than about 0.4 g/cm$^3$. The porous structure permits, for example, deep lung delivery of relatively large diameter therapeutic aerosols, for example greater than 5 microns in mean diameter. These porous particles can be modified to contain hydrophobic groups capable of binding load molecules.

The porous particles preferably are biodegradable and biocompatible, and optionally are capable of biodegrading at a controlled rate for delivery of a drug. The porous particles may be made of any material which is capable of forming a porous particle having a mass density less than about 0.4 g/cm$^3$. Both inorganic and organic materials can be used. For example, ceramics may be used.

The particles may be formed from any bio-compatible, and preferably biodegradable polymer, copolymer, or blend, which is capable of forming porous particles having a density less than about 0.4 g/cm$^3$.

Surface eroding polymers such as polyanhydrides may be used to form the porous particles. For example, polyanhydrides such as poly[(p-carboxyphenoxy)-hexane anhydride] ("PCPH") may be used. Biodegradable polyanhydrides are described, for example, in U.S. Pat. No. 4,857,311.

In another embodiment, bulk eroding polymers such as those based on polyesters including poly(hydroxy acids) can be used. For example, polyglycolic acid ("PGA") or polylactic acid ("PLA") or copolymers thereof may be used to form the porous particles, wherein the polyester has incorporated therein a charged or functionalizable or modifiable group such as an amino acid as described below. This functionalizable group can be modified to contain hydrophobic groups capable of binding load molecules.

Other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, polymers of acrylic and methacrylic acids, celluloses, polysaccharides, and peptides or proteins, or copolymers or blends thereof which are capable of forming porous particles with a mass density less than about 0.4 g/cm$^3$. Polymers may be selected with or modified to have the appropriate stability and degradation rates in vivo for different controlled drug delivery applications.

As another example, the porous particles may be formed from functionalized polyester graft copolymers, as described in Hrkach et al., Macromolecules, 28:4736-4739 (1995); and Hrkach et al., "Poly(L-Lactic acid-co-amino acid) Graft Copolymers: A Class of Functional Biodegradable Biomaterials" in Hydrogel and Biodegradable Polymers for Bioapplications, ACS Symposium Series No. 627, Raphael M. Ottenbrite et al., Eds., American Chemical Society, Chapter 8, pp. 93-101, 1996, the disclosures of which are incorporated herein by reference. The functionalized graft copolymers are copolymers of polyesters, such as poly(glycolic acid) or polylactic acid), and another polymer including functionalizable or ionizable groups, such as a poly(amino acid). In another embodiment, comb-like graft copolymers are used which include a linear polyester backbone having amino acids incorporated therein, and poly(amino acid) side chains which extend from the amino acid groups in the polyester backbone. The polyesters may be polymers of .alpha.-hydroxy acids such as lactic acid, glycolic acid, hydroxybutyric acid and valeric acid, or derivatives or combinations thereof. The inclusion of ionizable side chains, such as polylysine, in the polymer has been found to enable the formation of more highly porous particles, using techniques for making microparticles known in the art, such as solvent evaporation. Other ionizable groups, such as amino or carboxyl groups, may be incorporated, covalently or noncovalently, into the polymer to enhance porosity. For example, polyaniline could be incorporated into the polymer. These groups can be modified further to contain hydrophobic groups capable of binding load molecules.

An exemplary polyester graft copolymer, which may be used to form porous polymeric particles is the graft copolymer, poly(Lactic acid-co-lysine-graft-lysine) ("PLALLys"), which has a polyester backbone consisting of poly(Lactic acid-co-Z-L-lysine) (PLAL), and grafted lysine chains. PLAL-Lys is a comb-like graft copolymer having a backbone composition, for example, of 98 mol % lactic acid and 2 mol % lysine and poly(lysine) side chains extending from the lysine sites of the backbone.

The use of the poly(l acetic acid) copolymer is advantageous since it biodegrades into lactic acid and lysine, which can be processed by the body. The existing backbone lysine groups are used as initiating sites for the growth of poly (amino acid) side chains.

In the synthesis, the graft copolymers may be tailored to optimize different characteristic of the porous particle including: i) hydrophobic interactions between the agent to be delivered and the copolymer to provide stabilization of the agent and retention of activity upon delivery; ii) rate of polymer degradation and, thereby, rate of drug release profiles; iii) surface characteristics and targeting capabilities via chemical modification; and iv) particle porosity. For additional examples of nanoparticles and microparticles suitable for the present invention see U.S. Pat. Nos. 6,447,753 and 6,274,175.

Solid Support

In certain embodiments, the carrier used in the present invention may be a solid support, e.g., a polymer bead or a resin, e.g., a Wang resin. Supports can be solids having a degree of rigidity such as silicon, plastic, and the like. Support can also be flexible materials such as plastic or otherwise synthetic materials (such as nylon), materials made of natural polymers (such as cellulose or silk) or derivatives thereof (such as nitrocellulose) and the like. In certain embodiments the support is a porous material, which can be rigid or flexible, intermeshed fibers including woven fabrics, and the like. In some embodiments, the solid support is a bead or pellet, which can be porous.

The carrier may be made up of a flexible semi-solid polymer. Flexibility is the ability to repeatedly bend and return to its original shape. Carriers made from flexible polymers are adapted for placement in anatomic areas where they will encounter the motion of adjacent organs or body walls. A flexible carrier can thus be sufficiently deformed by moving tissues without causing tissue damage. Flexibility is particularly advantageous for preventing injury where a carrier might be dislodged from its original position. Such a flexible carrier might be suitable for covering pulsatile vessels such as the carotid artery in the neck, or for covering more delicate structures in the neck like the jugular vein that may also be affected by local movements. Similarly, a flexible carrier may be used to protect nerves exposed during a neck dissection such as the spinal accessory nerve, wherein the flexibility of the carrier may permit it to bend or deform when encountering motion rather than eroding into or damaging the nerve. Use of a carrier according to the present invention in the aforementioned ways may allow less extensive dissections to be carried out with surgical preservation of structures important to function. Carriers may be configured as three dimensional structures suitable for implantation in specific anatomic areas. Carriers may be formed as films, meshes, sheets, tubes, or any other shape appropriate to the dimensions and functional requirements of the particular anatomic area. Physical properties of polymers may be adjusted to attain a desirable degree of flexibility by modification of the chemical components and cross-linking thereof, using methods familiar to practitioners of ordinary skill in the art.

A way to create a solid support carrier with reactive sites is to directly derivatize the solid support so that it can be coupled to a compound. The chemistry used to do this can be the same or similar to that used to derivatize controlled pore glass (cpg) beads and polymer beads. Typically, the first step in this process is to create hydroxyl groups (if they do not already exist on the support) or amino groups on the support. If hydroxyl groups exist or are created, they are typically converted to amino groups, for instance by reacting hydroxyl groups with gamma-aminopropyl triethoxy silane. Hydrophobic groups can be added to the amino groups with anhydrides, cyclic acid anhydrides, activated esters, reactions with polymerized alkylene oxides and other methods known to the art.

A method to increase the reactive surface area of a solid support carrier is to create columnar structures of silicon monoxide, for instance by thermal evaporation of SiO. Another such method is to insert into the reaction fabrics, such as non-woven glass or plastic (preferably fiberglass or polypropylene fiber) fabrics and plasma treating the fabric to create reactive sites. Still another method uses spin-on glass, which creates a thin film of nearly stoichiometric SiO from a sil-sesquioxane ladder polymer structure by thermal oxidation. Sol-gel processing creates thin films of glass-like composition from organometallic starting materials by first forming a polymeric organometallic structure in mixed alcohol and then careful drying and baking. When the sol-gel system is dried above the critical temperature and pressure of the solution, an aerogel results. Aerogels have chemical compositions that are similar to glasses (e.g. SiO) but have extremely porous microstructures. Their densities are comparably low, in some cases having only about 1-3% solid composition, the balance being air.

Hydrophobic Groups and Attachment to the Carrier

The type of chemical link to use in attaching the hydrophobic and protective groups will depend on the desired biological half-life of the complex and the therapeutic agent associated with the complex. If a longer half-life is desired, ether or amide bonds will be preferred while ester bonds will be used for carriers with a shorter half-life in biological fluids or tissues. Mixtures of both chemical bonds can be used to achieve the desired stability for a specific load molecule. The S—S bond may also be used to achieve a desired half-life for a specific purpose.

The chemical link may comprise modified amino groups exposed along the carrier or backbone. A modified amino group is the amide linkage of a hydrophobic functional group comprising an alkyl acyl derived from fatty acids, or aromatic alkyl acyl derived from aromatic alkyl acids, which has a general formula [CxHyOz] where x is 2-36; y is 3-71; z is 1-4. It is preferable that z=1, which is the minimum required for amide bond with the amino group. The starting molecules however may have z greater than 1 prior to amide bond formation.

The hydrophobic functional groups may comprise two ended hydrophobic alkyl groups, which have a general formula [—OC(CH$_2$)$_x$CO—] or [—OC(CH$_2$)$_x$CN-] where x is 2-36, and may further comprise a protective group, analog or derivative thereof covalently attached to the other end of the hydrophobic group. In this case the modification of an amino group may be complete where no free amino group remains or the modification may be partial where the extent of modification can be from 50 to 100% more preferably from 90 to 100%. Furthermore, the remaining amino groups can be further modified to contain hydrophobic moieties without protective groups. The resulting composition is also one of the embodiments of this invention.

Another object of the present invention is to provide a method of attaching hydrophobic group to the carrier with amino groups along its length. The modifications can be done by amide bond formation. As an example that is not intended to limit the scope of this invention, the carboxyl containing hydrophobic molecule can be attached to the amino group of the carrier using a carbodiimide containing reagent such a 1-ethyl-3-(3-dimethylaminopropyl)-carbodiimide or dicyclohexylcarbodiimide. A carbodiimide reagent contains a functional group consisting of the formula N=C=N. During the process of coupling reaction, the activated carboxyl group (O-acylisourea-intermediate) can optionally be stabilized by forming N-hydroxysuccinimide ester using N-hydroxysuccinimide. This relatively stable intermediate can react with the amino group of the carrier such as polylysine or chitosan to form amino-acyl bond or amide bond.

Another way to attach a hydrophobic group is to react the carrier amino groups with a fatty acid anhydride. For example, reaction of the carrier amino groups with palmitic acid anhydride forms a long chain hydrophobic group comprising 16 carbons. Any fatty acid anhydride may be used in this fashion.

Another object of the present invention is to provide a method of attaching hydrophobic group to the carrier with carboxyl groups along its length. The modifications can be done by amide bond formation. As an example that is not intended to limit the scope of this invention, the carboxyl group of the carrier can be activated to react with amino functional groups of the hydrophobic groups. The activation can be accomplished using carbodiimide containing reagent such a 1-ethyl-3-(3-dimethylaminopropyl)-carbodiimide or dicyclohexylcarbodiimide. A carbodiimide reagent contains a functional group consisting of the formula N=C=N. During the process of activation, the carboxyl group forms O-acylisourea-intermediate that can optionally be stabilized by N-hydroxysuccinimide to form N-hydroxysuccinimide ester. This relatively stable intermediate can react with the amino group of hydrophobic groups. If the hydrophobic group or molecule does not have an amino group, the amino group can be introduced to this molecule very easily and the chemistry is well known to those skilled in the art.

Another object of the present invention is to provide a method of attaching hydrophobic group to the carrier with hydroxyl group along its length. The modification of hydroxyl group can be facilitated by synthesis of acyl halide of fatty acids, carboxyl aromatic hydrocarbons, or dicarboxylic alkyl. Synthesis of acyl halides can be done by reaction of the carboxylic acid moiety with dichlorosulfoxide ($SOCl_2$) or other reagent known to those skilled in the art. The resulting acyl halides are reactive to alcohols functional group present residue of poly amino acids such as polyserine, polythreonine, and polytyrosine. The reaction will result in an ester bond formation attaching the hydrophobic groups or molecules to the carrier.

Another way to attach a hydrophobic group through forming an ester bond along the length of the carrier is to react the carrier hydroxy groups with a fatty acid anhydride. For example, reaction of the carrier hydroxy groups with palmitic acid anhydride forms a long chain hydrophobic group comprising 16 carbons. Any fatty acid anhydride may be used in this fashion.

The present invention also relates to a hydrophobic-core carrier composition comprising a polymeric carrier or polymeric carrier with protective chains further comprising modified carboxyl groups exposed along the polymer. The modification of the carboxyl groups in the polymeric carrier is the amide covalent attachment of hydrophobic functional groups comprising nitrogen containing hydrocarbon chain or fatty acid ester (or amide) or nitrogen containing aromatic hydrocarbon (which may have an ester or amide bond) which has a general formula [NwCxHyOz] where w is 1-6; x is 2-36; y is 3-74; z is 0-10, where after attachment to the carrier or the backbone, the resulting moiety will have no charge and will be non-polar and thus hydrophobic.

The present invention also relates to a hydrophobic-core carrier composition comprising a polymeric carrier with modified carboxyl groups exposed along the carrier or backbone, wherein the modification of carboxyl groups in the polymeric carrier is the amide covalent attachment of hydrophobic functional groups comprising two ended hydrophobic alkyl groups, which have a general formula [—NC(CH$_2$)$_x$CN-] or [—NC(CH$_2$)$_x$CO—] where x is 2-36, and further comprising a protective group, analog or derivative thereof covalently attached to the other end of hydrophobic group. In this case the modification of amino group along the carrier may be complete where no free amino group remains or partial where the extent of modification can be from 50 to 100%, more preferably from 90 to 100%. Furthermore, the remaining amino groups can be further modified to contain hydrophobic moieties without protective groups. The resulting composition is also one of the embodiments of this invention.

The present invention also relates to a hydrophobic-core carrier composition comprising a polymeric carrier or polymeric carrier with protective chains further comprising modified hydroxyl groups along the polymer. The modification of hydroxyl groups is the ether or ester covalent attachment of hydrophobic functional groups comprising alkyl acyls derived from fatty acids, or aromatic alkyl acyl hydrocarbons derived from aromatic alkyl acids, which have a general formula [CxHyOz] where x is 2-36; y is 3-74; z is 1-10, where after attachment to the carrier or the backbone the resulting moiety will have no charge and will be non-polar and thus hydrophobic.

The present invention also relates to a hydrophobic-core carrier composition comprising a polymeric carrier with modified hydroxyl groups along the carrier or backbone, wherein modification of hydroxy groups in the polymeric carrier is the ester covalent attachment of hydrophobic functional groups comprising two ended hydrophobic alkyl groups, which have a general formula [—OC(CH$_2$)$_x$CO—] or [—OC(CH$_2$)$_x$CN-] where x is 2-36, and further comprising protective group, analog or derivative thereof covalently attached to the other end of hydrophobic group. In this case the modification of hydroxy groups along the carrier may be complete where no free hydroxy group remains or partial where the extent of modification can be from 50 to 100%, more preferably from 90 to 100%. Furthermore, the remaining hydroxy groups can be further modified to contain hydrophobic moieties without protective groups. The resulting composition is also one of the embodiments of this invention.

The present invention also relates to a composition comprising a polymeric carrier or polymeric carrier with protective chains further comprising modified amino groups exposed along the carrier or backbone. The modification of amino groups in the polymeric carrier is amide covalent attachment of hydrophobic functional groups comprising acyl fatty acids, or acyl aromatic hydrocarbons, which have a general formula [NwCxHyOz] where w is 0-6; x is 2-36; y is 3-74; z is 1-10.

The present invention also relates to a composition comprising a polymeric carrier or polymeric carrier with protective chains further comprising modified carboxyl groups exposed along the polymer. The modification of the carboxyl groups in the polymeric carrier is the amide covalent attachment of hydrophobic functional groups comprising nitrogen containing hydrocarbon chains or fatty acid ester (or amide) or nitrogen containing aromatic hydrocarbon (which may have ester or amide bond) which has a general formula [NwCxHyOz] where w is 1-6; x is 2-36; y is 3-74; z is 0-10, where after attachment to the carrier or the backbone the resulting moiety will have no charge. Included as hydrophobic groups are vitamin E, vitamin A, vitamin D, vitamin K, and their analogs or derivatives.

The present invention also relates to a composition comprising a polymeric carrier or polymeric carrier with protective chains further comprising modified hydroxyl groups along the polymer. The modification of hydroxyl groups is the ester covalent attachment of hydrophobic functional groups comprising acyl fatty acids, or acyl aromatic hydrocarbons, which have a general formula [CxHyOz] where x is 2-36; y is 3-74; z is 1-10, where after attachment to the carrier or the backbone the resulting moiety will have no charge.

The present invention also relates to a composition comprising a polymeric carrier with protective chains further comprising unmodified amino groups exposed along the polymer, where the hydrophobic character is provided mainly by the protective chains.

The present invention also relates to a composition comprising a polymeric carrier with protective chains further comprising unmodified carboxyl groups exposed along the polymer, where the hydrophobic character is provided mainly by the protective chains.

The present invention also relates to a composition comprising a polymeric carrier with protective chains further comprising unmodified hydroxyl groups along the polymer, where the hydrophobic character is provided mainly by the protected chains.

The type of chemical link to use in attaching the hydrophobic and protective groups will depend on the desired biological half-life of the complex and the therapeutic agent associated with the complex. If longer half-life is desired amide bonds will be preferred, while ester bonds will be used for carrier that need shorter half-lives or stabilities in biological fluid or tissue. Mixtures of both chemical bonds can be used to achieve the desired stability for a specific therapeutic agent to be delivered. The S—S bond may be used to achieve a desired property of the carrier that would be beneficial for its intended therapeutic and diagnostic purpose.

Load Molecules

The invention also includes hydrophobic-core compositions comprising a load molecule, wherein the load molecule is one of the following: a therapeutic agent or a diagnostic agent. Therapeutic agent load molecules include cytokines, lymphokines, hormones, hormone agonists, hormone antagonists, antibiotics, analgesics, toxins, photo-toxins, cytostatics, cytotoxics, psychotropics, steroidal anti-inflammatory agents, non-steroidal anti-inflammatory agents, immunosuppressive agents, anti-bacterial agents, anti-viral drugs, anti-fungal drugs, chelators, vitamins, protease inhibitors, pesticides, aminoglycosides, polymyxins, ACE inhibitors. These load molecules can be proteins, antibody, antibody fragments, peptides, recombinant peptides, peptides isolated from plants, peptides isolated from fungi, peptides isolated from animals, peptide isolated from bacteria, peptide isolated from viruses, peptides isolated from cells in culture, synthetic peptides, peptidomimetic, organic compounds, synthetic organic compounds, organic compounds isolated from plants, organic compounds isolated from fungi, organic compounds isolated from animals, organic compounds isolated from bacteria, organic compounds isolated from viruses, organic compounds isolated from cells in culture, organometallic compounds, deoxyribonucleic acid, ribonucleic acid, oligonucleotide, other nucleic acid, oligosaccharide, carbohydrates; lipids; photosensitive organic compounds, and proteoglycan.

Non-limiting examples of therapeutic agent load molecules are glucagon-like-peptide, glucagon-like-peptide derivatives, exenatide, glucagon-like-peptide-1, glucagon-like-peptide-2, leptin fragment, Gastric inhibitory polypeptide (GIP), Epidermal Growth Factor (EGF) receptor ligand, EGF, Transforming Growth Factor alpha (TGF-alpha), Betacellulin, Gastrin/Cholecystokinin receptor ligand, Gastrin, Cholecystokinin, lysosthaphin, interferon, interferon gamma, interferon beta (e.g., interferon-beta 1, interferon-beta 2), interferon alpha (e.g., interferon alpha-2a or interferon alpha-2b), interleukin-1, interleukin-2, interleukin-4, interleukin-6, interleukin-8, interleukin-10, interleukin-12, tumor necrosis factor, tumor necrosis factor alpha, tumor necrosis factor beta, auristatin, nisin, insulin, insulin-like growth factor, insulin-like growth factor 1, growth hormone, human growth hormone, growth hormone releasing hormone (GHRH), nerve growth factor, brain-derived neurotrophic factor, enzymes, endostatin, angiostatin, trombospondin, urokinase, streptokinase, blood clotting factor VII, blood clotting factor VIII, granulocyte-macrophage colony-stimulating factor (GM-CSF), granulocyte colony-stimulating factor (G-CSF), thrombopoietin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, epoprostenol, prostacyclin, cyclosporine, vasopressin, terlipressin, desmopressin, cromolyn sodium (sodium or disodium chromoglycate), vasoactive intestinal peptide (VIP), vancomycin, antimicrobials, polymyxin b, anti-fungal agents, anti-viral agents, Fuzeon (enfuvirtide), doxorubicin, etoposide, fentanyl, ketamine, vitamins, daptomycin, ziconotide, teriparatide, Hematide, tissue factor pathway inhibitor (TFPI), desferrioxamine (DFO), oxytocin, cyclosporine, Hematide, tissue factor pathway inhibitor (TFPI), Integrilin (eptifibatide).

The load molecules may also be sulfonamide, such as sulfonamide, sulfamethoxazole and sulfacetamide; trimethoprim, particularly in combination with sulfamethoxazole; a quinoline such as norfloxacin and ciprofloxacin; a beta-lactam compound including a penicillin such as penicillin G, penicillin V, ampicillin, amoxicillin, imipenem, aztreonam, and piperacillin; a cephalosporin such as cephalosporin C, cephalothin, cefoxitin and ceftazidime; a beta lactamase inhibitor such as clavulanic acid; an aminoglycoside such as gentamycin, amikacin, tobramycin, neomycin, kanamycin and netilmicin; a tetracycine such as chlortetracycline and doxycycline; chloramphenicol; a macrolide such as erythromycin; or miscellaneous antibiotics such as clindamycin, a polymyxin, and bacitracin; a polyene antibiotic such as amphotericin B, nystatin, and hamycin; flucytosine; an imidazole or a triazole such as ketoconazole, miconazole, itraconazole and fluconazole; griseofulvin for fungal diseases such as aspergillosis, candidaisis or histoplasmosis; anti-viral drugs such as zidovudine, acyclovir, ganciclovir, vidarabine, idoxuridine, trifluridine, and ribavirin for viral disease; aspirin, phenylbutazone, phenacetin, acetaminophen, ibuprofen, indomethacin, sulindac, piroxicam, diclofenac; gold and steroidal anti-inflammatories for inflammatory diseases such as arthritis; an ACE inhibitor such as captopril, enalapril, lisinopril, quinidine, procainamide, lidocaine, encamide, propranolol, esmolol, bretylium, verapimil and diltiazem for the treatment of cardiac arrhythmia; lovastatin, Lipitor, clofibrate, cholestyramine, probucol, and nicotinic acid for the treatment of hypolipoproteinemias; the organo nitrates such as amyl nitrite, nitroglycerin and isosorbide dinitrate; the calcium channel blockers such as diltiazem, nifedipine and verapamil; the beta adrenergic antagonists such as propranolol for cardiovascular disease; a diuretic such as a thiazide; e.g., benzothiadiazine or a loop diuretic such as furosemide; a sympatholytic agent such as methyldopa, clonidine, gunabenz, guanethidine and reserpine; a vasodilator such as hydralazine and minoxidil; an anthracycline such as doxorubicin, daunorubicin and idarubicin; a covalent DNA binding compound, a covalent DNA binding compound and a platinum compound such as cisplatin and carboplatin; a folate antagonist such as methotrexate and trimetrexate; an antimetabolite and a pyrimidine antagonist such as fluorouracil, 5-fluorouracil and fluorodeoxyuridine; an antimetabolite and a purine antagonist such as mercaptopurine, 6-mercaptopurine and thioguanine; an antimetabolite and a sugar modified analog such as cytarabine and fludarabine; an antimetabolite and a ribonucleotide reductase inhibitor such as hydroxyurea; a covalent DNA binding compound and a nitrogen mustard compound such as cyclophosphamide and ifosfamide; a covalent DNA binding compound and an alkane sulfonate such as busulfane; a nitrosourea such as carmustine; a covalent DNA binding compound and a methylating agent such as procarbazine; a covalent DNA binding compound and an aziridine such as mitomycin; a non covalent DNA binding compound; a non covalent DNA binding compound such as mitoxantrone and, bleomycin; an inhibitor of chromatin function and a topoisomerase inhibitor such as etoposide, teniposide, camptothecin and topotecan; an inhibitor of chromatin function and a microtubule inhibitor such as the *vinca* alkaloids including vincristine, vinblastin, vindisine, and paclitaxel, taxotere or another taxane; a compound affecting endocrine function such as prednisone, prednisolone, tamoxifen, leuprolide, ethinyl estradiol, an antibody such as herceptin; a gene such as the p-53 gene, the p 16 gene, the MIT gene, and the gene E-cadherin, the colony stimulating factors such as granulocyte colony stimulating factor (G-CSF), macrophage colony stimulating factor (M-CSF) and, granulocyte macrophage colony stimulating factor (GM-CSF); all-trans retinoic acid or another retinoid for the treatment of cancer; an immunosuppressive agent such as: cyclosporine, an immune globulin, and sulfasazine, methoxsalen and thalidoimide; insulin and glucagon for insulin-insufficient diabetes; calcitonin and sodium alendronate for treatment of osteoporosis, hypercalcemia and Paget's Disease; morphine and related opioids; meperidine or a congener; methadone or a congener; an opioid antagonist such as nalorphine; a centrally active antitussive agent such as dexthromethrophan; tetrahydrocannabinol or marinol, lidocaine and bupivacaine for pain management; chloropromazine, proclorperazine; a cannabinoid such as tetrahydrocannabinol, a butyrophenone such as droperidol; a benzamide such as metoclopramide for the treatment of nausea and vomiting; heparin, coumarin, streptokinase, tissue plasminogen activator factor (t-PA) as anticoagulant, antithrombolytic or antiplatelet drugs; heparin, sulfasalazine, nicotine and adrenocortical steroids and tumor necrosis factor-alpha for the treatment of inflammatory bowel disease; nicotine for the treatment of smoking addiction; growth hormone, growth hormone releasing hormone (GHRH), leutinizing hormone, corticotropin, and somatotropin for hormonal therapy; and adrenaline for general anaphylaxis.

The load molecules may further include a methylxanthine such as theophylline; cromolyn; a beta-adrenginic agonist such as albuterol and tetrabutaline; a anticholinergic alkaloid such as atropine and ipratropium bromide; adrenocortical steroids such as predisone, beclomethasone and dexamethasone for asthma or inflammatory disease; the anti-bacterial and antifungal agents listed above for anti-bacterial and anti-fungal infections in patients with lung disease (these are the specific diseases listed above in what lung disease includes), in particular this includes the use of aminoglycosides (e.g., amikacin, tobramycin and gentamycin), polymyxins (e.g., polymyxin E, colistin), carboxycillin (ticarcillin) and monobactams for the treatment of gram-negative anti-bacterial infections, for example, in cystic fibrosis patients, for the treatment of gram negative infections of patients with tuberculosis, for the treatment of gram negative infections in patients with chronic bronchitis and bronchiectasis, and for the treatment of gram negative infections in generally immuno-compromised patients; the use of pentamidine for the treatment of patients (e.g., HIV/AIDS patients) with Pneumocytis *carinii* infections; the use of a polyene antibiotic such as amphotericin B, nystatin, and hamycin; flucytosine; an imidazole or a triazole such as ketoconazole, miconazole, itraconazole and fluconazole; griseofulvin for the treatment of such fungal infections as aspergillosis, candidiasis and histoplasmosis, particularly those originating or disseminating to the lungs; the use of the corticosteroids and other steroids as listed above, as well as nonsteroidal anti-inflammatory drugs for the treatment of anti-inflammatory conditions in patients with lung disease (these are the specific diseases listed above in what lung disease includes); DNase, amiloride, CFTRcDNA in the treatment of cystic fibrosis; alpha-1-antitrypsin and alpha-1-antitrypsin cDNA for the treatment of emphysema; an aminoglycoside such as amikacin, tobramycin or gentamycin, isoniazid, ethambutol, rifampin and its analogs for the treatment of tuberculosis or *mycobacterium* infections; ribavirin for the treatment of respiratory syncitial virus; the use of the anticancer agents listed above for lung cancer in particular cisplatin, carboplatin, and taxanes such as paclitaxel, and the taxanes, camptothecin, topotecin, and other camptothecins, herceptin, the p-53 gene.

The biologically active therapeutic agents suitable for use as load molecules in the present invention include compounds which by themselves do not pass (or which pass only a fraction of the administered dose) through the gastrointestinal mucosa and/or are susceptible to chemical and/or enzymatic cleavage by acids and enzymes in the gastrointestinal tract; or any combination thereof. These include proteins, polypeptides; peptides; hormones; polysaccharides, and particularly muco-polysaccharides and mixtures thereof.

In a further embodiment, the present invention relates to the above described composition wherein more than one type of load molecule is bound to the hydrophobic group of the polymeric carrier.

In a further embodiment, the present invention relates to the above described composition wherein the load molecule is a diagnostic agent. These include fluorescent molecules, paramagnetic molecules, and radioactive molecules.

Yet another object of the present invention is to provide a method of loading the a hydrophobic-core carrier composition of the invention with load molecule by mixing sufficient amount of load molecule and the hydrophobic-core carrier in suitable solvent and optionally co-lyophilizing both the load molecule and the hydrophobic-core carrier. Sufficient amount of load molecule may vary depending on the load molecule but preferably between 1 to 400% of the weight of the hydrophobic-core carrier.

It is the intention of the present invention to provide a method of treatment of various diseases described in the "The Merk Manual of Diagnosis and Therapy" (published 1992 by Merck Laboratories which is a division of Merck & Co., Inc, Rahway, N.J.) using compositions described in the present invention along with appropriate load molecule selected from that described in PDR or Physician Desk Reference (published 2001 by Medical Economics Company, Inc. Montvale, N.J.). The Merk Manual of Diagnosis and Therapy and the PDR are hereby incorporated by reference. The appropriateness of a load molecule for particular disease can be ascertained by checking "The Merk Manual of Diagnosis and Therapy" or the PDR.

Protective Chains or Groups

The subject hydrophobic-core carrier compositions, and methods of making and using the same, may achieve a number of desirable results and features provided by the protective chains, one or more of which (if any) may be present in any particular embodiment of the present invention. The protective chain of the composition is preferably a polymer of ethylene oxide (poly(ethylene glycol), i.e. PEG or a mono-methoxy ether of poly(ethylene glycol) i.e. MPEG. A protective chain is useful because: 1) it ensures the solubility the composition while maintaining a high drug payload, for example, with GLP-1, at least 30% by weight was loaded into the carrier before a decrease in solubility was observed; 2) a protective chain assists in the formation of a steric barrier which can prevent load molecules (peptides, proteins and other therapeutic agents) from binding or interaction with other macromolecules, enzymes and cells in the body; 3) a protective chain provides load molecules (peptides and proteins and drugs) with long circulation times or biological half-lives in vivo (e.g. for decreasing glomerular filtration in kidneys, decreasing kidney and liver uptake, decreasing macrophage uptake . . . etc.) and creates a circulating depot; 4) a protective chain decreases undesirable immunogenicity of the carrier or its load molecules such as a peptide or protein drug; 5) the abnormal permeability of tumor vessels assists accumulation of the carrier with load molecules in a tumor or inflammation site by delivering the load molecules or anti tumor compounds to the tumor which is especially useful for treating tumors; 6) a protective chain may also provide additional binding strength; and 7) a protective chain may provide binding to the surface, such as to a mucosal surface by interaction with mucosa.

The protective chain of the hydrophobic-core carrier composition may be, e.g., polyethylene glycol, methoxypolyethylene glycol, methoxypolypropylene glycol, a co-polymer of polyethylene glycol, methoxypolyethylene glycol, or methoxypolypropyleneglycol, or derivatives thereof. In addition, the protective chain may be a block co-polymer of polyethyleneglycol and one of the group of polyamino acids, polysaccharides, polyamidoamines, polyethyleneamines, or polynucleotides. The protective chain may also be a co-polymer of polyethylene glycol including a monoester of a dicarboxylic acid. The protective chain may also be a sialic acid chain. The protective chain preferably has a molecular weight of 500-10,000 daltons.

In another related aspect, the hydrophobic-core carrier composition includes a protective chain which is polyethylene glycol, polypropylene glycol, a co-polymer of polyethylene glycol and polypropylene glycol; or a alkoxy derivative thereof, preferably methoxypolyethylene glycol, methoxypolypropylene glycol, or a co-polymer of methoxypolyethylene glycol and methoxypolypropyleneglycol; the protective chain may be polyethylene glycol monoamine, methoxypolyethylene glycol monoamine, methoxy polyethylene glycol hydrazine, methoxy polyethylene glycol imidazolide or a polyethylene glycol diacid; the protective chain is a block co-polymer of polyethylene glycol and one of the group of polyamino acids, polysaccharides, alkoxylated polysaccharides, polyamidoamines, polyethyleneamines, or polynucleotides; the protective chain may be a co-polymer of polyethylene glycol comprising a monoester of a dicarboxylic acid; and the protective chain has a molecular weight of 500-10,000 daltons.

Further examples of protective chains include methoxy polyethylene glycol) imidazolide block-copolymer of poly (ethylene glycol) and one or several polymers represented by polyaminoacid, poly-lactideglycolide co-polymer, polysaccharide, polyamidoamine, polyethyleneimine or polynucleotide (see polymeric carrier) where these blocks are preferably alternated to give a preferably linear block-copolymer. Overall molecular weight of a protective chain is preferentially larger than 300 but preferably not exceeding 10,000. A protective chain or chains are linked to the polymeric carrier by preferably a single linkage.

Modification of Amino Groups of the Carriers to Attach the Protective Chains

The present invention also relates to a hydrophobic-core carrier composition comprising a polymeric carrier or polymeric carrier with hydrophobic group or molecule further comprising modified amino groups exposed along the polymer. A non-limiting example of an amino group modification along the polymeric carrier is amide attachment of protective chains comprising acyl polymethoxyoxyethyleneglycol. An example of a protective chain which is not intended to limit the scope of this invention is an acyl PEG, analog or derivative thereof which can be represented by formula: $-CO(CH_2)_nCOOCH_2CH_2\text{-}A\text{-}OR_3$ or $-COCH_2\text{-}A\text{-}OR_3$, where n is 2-22; A is $[OCH_2CH_2]_x$ or $[OCH_2CH_2]_x$ or $[OCHCH_3CH_2]_x$, where x is 17-250, or various combinations of $[OCH_2CH_2]$, $[OCH_2CH_2]$, and/or $[OCHCH_3CH_2]$ with total of 17-250 units, $R_3$ is H, $(CH_2)_pCH_3$ or $(CH_2)_pCOOH$, and p is 0-7.

The present invention also relates to a hydrophobic-core carrier composition comprising a polymeric carrier or polymeric carrier with hydrophobic groups that has modified amino groups along the polymer. In a further embodiment, the present invention relates to the above described composition wherein the carrier comprises protective side chains. In a further embodiment, the protective side chain comprises poly(ethylene glycol). In a further embodiment, the protective side chain comprises alkoxy poly(ethylene glycol). In a further embodiment, the protective side chain comprises methoxy poly(ethylene glycol) (MPEG). In a further embodiment, the protective side chain comprises polysialic acid. In a further embodiment, the protective side chain comprises poly(acrylamide). In a further embodiment, the protective side chain comprises poly(vinylpyrrolidone). These can be attached to the polymeric carrier using any of the chemical bonds mentioned above.

Another object of the present invention is to provide a method of attaching protective chains to the carrier. The modifications can be done by amide bond formation. As an example that is not intended to limit the scope of this invention, the carboxyl containing protective molecule can be attached to the amino group of the carrier using carbodiimide containing reagent such a 1-ethyl-3-(3-dimethylaminopropyl)-carbodiimide or dicyclohexylcarbodiimide. A carbodiimide reagent contains a functional group consisting of the formula N=C=N. During the process of coupling reaction, the activated carboxyl group O-acylisourea-intermediate can be stabilized by forming N-hydroxysuccinimide ester using N-hydroxysuccinimide. This relatively stable intermediate can react with the amino group of carrier such as polylysine or chitosan to form amino-acyl bond or amide bond. Similar result can also be accomplished by reacting aldehyde containing protective group to the amino group along the carrier. The aldehyde can react with the amino group of carrier such as polylysine or chitosan to form amino-acyl bond or amide bond.

Modification of Carboxyl Groups of the Carriers to Attach the Protective Chains

The present invention also relates to a hydrophobic-core carrier composition comprising a polymeric carrier or polymeric carrier with hydrophobic group or molecule further comprising modified carboxyl groups exposed along the polymer. The modification of the carboxyl groups in the polymeric carrier is the amide covalent attachment of an amino group containing protective chains comprising amino polymethoxyoxyethyleneglycol. As an example that is not intended to limit the scope of this invention, the protective chain can be an amino PEG which can be represented by formula —NH$(CH_2)_n$NHCOCH$_2$-A-OR$_3$, —NH$(CH_2)_n$NHCO$(CH_2)_n$COOCH$_2$CH$_2$-A-OR$_3$, where n is 2-22; A is [OCH$_2$CH$_2$]$_x$ or [OCH$_2$CH$_2$]$_x$ or [OCHCH$_3$CH$_2$]$_x$, where x is 17-250, or various combinations of [OCH$_2$CH$_2$], [OCH$_2$CH$_2$], and/or [OCHCH$_3$CH$_2$] with total of 17-250 units, R$_3$ is H, $(CH_2)_p CH_3$ or $(CH_2)_p COOH$, and p is 0-7.

The present invention also relates to a hydrophobic-core carrier composition comprising a polymeric carrier or polymeric carrier with hydrophobic groups that has modified carboxyl groups along the polymer. In a further embodiment, the present invention relates to the above described composition wherein the carrier comprises protective side chains. In a further embodiment, the protective side chain comprises poly(ethylene glycol). In a further embodiment, the protective side chain comprises alkoxy poly(ethylene glycol). In a further embodiment, the protective side chain comprises methoxy poly(ethylene glycol) (MPEG). In a further embodiment, the protective side chain comprises polysialic acid. In a further embodiment, the protective side chain comprises poly(acrylamide). In a further embodiment, the protective side chain comprises poly(vinylpyrrolidone). These can be attached to the polymeric carrier using any of the chemical bonds mentioned above.

Another object of the present invention is to provide methods of attaching protective chains to the carrier. These modifications can be done by amide bond formation. As an example that is not intended to limit the scope of this invention, the carboxyl group of the carrier can be activated to react with amino functional group of the protective molecules. The activation can be accomplished using carbodiimide containing reagent such a 1-ethyl-3-(3-dimethylaminopropyl)-carbodiimide or dicyclohexylcarbodiimide. A carbodiimide reagent contains a functional group consisting of the formula N.dbd.C.dbd.N. During the process of activation the carboxyl group forms O-acylisourea-intermediate that can be stabilized by N-hydroxysuccinimide to form N-hydroxysuccinimide ester. This relatively stable intermediate can react with the aminogroup of protective molecules. If the protective group or molecule that needs to be introduced into the carrier does not have amino group, the amino group can be introduced to this molecule very easily and this process is well known to those skilled in the art.

Modification of Hydroxyl Groups of the Carriers to Attach the Protective Chains

The present invention also relates to a hydrophobic-core carrier composition comprising a polymeric carrier or polymeric carrier with hydrophobic group or molecule further comprising modified hydroxyl groups along the polymer. The modification of hydroxyl groups includes ester attachment of protective groups or molecules comprising acyl polymethoxyoxyethyleneglycol. As an example that is not intended to limit the scope of this invention, the protective group can be a PEG with acyl or carbonyl represented by CO and attached to O of hydroxyl group of carrier to form ester. The acyl PEG or its derivative can be represented by formula —CO$(CH_2)_n$NHCOCH$_2$-A-OR$_3$, COCH$_2$CH$_2$-A-OR$_3$, or COCH$_2$-A-OR$_3$, where n is 2-22; A is [OCH$_2$CH$_2$]$_x$ or [OCH$_2$CH$_2$]$_x$ or [OCHCH$_3$CH$_2$]$_x$, where x is 17-250, or various combinations of [OCH$_2$CH$_2$], [OCH$_2$CH$_2$], and/or [OCHCH$_3$CH$_2$] with total of 17-250 units, R$_3$ is H, $(CH_2)_p CH_3$ or $(CH_2)_p COOH$, and p is 0-7.

The present invention also relates to a hydrophobic-core carrier composition comprising a polymeric carrier or polymeric carrier with hydrophobic groups that has modified hydroxyl groups along the polymer. In a further embodiment, the present invention relates to the above described composition wherein the carrier comprises protective side chains. In a further embodiment, the protective side chain comprises poly(ethylene glycol). In a further embodiment, the protective side chain comprises alkoxy poly(ethylene glycol). In a further embodiment, the protective side chain comprises methoxy poly(ethylene glycol) (MPEG). In a further embodiment, the protective side chain comprises polysialic acid. In a further embodiment, the protective side chain comprises poly(acrylamide). In a further embodiment, the protective side chain comprises poly(vinylpyrrolidone). These can be attached to the polymeric carrier using any of the chemical bonds mentioned above.

Another object of the present invention is to provide methods of attaching protective chains to the carrier. The modification of hydroxyl group can be facilitated by synthesis of acyl halides of protective molecules. Synthesis of acyl halides can be done by reaction of the carboxylic acid moiety of protective molecules with dichlorosufoxide (SOCl$_2$) or other reagent known to those skilled in the art. The resulting acyl halides are reactive to alcohols including serine, threonine, and tyrosine residue of poly amino acids. The reaction will result in an ester bond formation essentially attaching the protective groups or molecules into the carrier. PEG-epoxide, PEG-isocyanate, PEG-PNC (PEG-nitrophenylcarboxyester) are the PEG analogs that may be used to modify the hydroxyl groups forming ether, ester, and urethane linkage respectively between protective group and the carrier.

Orienting Molecules

Yet another object of the present invention is to provide a hydrophobic-core carrier comprising hydrophobic groups covalently attached to a carrier or to the carrier and protective groups, a load molecule bound to the hydrophobic molecule by hydrophobic interaction, and an orienting molecule covalently attached to the carrier and bound to the load molecule to orient or position the load molecule within the hydrophobic groups. The orienting molecule can be a receptor or a peptide that recognizes the load molecule or it could be a complex comprising a metal ion bridge described by Bolotin (pub. NO.: US 200310224974 A1) and hereby incorporated by reference. A metal ion bridge comprises a carrier with a first metal binding domain coordinated to a metal ion. The metal ion is further coordinated to the load molecule through a second metal binding domain. The orienting molecule may also be an amino or carboxyl moiety covalently anchored to the polymeric carrier. The orienting molecule can also be positively charged or negatively charged such as a molecule containing sulfate, sulfonate, phosphate, phosphonate, or bis phosphonate, or nitrogen containing compounds such as lysine, arginine, and histidine to mention a few non-limiting examples.

Targeting Molecules

Yet another object of the present invention is to provide a pharmaceutical composition comprising hydrophobic groups covalently attached to a carrier or to the carrier and protective groups, a load molecule bound to the hydrophobic molecule by hydrophobic interaction, and a targeting molecule to facilitate the localization of the pharmaceutical composition to the tissue of interest.

The targeting group may be linked to the polymeric carrier or the protective chain or both. The targeting group may be an antibody, fragment of an antibody, chimeric antibody, where the antibodies are polyclonal or monoclonal; peptides; enzymes; quasi substrates of enzymes; lectins; or saccharide ligands of lectins detachably or non-detachably linked to the composition, enzyme, lectin, saccharide ligand, or peptide fragment.

The role of a targeting moiety is to place the compositions of the present invention in close proximity to a target within a patient's body. In this manner, it is envisioned that the present invention can optionally utilize a targeting agent or molecule.

Examples of targeting moieties include: (i) chemotactic proteins and peptides including monocyte chemotactic protein 1 (MCP-I), N-formyl-methionyl-leucyl-phenylalanine; (ii) colony stimulating factors including GM-CSF, CSF-1, and receptors and antibodies thereto; and platelet factor 4; (iii) growth factors including TGF-fl and VEGF; (v) adhesive cell-surface glycoproteins including E-selectin, VCAM-1, and VCAM1fl; (iv) carbohydrates including llC-deoxy-D-glucose, and IsF-2-fluorodeoxy-D-glucose; (vi) components of a vascular inflammatory response including C1, C1q, C1r, C1s, C2, C3, C3a, C3b, C4, C4C2, C4C2C3b, C5a, C5b and C5a; (vii) interleukins including IL-1, IL-1a, IL-10, IL-2, IL-3, IL-6, IL-7, and IL-8; (viii) interferons including interferon a and interferon y; (ix) tumor necrosis factor TNF-α; and (x) lipids including liposomes, polyethylene glycol coated liposomes, cholesterol, esters of cholesterol, lipoproteins including LDL, HDL, oxidized LDL, and lipid receptors.

The Hydrophobic-Core Carrier Composition

Figure 1:
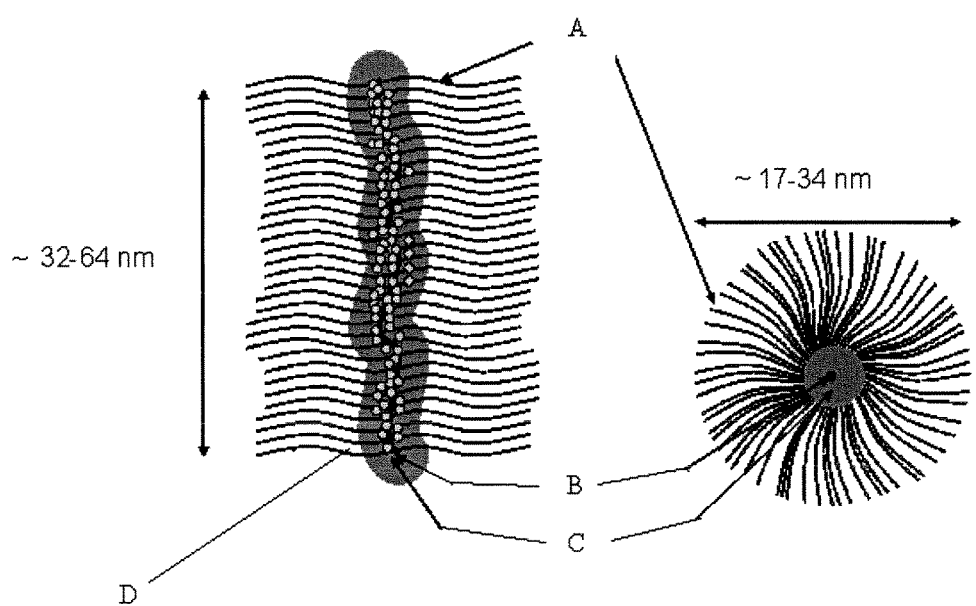
FIG. 1 depicts a schematic representation of one embodiment of the hydrophobic-core composition of the invention: A) protective side chains; B) polymeric core (dark); C) hydrophobic chains (gray); and D) space between the protective side chains at the base closer to the carrier is at least 9 nm because of a 360 degree distribution, there is 1 protective side chain per 6 polymeric residues of the core depicted. Small circles represent load molecules. For example: albumin hydrated (diameter=7.2 nm); growth hormone hydrated (diameter=3 nm); glomerular filtration diameter <4 nm; beta-2 macroglobulin (diameter=3.2 nm); myoglobin (diameter=3.9 nm); hemoglobin (diameter=6.5 nm); gamma globulin (diameter=11.1 nm); and Bence-Jones protein (diameter=5.5 nm).

One embodiment of the hydrophobic-core carrier compositions with load molecules is represented in FIG. 1. This representation is not intended to limit the scope of the invention but rather to show some important features of the invention. The scale of the sizes of the components of the hydrophobic-core carrier composition and load molecules are estimated based on the length of chemical bond present in the composition.

In this representation, the load molecules will be adsorbed into the hydrophobic portion of the composition and will be protected by the linear protective chains radiating from the carrier. The protective chains may be attached independently to the carrier or may be attached to the end of the hydrophobic molecule. In the former, the protective chain may be attached to the carrier in various ways, preferably by amide bond or ester bond. In the latter, the protective chain may be attached to the hydrophobic group, preferably to the terminal portion of the hydrophobic group. The hydrophobic group is further attached to the carrier preferably by an amide or ester bond. The load molecules are reversibly bound to the hydrophobic portion of the hydrophobic-core carrier by hydrophobic interaction which can be strengthened in aqueous environments. The loading of load molecules to the hydrophobic-core carrier can be accomplished by simply mixing the load molecule with the hydrophobic-core carrier in the ratio of hydrophobic-core carrier to load molecule of between about 1:0.1 to 1:10; weight to weight. The mixing is preferably done in water or phosphate buffered saline depending on the properties of the load molecule, followed optionally by lyophilization. Other excipients can optionally be added to the complex to control pH, tonicity, and viscosity. The hydrophobic-core carrier-load molecule complex can be lyophilized in portions of known amounts for administration to a patient needing treatment with the particular load molecule in the complex. The lyophilized complex can be reconstituted in saline or water for administration to patient to treat diseases such as, for example, insulin-insufficient diabetes, vascular diseases, heart diseases, stroke, blood clot in the vessel, cancers, cancer of the liver, cancer of the kidney, cancer of the colon, cancer of the pancreas, cancer of the lung, cancer of endocrine glands, pituitary tumor, soft tissue tumor, cancer of the tongue, cancer of the bone, leukemia, melanoma, lymphomas, Hodgkin lymphoma, non-Hodgkin lymphoma, hepatitis, hepatitis A, hepatitis B, hepatitis non-A non-B, hepatitis C, Alzheimer's disease, Parkinson's disease, psychiatric disorders, schizophrenia, bipolar disorder, endocrine disorder, hypertension, hypotension, clotting factor deficiency, parasitic diseases, fungal infection, bacterial infection, staphylococcal infection, *bacillus* infection, necrotizing infection, gangrene, poisoning, poisoning with bacterial toxins, and poisoning with venom. The diseases that can be treated using hydrophobic-core carrier-load molecule complex of the present invention include various diseases described in the "The Merk Manual of Diagnosis and Therapy" (published 1992 by Merck Laboratories which is a division of Merck & Co., Inc, Rahway, N.J.) wherein the choices of appropriate load molecule is dictated by PDR or Physician Desk Reference (published 2001 by Medical Economics Company, Inc. Montvale, N.J.). The disclosure on "The Merk Manual of Diagnosis and Therapy" and the "PDR" are hereby incorporated by reference. The appropriateness of a load molecule for particular disease can be ascertained by checking "The Merk Manual of Diagnosis and Therapy" or the PDR.

The affinity of load molecules to the hydrophobic-core carrier can be adjusted by changing the length of the hydrophobic chains, adjusting the size of the aromatic groups, adjusting the number of hydrophobic chains, or by adjusting the number aromatic groups. The hydrophobic-core carrier of the present invention can have a protective chain for every hydrophobic group resulting in a hydrophobic group every 0.3 nm. If there are less protective groups (one protective group per two or more hydrophobic groups) a distance of 0.15 nm between every hydrophobic group can be achieved, which is quite high. Since each hydrophobic group can have between 2 to 36 carbon chains, inclusive, the carbon loading that determines the binding of load molecules to the hydrophobic-core carrier can be very high if desired. High affinity hydrophobic-core carriers can be design by increasing the density of hydrophobic groups attached to the carrier. The maximum can be achieved by placing long chain hydrophobic groups on all of the available sites on the polymeric carrier and since there will be no site left for the protective group, the protective groups will be attached to the terminal ends of the hydrophobic groups.

This can be achieved by attaching one end of any one of the following molecules: butenedionic (HOOC(CH$_2$)$_2$COOH), pentanedioic acid (HOOC(CH$_2$)$_3$COOH), hexanedioic acid (HOOC(CH$_2$)$_4$COOH), heptanedioic acid (HOOC(CH$_2$)$_5$COOH), octanedioic acid (HOOC(CH$_2$)$_6$COOH), nonanedioic acid (HOOC(CH$_2$)$_7$COOH), decanedioic acid (HOOC(CH$_2$)$_8$COOH), undecanedioic acid (HOOC(CH$_2$)$_9$COOH), dodecanedioic acid (HOOC(CH$_2$)$_{10}$COOH), undecanedioic acid (HOOC(CH$_2$)$_{11}$COOH), dodecanedioic acid (HOOC(CH$_2$)$_{12}$COOH), (HOOC(CH$_2$)$_{13}$COOH), (HOOC(CH$_2$)$_{14}$COOH), (HOOC(CHCH$_2$)$_{15}$COOH), (HOOC(CH$_2$)$_{16}$COOH), (HOOC(CH$_2$)$_{17}$COOH), (HOOC(CH$_2$)$_{18}$COOH), (HOOC(CH$_2$)$_{19}$COOH), (HOOC(CHCH$_2$)$_{20}$COOH), (HOOC(CH$_2$)$_{21}$COOH), or (HOOC(CH$_2$)$_{22}$COOH), (HOOC(CH$_2$)$_{23}$COOH), (HOOC(CH$_2$)$_{24}$COOH), (HOOC(CH$_2$)$_{25}$COOH), (HOOC(CH$_2$)$_{26}$COOH), (HOOC(CH$_2$)$_{27}$COOH), (HOOC(CH$_2$)$_{28}$COOH), (HOOC(CH$_2$)$_{29}$COOH), (HOOC(CH$_2$)$_{30}$COOH), (HOOC(CH$_2$)$_{31}$COOH), (HOOC(CH$_2$)$_{32}$COOH), (HOOC(CH$_2$)$_{33}$COOH), or (HOOC(CH$_2$)$_{34}$COOH) to the carrier and the other end to any of the aminated PEG derivatives or analogs. This can be done using reaction outlined in FIG. 2. Excess of the diacid should be used during modification of the polyaminogroups to prevent both ends of the diacid from reacting with the polyamino carrier. Un-reacted diacid should be removed before the addition of aminated PEG, analog, or derivative thereof. At both ends of the dicarboxylic hydrophobic molecule, amide bonds will be formed wherein one end is attached to the carrier and the other end attached to the protective group. A similar process can be achieved using diaminoalkanes as hydrophobic groups such as H$_2$N(CH$_2$)$_x$NH$_2$, where x is 4-36. Diaminoalkanes can be attached to a carrier containing carboxyl groups using the reaction in FIG. 2. Alternatively, heterobifunctional hydrophobic moieties such as HOOC(CH$_2$)$_x$NH$_2$, where x is 4-36, can be used to avoid potential side reactions of both ends of the hydrophobic group to the carrier. If this reagent is used, a polyglutamic or polyaspartic acid carrier can be used in pre-activated form. Pre-activation of the carrier with carboxyl groups can be done as in FIG. 2. Excess activating reagent can be removed by filtration or gel filtration chromatography prior to reaction with the heterobifunctional hydrophobic groups such as HOOC(CH$_2$)$_x$NH$_2$, where x is 4-36. Membrane filtration and gel filtration chromatography for removing activating agents are known to those skilled in the art. Any of the heterobifunctional hydrophobic moieties above can be added to the pre-activated carrier allowing formation of amide bonds between the amino groups and the carboxyl groups of the carrier such as polyglutamic or polyaspartic acid. The reaction mixture can then be filtered again to remove excess heterobifunctional hydrophobic moieties. The carboxyl group of the attached hydrophobic moiety can then be activated (in a similar manner to the activation of the carrier) and once activated, the amino group containing protective group analog or derivative can then be added to allow amide bond formation. The resulting product will have a high density of hydrophobic groups around the carrier. The longer hydrophobic chains provide very high density and volume of hydrophobic groups around the carrier. The density can further be increased by attaching moieties to the carrier that will increase the number of modifiable functional groups (such as amino or carboxyl groups) along the carrier and doing the same process as described above. Furthermore, a branched hydrophobic molecule can be used to modify the carrier such that there will be two hydrophobic chains attached per modifiable functional group in the carrier. If the affinity is too high for the desired load molecule, shorter hydrophobic chains can be used and the density can be reduced. Using shorter hydrophobic groups and decreasing the density will decrease the affinity of the hydrophobic-core carrier to the load molecule. The preferred hydrophobic groups are the linear chains derived from fatty acids because they are non-toxic and easily metabolized in the body. They are also non-immunogenic.

Another way to attach a hydrophobic group through forming an amide bond along the length of the carrier is to react the carrier amino groups with a fatty acid anhydride. For example, reaction of the carrier amino groups with palmitic acid anhydride forms a long chain hydrophobic group comprising 16 carbons. Any fatty acid anhydride may be used in this fashion.

If a lower affinity hydrophobic-core carrier is desired, the density of hydrophobic groups can be further reduced by attaching the protective groups independently of the hydrophobic group. Using this approach the number of site along the carrier populated by the hydrophobic group can vary from 10% to 80% inclusive and the length of the hydrophobic group can vary from 2 carbons to 14 carbons, inclusive.

There has been a long felt need to have a drug or therapeutic drug delivery system that has properties such as protection from degradation, slow release, and control of the amount that is free at any given time. The amount of drug that is free will be determined by a binding equilibrium defined by the dissociation constant of the carrier to the load molecule. The dissociation constant can be determined between a specific load molecule and a carrier with a defined composition.

Determination of Dissociation Constant Between the Hydrophobic-Core Carrier and the Load Molecule.

To determine the dissociation constant for hydrophobic-core carriers with a molecular weight greater than 100 kDa, place 100 ul aliquots of hydrophobic-core carrier (1 mg/ml in phosphate buffered saline, PBS; 50 mM Phosphate, 150 mM NaCl, pH 7.4) in 10 tubes in triplicate. As controls, prepare another set of 10 tubes in triplicate without hydrophobic-core carrier but with 100 ul of PBS. Place triplicate-100 ul-aliquots of 1000 nM, 500 nM, 100 nM, 50 nM, 10 nM, 5 nM, 1 nM, 0.5 nM, 0.1 nM, and 0 nM solution of load molecule dissolved in phosphate buffered saline into all the tubes including controls. Mix by vortex and incubate the solution for 1 hr at 37° C., followed by lyophilization. Reconstitute the dried samples in 200 ul distilled deionized water, filter all the solution through a 100 kDa cut-off membrane (from Millipore, Bedford, Mass.) by centrifugation. The load molecules that go through the filter are the concentration of free load molecule in solution. The control tubes without the hydrophobic-core carrier will be the total amount of load molecules available for binding. The bound load molecules can be calculated by subtracting the free from the corresponding control that received the same concentration of load molecules but without the hydrophobic-core carrier. Graph the bound/free load molecules along the y-axis against bound load molecule (nM) along the x-axis. The slope of the graph of bound/free on the Y axis and bound (nM) x-axis will be the −1/Kd where Kd is the dissociation constant. The quantification of load molecules that went through the filter can be done by means such as Elisa (Enzyme link immunosorbent assay), HPLC, or HPLC/MS.

Maintenance of Free Load Molecule Concentration

The free load molecule concentration over time can be predicted from the equilibrium constant between the free load molecule and load molecule bound to the hydrophobic-core carrier. This can be determined in an isotonic saline solution. The equilibrium constant can be adjusted by changing the size and amount of hydrophobic moieties within the carrier and the size and amount of protective groups. The smaller the size and amount of hydrophobic moieties, the higher free load molecule concentration at any given time up until the load molecule reservoir is depleted. The larger the size and amount of hydrophobic moieties, the lower the free load molecule concentration at any given time up until the load molecule reservoir is depleted. In the latter scenario, the reservoir will take longer to deplete and the release of load molecule will be prolonged. Such a release profile may result in prolonged delivery if preferred (over, say 3 to about 4,000 hours, or alternatively about 10 to about 1500 hours) of effective amounts (e.g., about 0.00001 mg/kg/hour to about 10 mg/kg/hour) of the load molecule or any other material associated with the biocompatible composition. It should be noted that the hydrophobic-core carrier and the load molecule will have affinity for each other which can be defined by an affinity constant (Ka) or dissociation constant (Kd). This affinity can be adjusted by changing the size and amount of hydrophobic moieties within the carrier. Since Kd or Ka represents an equilibrium constant, they define the amount of free load molecule at any given time. If the concentration of free load molecule decreases, due to utilization by the body, there will be automatic release of load molecule from the carrier to restore the equilibrium. The release rate will be determined by the speed of utilization of the free load molecule. The total capacity of the carrier will also determine the length of time the carrier can maintain a given concentration of free load molecule or therapeutic agent before it runs out of load molecule to release.

A variety of factors may affect the Kd of the load molecule to hydrophobic-core carrier and thus the release rate. These include density of hydrophobic moieties in the carrier, the size of hydrophobic moieties, density of protective moieties in the carrier, size of protective chains in the carrier, the overall size of the hydrophobic-core carrier, the environment around the hydrophobic-carrier-load molecule complex, and rate of utilization or elimination of free load molecule by cells and organs of the body. The surrounding environmental conditions include temperature, polarity of the solvent which may be determined by ionic strength, protein and organic molecule concentrations, and osmolality. Proteins and organic molecules may also displace the load molecules from the carrier depending on the density of protective chains and the hydrophobicity of the displacing proteins or molecules.

To illustrate further, a wide range of dissociation rates may be obtained by adjusting the hydrophobicities of the backbones or side chains of the polymers while still maintaining sufficient biodegradability for the use intended for any such polymer. Such a result may be achieved by varying both the hydrophobic groups and the protective groups of the polymer.

One protocol generally accepted in the field to determine the equilibrium constant of any load molecule in an aqueous environment, or other material, involves dissociation of the load molecule or other material in a PBS solution (50 mM $PO_4$, 150 mM NaCl, pH 7.4) at 37° C. For purposes of the present invention, the term "PBS protocol" is used herein to refer to such protocol.

In certain instances, the free load molecule concentration maintained by different hydrophobic-core carriers of the present invention may be compared by subjecting them to such a protocol. In certain instances, it may be necessary to process several different hydrophobic-core carriers in the same fashion to allow direct and relatively accurate comparisons of different hydrophobic-core carriers to be made. Such comparisons may indicate that any one hydrophobic-core carrier may maintain the active agent at a concentration of from about 2 nM or less to about 1000 nM or more, inclusive, than another hydrophobic-core carrier. Alternatively, a comparison may reveal a concentration difference of about 3, 5, 7, 10, 25, 50, 100, 250, 500 or 750 nM. Even higher free load molecule concentration differences are contemplated by the present invention and Kd protocols.

In certain embodiments, the equilibrium constant may represent a mono- or bi-phasic system (or a two site-system, with two Kds). Release of load molecules may be characterized in certain instances by an initial increased release rate or high free load molecule concentration, which may release from about 5 to about 50% or more of the load molecule until that site with high Kd is depleted, or alternatively about 10, 15, 20, 25, 30 or 40%, followed by a much lower free load molecule concentration in which the site with low Kd is responsible.

The release rate of the active agent may also be characterized by the amount of such material released per day per mg of carrier. For example, in certain embodiments, when the carrier is a polymer, the release rate may vary from about 1 ng or less of load molecule per day per mg of polymeric system to about 5000 or more ng/day/mg. Alternatively, the release rate may be about 10, 25, 50, 75, 100, 125, 150, 175, 200, 250, 300, 350, 400, 450, 500, 600, 700, 800 or 900 ng/day/mg. In still other embodiments, the release rate of the active agent may be 20,000 ng/day/mg or even higher. In certain instances, active agents characterized by such release rate protocols may include therapeutic agents, antigens, diagnostics, targeting moieties and other substances.

In another aspect, the rate of release of the load molecule may be presented as the half-life of load molecule in the hydrophobic-core carrier.

In addition to the embodiment involving protocols for in vitro determination of release rates, in vivo protocols, whereby in certain instances release rates of active agents from the carrier may be determined in vivo, are also contemplated by the present invention. Other assays useful for determining the release of active agents from the carriers of the present invention may be envisioned.

Synthesis of the Compositions

Figure 3:
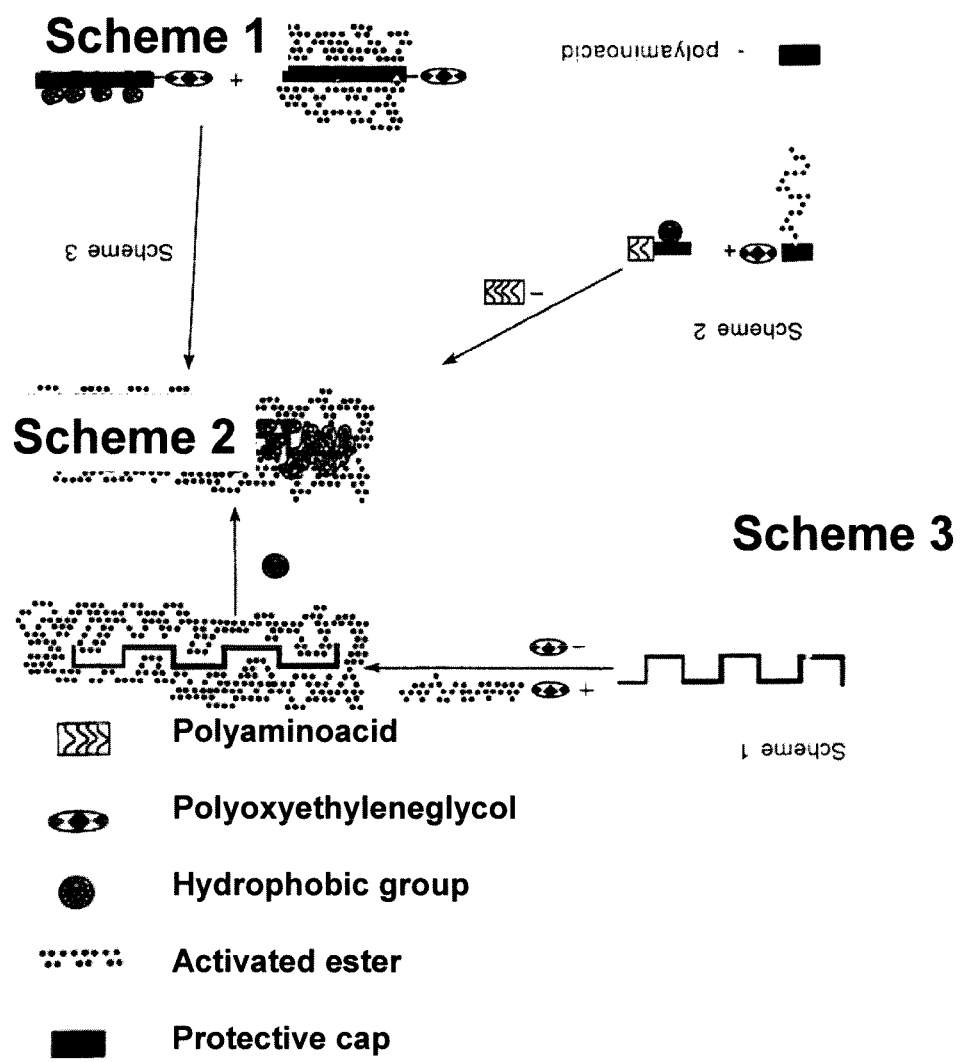
FIG. 3 depicts a diagram of schemes for synthesizing the composition of the invention.

The compositions of this invention may be synthesized using any one of the following methods (FIG. 3). An example of a synthesis of a hydrophobic-core carrier composition using poly-L-lysine as a polymeric carrier, MPEG as a protective chain, and a hydrophobic group is provided. This synthetic composition is especially suitable as a hydrophobic-core carrier for organic drugs, peptide/protein therapeutic agents, or contrast agents.

Scheme 1:

The compositions may be prepared in two stages by first reacting a polyamino acid with activated MPEG analogs, and then reacting this reaction mixture with an activated hydrophobic compound. This procedure is preferred when poly-L-lysine is used as the polymeric carrier (FIG. 3).

Figure 4:
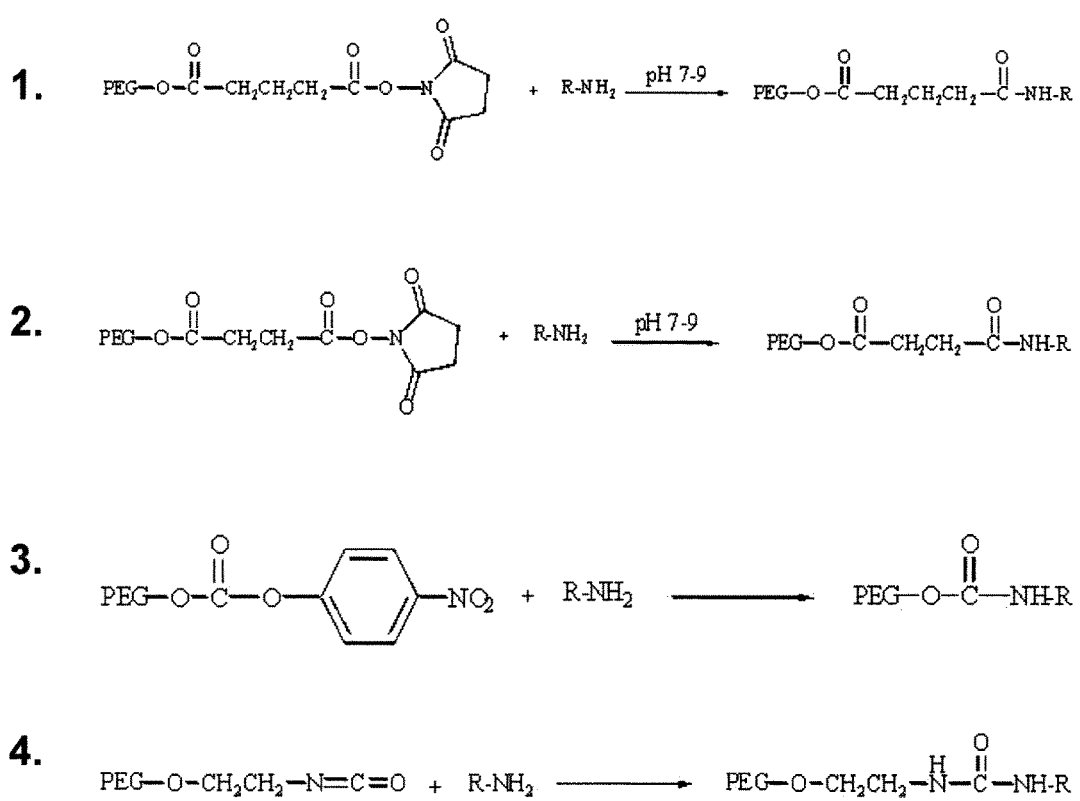
FIG. 4 depicts some of the chemical reactions that may be used to add PEG protective groups, analogs or derivatives thereof, to amino group containing carriers.
Figure 5:
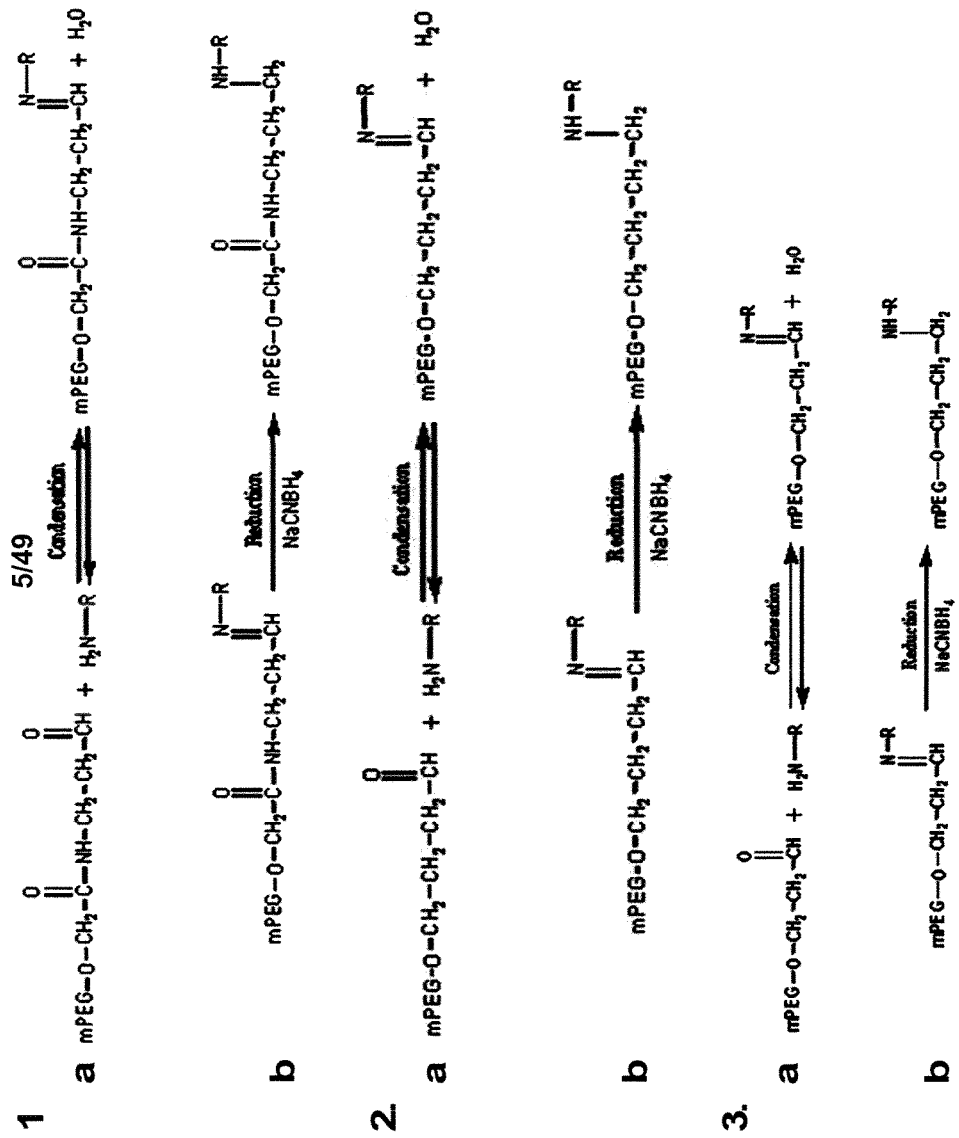
FIG. 5 depicts some of the chemical reactions that may be used to add aldehyde PEG derivatives to amino group containing carriers. These are two step condensation-reduction reactions (a & b).

Epsilon-amino groups of poly-L-lysine are reacted with activated derivatives of carboxylated MPEG, e.g., acid chlorides, anhydrides, mixed anhydrides, nitrenes, isothiocyanates and imidazolides, and activated esters, e.g. hydroxysuccinimide, hydroxysulfosuccinimide, p-nitrophenyl, benzotriazolide. There are other ways of attaching PEGs, their analogs, or their derivatives to amino groups along the polymeric carrier as illustrated in FIG. 4, and FIG. 5, where R represent the carrier.

The hydrophobic molecule is brought into reaction with the remaining amino groups, either in activated form, e.g., anhydride, mixed anhydride, or isothiocyanate, or in a non-activated form. If the hydrophobic molecule is in the non-activated form, it can be activated in the presence of succinimide or sulfosuccinimide and carbodiimide to obtain an activated ester, and then brought into reaction with the remaining amino groups. The reaction may be preceded by an additional chemical modification of the polyamino acid backbone or MPEG chains which is not limited to reactions resulting in the formation or elimination of at least one chemical bond. There are other ways of attaching hydrophobic groups, their analogs, or their derivatives to amino groups along the polymeric carrier. These ways are illustrated in FIG. 4 and FIG. 5, except that in this case PEG or mPEG will be the hydrophobic groups and R remains a carrier.

The sequence of chemically linking the protective chains and a hydrophobic group to a polymeric carrier may be reversed, i.e., linking the hydrophobic groups first and then linking protective chain(s) to the polymeric carrier, but preferably, the hydrophobic group is used as a mono-functional activated analog, i.e., one molecule of activated hydrophobic group forms only one covalent linkage with a polymeric carrier.

Scheme 2:

The compositions also may be synthesized using standard peptide synthesis protocols with modified amino acid precursors such as MPEG-amino acid and hydrophobic-amino acid. In this case, hydrophobic groups and PEG may be alternated in a controllable manner.

Scheme 3:

Oligomers of PEG-polyamino acids may be conjugated with oligomers of hydrophobic groups-polyamino acids to form a block-co-polymer.

All three schemes will result in predictable compositions with highly predictable molecular weight distributions.

Linking MPEG to the polymeric carrier first prevents possible cross-linking of the polyamino acid in the subsequent reaction. MPEG chains prevent the formation of by-products because they create a steric barrier against cross-linking the reagent. Therefore, the formation of high-molecular weight products can be controlled, which makes the synthetic steps predictable. As a result, a homogenous preparation is obtained with a narrow molecular weight distribution.

Figure 2:
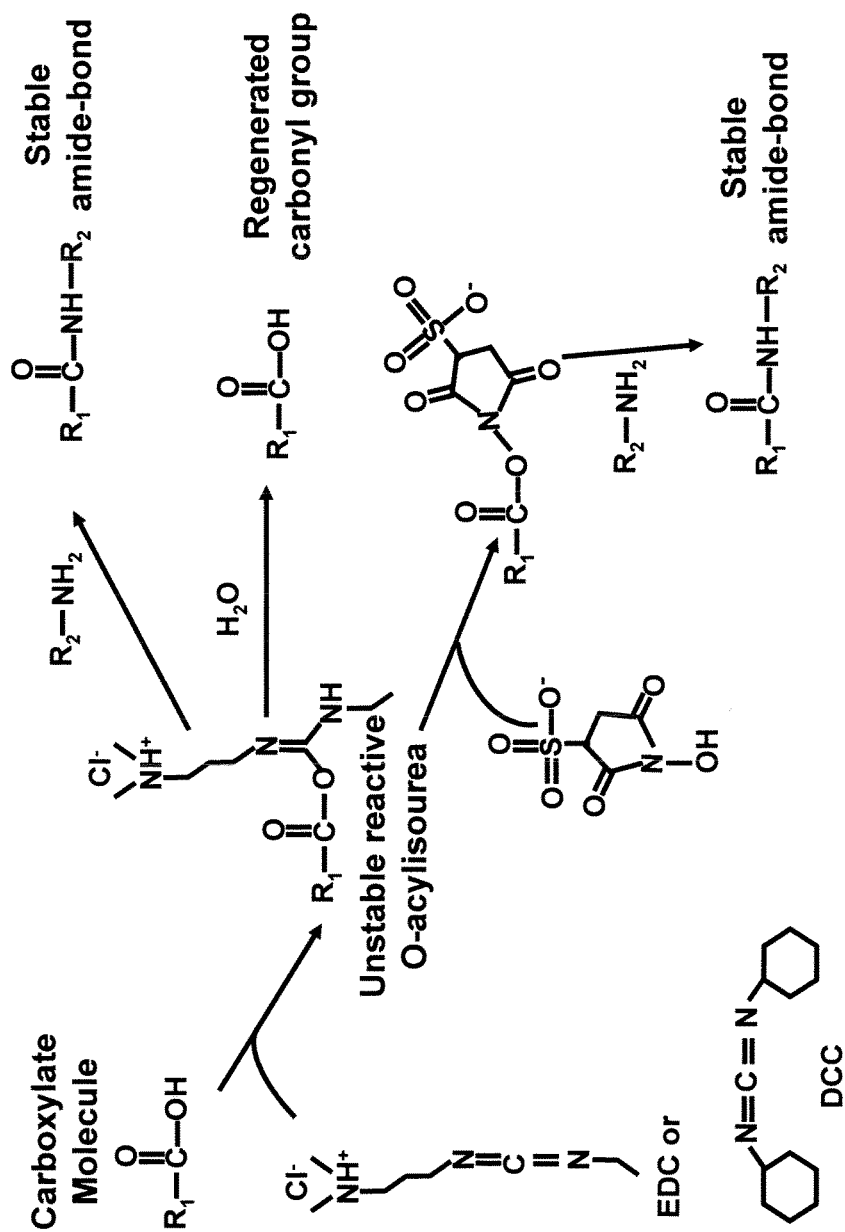
FIG. 2 depicts a diagram of various chemical reactions for making amide bonds that are useful in making the composition of the invention; R1 can be alkyl-carboxyl or aromatic-carboxyl and $R_2$ can be polylysine, or polylysine-PEG; or $R_1$ can be PEG-carboxyl and $R_2$ can be polylysine, alkyl-polylysine, or aromatic-polylysine; or $R_1$ can be polyglutamate or polyaspartate and $R_2$ can be PEG-amine, alkyl-amine or aromatic-amine; or $R_1$ can be polyglutamate-PEG or polyaspartate-PEG and $R_2$ can be alkyl-amine or aromatic-amine. EDC is a water soluble version of DCC; both can be used to carry out the reactions.

When carboxylated carriers are used, such as carboxylated saccharides, or polyaminoacids with carboxy groups in their side chains, such as polyaspartic acid or polyglutamic acid, the polymeric carrier is preferably activated in the presence of carbodiimide and sulfosuccinimide, and then reacted with aminated protective chains and aminated hydrophobic groups either simultaneously or in sequence, such as MPEG monoamine at pH 7-9 (FIG. 2).

Figure 6:
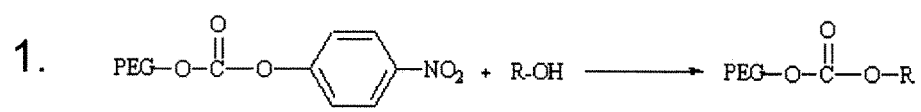
FIG. 6 depicts some of the chemical reactions that may be used to add PEG protective groups, analogs or derivatives thereof, to hydroxyl containing carriers.
Figure 6:
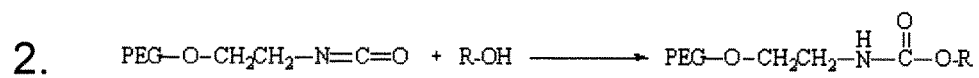
Figure 6:
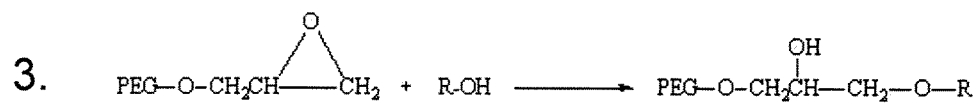
Figure 7:
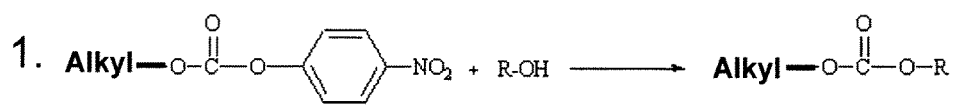
FIG. 7 depicts some of the chemical reactions that may be used to add alkyl hydrophobic groups to hydroxyl containing carriers.
Figure 7:
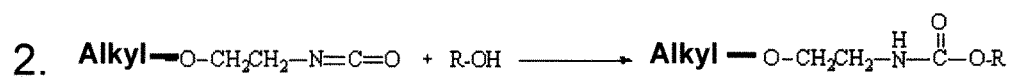
Figure 7:
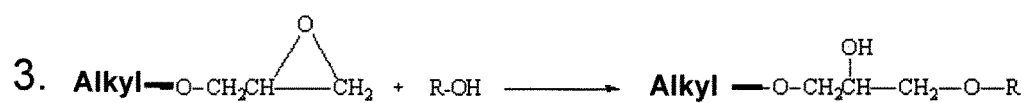
Figure 8:
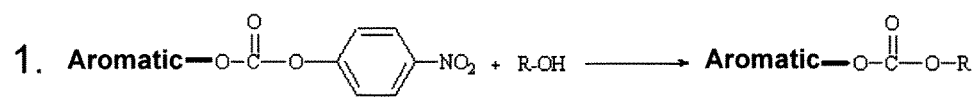
FIG. 8 depicts some of the chemical reactions that may be used to add aromatic hydrophobic groups to hydroxyl containing carriers.
Figure 8:
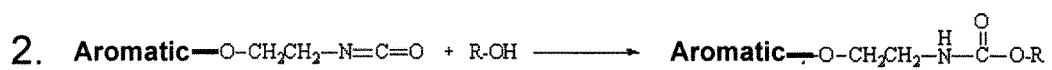
Figure 8:
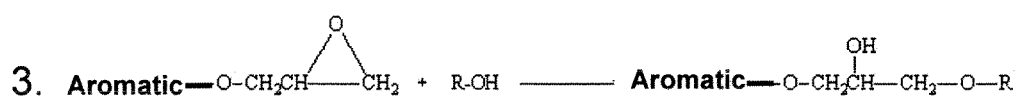

When hydroxylated carriers are used, such as polyserine or polythreonine, or any polymers with hydroxyl groups in their side chains, the protective groups, such as PEG, are preferably activated as illustrated in FIG. 6. Similarly the hydrophobic groups such as alkyl and aromatic groups are also preferably activated as illustrated in FIG. 7 and FIG. 8.

The polymeric carriers preferably contain peptide bonds. The same bonds are involved in conjugating a hydrophobic molecule with reactive groups of the amino acid side chains. The compositions, therefore, are potentially biodegradable by various animal non-specific peptidases. To assist in vivo elimination of the polymeric carrier, protective chains, and hydrophobic groups, elements of the polymeric carrier, protective chains, or hydrophobic groups could be linked together by a semi-stable linkage, such as S—S bonds. Small amounts of trapped compositions may be removed from the body by degradation to smaller fragments. However, a variety of activated PEG derivatives may be used for the preparation of the compositions resulting in them ranging from virtually undegradable to labile. However, labile compositions are undesirable, since detaching MPEG will result in more extensive accumulation of the load molecule compositions in the reticuloendothelial system.

The protective chains of this invention do not activate the C3 component of complement. The C3 is a component of the complement pathways in the blood which upon activation will lead to a formation of membrane attack complex (MAC) that destroy cells by puncturing hole through the cell membrane. The complete description of these pathways is described in The Merk manual of diagnosis and therapy which is hereby incorporated by reference. This is the distinct advantage of polyethyleneglycol protective chains and their derivatives over previously known agents, e.g. dextran, which are known to activate the C3 component of complement. Similarly the hydrophobic fatty acid component of this composition is not immunoactive because fatty acids are present ubiquitously in biological systems in the form of fatty acid itself and/or triglycerides and are one of the normal sources of energy through citric acid cycle or Krebs cycle known to those skilled in the art. Protective chains prevent the exposure of large amounts of load molecules to receptor cells e.g., glomerulonephral phagocytes, capable of recognizing them if concentration is high enough. However, low concentrations will be recognized by high affinity receptors for the specific load molecule. Protective chains also form a steric barrier which prevents larger serum proteins from displacing the load molecules which would otherwise increase their release. The compositions of this invention also prevent possible toxicity resulting from high concentrations of free load molecules by preventing rapid accumulation of the load molecule in the liver and spleen. Without the load molecule, no expected acute toxicity of the hydrophobic-core carrier compositions of this invention is expected since PEG is known to be non-toxic and the fatty acids are all normally present in biological tissues and fluids.

Administration of the Hydrophobic-Core Composition to the Patient

The hydrophobic-core carrier composition containing load molecule can be administered to patients along with pharmaceutical excipients or diluents. Non-limiting examples of suitable pharmaceutical excipients or diluents include starch, glucose, lactose, sucrose, gelatin, malt, rice, fluor, chalk, silica gel, magnesium carbonate, magnesium stearate, sodium stearate, glycerol monostearate, talc, sodium chloride, dried skim milk, glycerol, propylene, glycol, water, ethanol, buffered water, phosphate buffered saline and the like. These compositions can take the form of solutions, suspensions, tablets, pills, capsules, powders, sustained-release formulations and the like. In another preferred embodiment hydrophobic core composition in any form could be further modulated using suitable, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide even more sustained or delayed release of the load molecule or active ingredient from the carrier after administration to the patient. The compositions are preferably formulated in a unit dosage form, each dosage containing from about 1 to about 1000 mg of the hydrophobic core composition containing 1 ug to 500 mg of load molecule or active ingredient. However, it will be understood that the therapeutic dosage administered will be determined by the physician in the light of the relevant circumstances including the clinical condition to be treated and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical diluent or excipient. These may be administered to humans, domestic pets, livestock, or other animals with a pharmaceutically acceptable diluent or excipient, in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration. Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The active therapeutic formulation of the invention can be provided in lyophilized form for reconstituting, for instance, in isotonic, aqueous, or saline buffers for parental, subcutaneous, intradermal, intramuscular or intravenous administration. The subject composition of the invention may also be administered to the patient in need of a therapeutic agent by liquid preparations for orifice, e.g. oral, nasal, sublingual, administration such as suspensions, syrups or elixirs. The subject composition of the invention may also be prepared for oral administration such as capsules, tablets, pills, and the like, as well as chewable solid formulations. The subject composition of the invention may also be prepared as a cream for dermal administration such as liquid, viscous liquid, paste, or powder.

Figure 30:
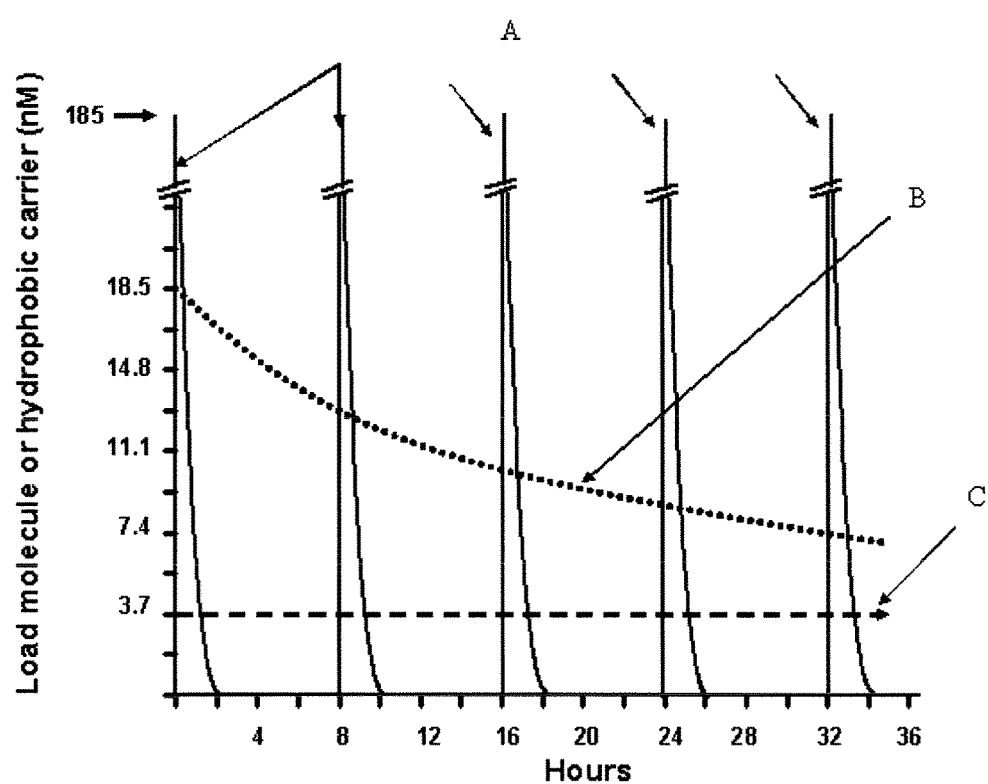
FIG. 30 is the hypothetical free load molecule in the blood with a natural half-life of 20 minutes. There is significant fluctuation in the concentration of free load molecule without the carrier. With the carrier, the free load molecule will be maintained at therapeutic concentration. The nM concentration of hydrophobic carrier decreases with a half-life of 20 hrs. A) Load molecule level resulting from injection 5 mg/kg, 3 times a day without a hydrophobic carrier, this load molecule has a blood half-life of 20 minutes; B) hydrophobic carrier loaded with load molecule has a half-life of 20 hours; C) therapeutic level of free load molecule maintained by hydrophobic carrier.

The presently disclosed compositions are design to deliver active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems as well as being able to traverse the blood-brain barrier. Administration of an active agent bound to hydrophobic-core carrier composition of the present invention results in an increased bioavailability of the active agent compared to administration of the active agent alone, as shown in hypothetical scenario in FIG. 30. One of the embodiment of the present invention is a hydrophobic carrier that is expected to have a half-life of 20 hours and to accumulate at sites with increased vascular permeability. This is based on previous study nanocarrier with similar size protected by poly(ethylene glycol). Such embodiment will be ideal in prolonging the exposure of the body to load molecules with very short biological half-life as illustrated in FIG. 30. This, therefore result in increase bioavailability.

It is the intention of the present invention to provide a method of treatment of various diseases described in the "The Merk Manual of Diagnosis and Therapy" (published 1992 by Merck Laboratories which is a division of Merck & Co., Inc, Rahway, N.J.) using compositions described in the present invention along with appropriate load molecule selected from that described in PDR or Physician Desk Reference (published 2001 by Medical Economics Company, Inc. Montvale, N.J.). The Merk Manual of Diagnosis and Therapy and the PDR are hereby incorporated by reference. The appropriateness of a load molecule for particular disease can be ascertained by checking "The Merk Manual of Diagnosis and Therapy" or the PDR.

Preferred Compositions of the Invention

The invention also features a composition having polyamino acid carrier with the formula:

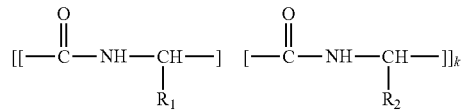

wherein the groups can be linked in any order, e.g., the hydrophobic group $R_1$ unit can be repeated several times in the chain before a protective chain $R_2$ unit occurs, and vice versa, wherein k is 50-560;

The hydrophobic group $R_1$ is selected from a group comprising but not limited to:

a) a modified lysine R group with a hydrophobic molecule attached by amide bond such as but not limited to:
—$(CH_2)_4NHCO(CH_2)_nCH_3$,
—$(CH_2)_4NHCO(C_6H_4)(CH_2)_nCH_3$,
—$(CH_2)_4NHCO(CH_2)_n(C_6H_5)$, or
—$(CH_2)_4NHCO[CxHyOz]$,
where n is 0-24; x is 6-36; y is 5-73; z is 0-10;

b) a modified aspartate R group with a hydrophobic molecule attached by amide bond such as but not limited to:
—$CH_2CONH(CH_2)_nNHOC(CH_2)_nCH_3$,
—$CH_2CONH(CH_2)_nNHOC(C_6H_4)(CH_2)_nCH_3$,
—$CH_2CONH(CH_2)_nNHOC(CH_2)_n(C_6H_5)$,
—$CH_2CONH(CH_2)_nOPO_2OCH_2CH[OOC(CH)_n(CHCH)(CH_2)_nCH_3]CH\ OOC(CH_2)_n(CHCH)(CH_2)_nCH_3$,
—$CH_2CONHCH[CH_2OH]CHOHCHCH(CH_2)_nCH_3$, or
—$CH_2CONH[CxHyOz]$,
where n is 0-24; x is 6-36; y is 5-73; z is 0-10;

c) a modified glutamate R group with a hydrophobic molecule attached by amide bond such as but not limited to:
—$(CH_2)_2CONH(CH_2)_nNHOC(CH_2)_nCH_3$,
—$(CH_2)_2CONH(CH_2)_nNHOC(C_6H_4)(CH_2)_nCH_3$,
—$(CH_2)_2ONH(CH_2)_nNHOC(CH_2)_4C_6H_5)$,
—$(CH_2)_2CONH(CH_2)_nOPO_2OCH_2CH[OOC(CH_2)_n(CHCH)(CH_2)_nCH_3]CHOOC(CH_2)_n(CHCH)(CH_2)_n—CH_3$,
—$(CH_2)_2CONHCH[CH_2OH]CHOHCHCH(CH_2)_nCH_3$, or
—$(CH_2)_2CONH[CxHyOz]$,
where n is 0-24; x is 6-36; y is 5-73; z is 0-10;

d) a modified serine R group with a hydrophobic molecule attached by ester bond such as but not limited to:
—$CH_2OOC(CH_2)_nCH_3$,
—$CH_2OOC(C_6H_4)(CH_2)_nCH_3$,
—$CH_2OOC(CH_2)_n(C_6H_5)$,
—$CH_2OOC[CxHyOz]$,
where n is 0-24; x is 6-36; y is 5-73; z is 0-10;

e) a modified threonine R group with a hydrophobic molecule attached by ester bond such as but not limited to:
—CH$_2$[CH$_3$]OOC(CH$_2$)$_n$CH$_3$,
—CH$_2$[CH$_3$]OOC(C$_6$H$_4$)(CH$_2$)$_n$CH$_3$
—CH$_2$[CH$_3$]OOC(CH$_2$)$_n$(C$_6$H$_5$),
—CH$_2$[CH$_3$]OOC[CxHyOz],
where n is 0-24; x is 6-36; y is 5-73; z is 0-10; or f) a modified tyrosine R group with a hydrophobic molecule attached by ester bond such as but not limited to:
—(C$_6$H$_4$)OOC(CH$_2$)CH$_3$,
—(C$_6$H$_4$)OOC(C$_6$H$_4$)(CH$_2$)$_n$CH$_3$,
—(C$_6$H$_4$)OOC(CH$_2$)$_n$(C$_6$H$_5$), or
—(C$_6$H$_4$)OOC[CxHyOz],
where n is 0-24; x is 6-36; y is 5-73; z is 0-10.

The protective group R$_2$ is selected from a group comprising but not limited to a) a modified lysine R group with a protective group attached by amide bond such as but not limited to:
—(CH$_2$)$_4$NHCO(CH$_2$)$_n$OC-A-OR$_3$, or
—(CH$_2$)$_4$NHCOCH$_2$-A-OR$_3$,
where n is 2-22;
R$_3$ is H, (CH$_2$)CH$_3$ or (CH$_2$)$_p$COOH, p is 0-7; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units;

b) a modified serine R group with a protective group attached by ester bond such as but not limited to
—CH$_2$OOC(CH$_2$)$_n$OC-A-OR$_3$,
—CH$_2$OOCCH$_2$-A-OR$_3$, or
—CH$_2$OOCCH$_2$CH$_2$-A-OR$_3$,
where n is 2-22;
R$_3$ is H, (CH$_2$)CH$_3$ or (CH$_2$)$_p$COOH, p is 0-7; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units;

c) a modified threonine R group with a protective group attached by ester bond such as but not limited to
—CH(CH$_3$)OOC(CH$_2$)$_n$OC-A-OR$_3$,
—CH(CH$_3$)OOCCH$_2$-A-OR$_3$, or
—CH(CH$_3$)OOCCH$_2$CH$_2$-A-OR$_3$,
where n is 2-22;
R$_3$ is H, (CH$_2$)$_p$CH$_3$ or (CH$_2$)$_p$COOH, p is 0-7; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units;

d) a modified aspartate R group with a protective group attached by ester bond such as but not limited to
—CH$_2$COOC(CH$_2$)$_n$CO-A-OR$_3$,
where n is 2-22;
R$_3$ is H, (CH$_2$)$_p$CH$_3$ or (CH$_2$)$_p$COOH, p is 0-7; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units;

e) a modified aspartate R group with a protective group attached by amide bond such as but not limited to
—CH$_2$CONH(CH$_2$)$_n$NHCOCH$_2$CH$_2$-A-OR$_3$,
—CH$_2$CONH(CH$_2$)$_n$NHCOCH$_2$-A-OR$_3$, or
—CH$_2$CONH(CH$_2$)$_n$NHCO(CH$_2$)$_y$CO-A-OR$_3$,
where n is 2-22;
R$_3$ is H, (CH$_2$)$_p$CH$_3$ or (CH$_2$)$_p$COOH, p is 0-7; y is 2-6; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units;

f) a modified glutamate R group with a protective group attached by ester bond such as but not limited to
—(CH$_2$)$_2$COOC(CH$_2$)$_n$CO-A-OR$_3$,
where n is 2-22;
R$_3$ is H, (CH$_2$)$_p$CH$_3$ or (CH$_2$)$_p$COOH, p is 0-7; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units;

g) a modified glutamate R group with a protective group attached by amide bond such as but not limited to
—(CH$_2$)$_2$C ONH(CH$_2$)$_n$NHCOCH$_2$CH$_2$-A-OR$_3$,
—(CH$_2$)$_2$CONH(CH$_2$)$_n$NHCOCH$_2$-A-OR$_3$, or
—(CH$_2$)$_2$CONH(CH$_2$)$_n$NHCO(CH$_2$)$_y$CO-A-OR$_3$,
where n is 2-22;
R$_3$ is H, (CH$_2$)$_p$CH$_3$ or (CH$_2$)$_p$COOH, p is 0-7; y is 2-6; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units; or h) a modified tyrosine R group with a protective group attached by ester bond such as but not limited to
—(C$_6$H$_4$)OCO(CH$_2$)$_n$CO-A-OR$_3$,
—(C$_6$H$_4$)OOCCH$_2$CH$_2$-A-OR$_3$,
—(C$_6$H$_4$)OOCCH$_2$-A-OR$_3$, or
—(C$_6$H$_4$)OCO(CH$_2$)$_n$NHCO(CH$_2$)$_y$CO-A-OR$_3$,
where n is 2-22;
R$_3$ is H, (CH$_2$)$_p$CH$_3$ or (CH$_2$)$_p$COOH, p is 0-7; y is 2-6; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units.

It is also the object of the present invention that the composition may only have R$_2$, with none or very few R$_1$ especially when R$_2$ contains a significant amount of hydrophobic groups flanking the carrier and protective groups. The subject of the invention also features a composition having polyamino acid carrier with the formula:

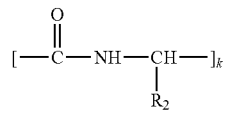

where R$_2$ represents a combination of hydrophobic groups and protective groups selected from a group comprising but not limited to:
—(CH$_2$)$_4$NHCO(CH$_2$)$_n$OC-A-OR$_3$,
—(CH$_2$)$_4$NHCO(CH$_2$)$_n$NHCO(CH$_2$)$_y$CO-A-OR$_3$,
—CH$_2$OOC(CH$_2$)$_n$OC-A-OR$_3$,
—CH$_2$OOC(CH$_2$)$_n$NHCO(CH$_2$)$_y$CO-A-OR$_3$,
—CH(CH$_3$)OOC(CH$_2$)$_n$OC-A-OR$_3$,
—CH(CH$_3$)OOC(CH$_2$)$_n$NHCO(CH$_2$)$_y$CO-A-OR$_3$,
—CH$_2$COOC(CH$_2$)$_n$CO-A-OR$_3$,
—CH$_2$COOC(CH$_2$)$_n$NHCO(CH$_2$)$_y$CO-A-OR$_3$,
—CH$_2$CONH(CH$_2$)$_n$NHCOH$_2$CH$_2$-A-OR$_3$,
—CH$_2$CONH(CH$_2$)$_n$NHCO(CH$_2$)$_y$CO-A-OR$_3$,
—(CH$_2$)$_2$COOC(CH$_2$)$_n$CO-A-OR$_3$,
—(CH$_2$)$_2$COOC(CH$_2$)$_n$NHCO(CH$_2$)$_y$CO-A-OR$_3$,
—(CH$_2$)$_2$C ONH(CH$_2$)$_n$NHCOCH$_2$CH$_2$-A-OR$_3$, —(CH$_2$)$_2$CONH(CH$_2$)$_n$NHCO(CH$_2$)$_y$CO-A-OR$_3$,
—(C$_6$H$_4$)OCO(CH$_2$)$_n$CO-A-OR$_3$, or
—(C$_6$H$_4$)OCO(CH$_2$)$_n$NHCO(CH$_2$)$_y$CO-A-OR$_3$,
where n is 2-22;
R$_3$ is H, (CH$_2$)$_p$CH$_3$ or (CH$_2$)$_p$COOH, p is 0-7;
y is 2-6; and
A is [OCH$_2$CH$_2$]$_x$ or [OCH$_2$CH$_2$]$_x$ or [OCHCH$_3$CH$_2$]$_x$,
where x is 17-250, or various combinations of [OCH$_2$CH$_2$], [OCH$_2$CH$_2$], and/or [OCHCH$_3$CH$_2$] with total of 17-250 units.

Non-Immunogenicity

Prevention of the cell surface from exposure to high concentrations of load molecules is accomplished by using load molecules with high binding affinities to the hydrophobic core, resulting in only nanomolar to picomolar concentrations of free load molecule at any given moment. In addition, the PEG protecting groups will protect the concentrated bound load molecule from being in contact with the cell surface. This will Formulations The hydrophobic core carrier compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject hydrophobic carrier compositions may be suitable for oral, nasal, topical (including buccal and sublingual), rectal, vaginal, aerosol and/or parenteral administration. The formulations of hydrophobic carrier compositions may conveniently be presented in unit dosage form and may be prepared by any methods well known in the art of pharmacy. The amounts of composition that may be combined with other excipients to produce a single dose that vary depending upon the subject being treated, and the particular mode of administration.

Methods of preparing these hydrophobic carrier-load molecule formulations include the step of bringing into association hydrophobic carrier of the present invention with the load molecule and, optionally, one or more accessory ingredients. In general, the formulations are prepared by uniformly and intimately bringing into association load molecules with hydrophobic carriers, or finely divided solid hydrophobic carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject hydrophobic carrier-load molecule composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the hydrophobic carrier-load molecule compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. The liquid dosage hydrophobic carrier-load molecule formulation may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspension dosage of hydrophobic carrier-load molecule formulation may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Hydrophobic carrier-load molecule formulations for rectal or vaginal administration may be presented as a suppository, which may be prepared by mixing a load molecule with one or more suitable hydrophobic carriers and other excipients comprising, for example, cocoa butter, polyethylene glycol, a suppository wax or a salicylate, and which is solid at room temperature, but liquid at body temperature and, therefore, will melt in the body cavity and release the hydrophobic carrier with load molecule. Formulations which are suitable for vaginal administration also include pessaries, tampons, creams, gels, pastes, foams or spray formulations containing excepients as are known in the art to be appropriate.

Hydrophobic carrier-load molecule dosage formulations for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Hydrophobic carrier-load molecule compositions of the present invention may also be in the form of baby wipes.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Hydrophobic carrier-load molecule compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Treatment of a Disease Using the Hydrophobic-Core Carrier Composition

Insulin-insufficient diabetes is a disease in which the body does not produce or properly use insulin, a hormone that regulates blood sugar. Insulin-insufficient diabetes is the third most common disease and fourth leading cause of death in North America with an estimated 18.2 million (6.3% of the population) affected in the United States. The annual economic cost of insulin-insufficient diabetes in the US is estimated to be as much as $100 billion, making the disease an important clinical and public health problem (for review see Ettaro, L., et al., *Cost-of-illness studies in diabetes mellitus. Pharmacoeconomics,* 2004. 22(3): p. 149-64).

There are two major types of diabetes: Type 1 or T1D, (5-10% of diabetics) in which the immune system attacks the insulin-producing beta cells of the pancreas and Type-2 or T2D in which individuals develop resistance to insulin. Untreated diabetics are affected by a myriad of complications including eye, kidney, nerve and cardiovascular disease. The goal of insulin-insufficient diabetes treatment is to regulate blood sugar levels and prevent hyperglycemia. While high blood sugar can be controlled in Type-2 diabetes by lifestyle changes and oral anti-hyperglycemic agents, the only standard treatment for T1D, however, is strict control of blood glucose levels by insulin injection, with the associated risk of serious hypoglycemic events. More recently, the transplantation of insulin-producing pancreatic islet cells has been shown to be highly effective in reversing insulin-insufficient diabetes in Type I patients. The success of this therapy however depends on effective immunosuppression to prevent the rejection of the transplanted islets by the allo- and autoimmune response of the patient (Shapiro, A. M., S. A. Nanji, and J. R. Lakey, *Clinical islet transplant: current and future directions towards tolerance.* Immunol Rev, 2003. 196: p. 219-36), though reports of sustained tolerance to the transplant have been reported. If no alternative is found, this transplantation approach is expected to become a clinical standard of care despite the toxicities seen with the chronic immunosuppressive regimen.

The recent finding that islet cells can be regenerated in diabetic animals by the peptide hormone Glucagon-like peptide 1 (GLP-1) (Drucker, D. J., *Enhancing incretin action for the treatment of type 2 diabetes.* Diabetes Care, 2003. 26(10): p. 2929-40, Perry, T. and N. H. Greig, *The glucagon-like peptides: a double-edged therapeutic sword?* Trends Pharmacol Sci, 2003. 24(7): p. 377-83) has raised the exciting possibility of a new approach for a cure that avoids the need for transplantation of islets and its associated complications. GLP-1 has a very short half-life in vivo necessitating the use of potentially immunogenic analogues with extended half-life for evaluation of efficacy. Indeed, an analogue of GLP-1 (Exenatide) is currently being evaluated in an NIH-sponsored Phase I clinical trial in combination with an immunosuppressant for the reversal of T1D. However, 38% of type 2 diabetic patients that have received Exenatide developed antibodies against this GLP-1 analogue which could potentially limit efficacy of the hormone in the future. The present invention extended the circulation half-life of native GLP-1 from .about.5 min to surprisingly greater than 24 h (FIG. 44) offering the potential to perform islet regeneration studies without the development of neutralizing antibodies. The present invention facilitates the development of a long acting native GLP-1 to regenerate beta cells and/or treat insulin-insufficient diabetes.

Limitations of Native-GLP-1 as a Drug and Problems in the Art:

GLP-1 (7-36 amide), is a potent intestinal hormone that increases insulin secretion. Released in response to a meal, GLP-1 stimulates insulin secretion from pancreatic beta cells, inhibits the release of the hormone glucagon (which functions as an insulin antagonist) and delays gastric emptying. By interacting with the GLP-1 receptor on pancreatic islet cells, GLP-1 leads to a cascade of signaling reactions resulting in an increased exocytosis of insulin-containing granules in a strictly glucose-dependent manner (at glucose concentrations >4.5 mM). Additionally, GLP-1 strongly enhances all steps of insulin biosynthesis including transcription of the insulin gene (Ahren, B., et al., *Improved glucose tolerance and insulin secretion by inhibition of dipeptidyl peptidase IV in mice.* Eur J Pharmacol, 2000. 404(1-2): p. 239-45). The transcription of other genes essential for beta cell function (glucokinase and Glut-2) is also increased in response to GLP-1 treatment (Ahren, B., et al., *Improved glucose tolerance and insulin secretion by inhibition of dipeptidylpeptidase IV in mice*. Eur J Pharmacol, 2000. 404(1-2): p. 239-45). Given these effects of GLP-1 there is considerable interest in this peptide as a potential therapeutic agent that could stimulate insulin release in Type 2 diabetics with functional beta cells. However, GLP-1 activity is rapidly inhibited as a result of the N-terminal cleavage at the Ala2 position by the dipeptidyl peptidase 4 (DPP4) in the blood stream. The cleavage limits the GLP-1 half-life to 2-6 minutes, which is considered a serious limitation to its therapeutic potential. A number of GLP-1 analogues are being developed to resist the effects of DPP4 (Table 1) but none of them have used native GLP-1 and a carrier system in the present invention. Some of these have been shown to normalize fasting and postprandial blood glucose in diabetic animal models (Xu, G., et al., *Exendin-4 stimulates both beta-cell replication and neogenesis, resulting in increased beta-cell mass and improved glucose tolerance in diabetic rats*. Diabetes, 1999. 48(12): p. 2270-6) as well as in humans (Drucker, D. J., *Enhancing incretin action for the treatment of type 2 diabetes*. Diabetes Care, 2003. 26(10): p. 2929-40). The most advanced of these, extendin 4 or Exenatide (a reptilian analog of human GLP-1), is now approved for Type 2 diabetes. However, the effects of long term systemic administration of these non-native peptides are unknown. Side effects of sustained administration appear to result in gastrointestinal and cardiovascular side effects (Nielsen, L. L. and A. D. Baron, *Pharmacology of exenatide (synthetic exendin-4) for the treatment of type 2 diabetes*. Curr Opin Investig Drugs, 2003. 4(4): p. 401-5) and doses have to be carefully controlled to prevent hypoglycemic episodes. Furthermore, the administration of non-native GLP-1 analogs such as exenatide is now documented to cause development of antibodies in 38% of treated type-2 diabetic patients. Although it was indicated that antibodies that developed are non-neutralizing, perhaps due to selectivity to C-terminal rather than N-terminal, it is more likely that with time N-terminal neutralizing antibodies will also develop.

Sitagliptin (7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine phosphate (1:1) monohydrate) is a DPP-4 inhibitor, which is believed to exert its actions in patients with type 2 diabetes by slowing the inactivation of incretin hormones including GLP-1. Concentrations of the active intact hormones are increased by sitagliptin, thereby increasing and prolonging the action of these hormones. Incretin hormones, including glucagon-like peptide-1 (GLP-1) and glucose-dependent insulinotropic polypeptide (GIP), are released by the intestine throughout the day, and levels are increased in response to a meal. These hormones are rapidly inactivated by the enzyme, DPP-4. The incretins are part of an endogenous system involved in the physiologic regulation of glucose homeostasis. When blood glucose concentrations are normal or elevated, GLP-1 and GIP increase insulin synthesis and release from pancreatic beta cells by intracellular signaling pathways involving cyclic AMP. GLP-1 also lowers glucagon secretion from pancreatic alpha cells, leading to reduced hepatic glucose production. By increasing and prolonging active incretin levels, sitagliptin increases insulin release and decreases glucagon levels in the circulation in a glucose-dependent manner. Sitagliptin demonstrates selectivity for DPP-4 and does not inhibit DPP-8 or DPP-9 activity in vitro at concentrations approximating those from therapeutic doses.

| Product | Basis for improvement over native GLP-1 | Stage of development |
| --- | --- | --- |
| Exenatide Amylin Pharma | DPP4-resistant analogue, 53% homology with human GLP-1 | Approved for Type 2 diabetes |
| CJC 1131 Conjuchem | BSA-linked analogue with long half life | Phase II clinical trials |
| Liraglutide Novo Nordisk | BSA-linked fatty-acylated GLP-1 with extended half life | Phase III clinical trials |
| Exenatide LAR Amylin | Sustained release formulation for once weekly- monthly dosing | Phase II clinical trials |
| BIM 51077 Ipsen | Sustained release formulation for once daily to once per two weeks dosing | Phase II study, to confirm the efficacy and safety of this compound in a sustained release formulation will start early 2007. |

As an alternative approach to GLP-1 analogues with extended half-life, small molecule inhibitors of DPP4 are under development to offer the advantage of being orally available. However, these inhibitors have the potential for other side effects given the importance of DPP4 in the cleavage of other molecules important for immune function (Wiedeman, P. E. and J. M. Trevillyan, *Dipeptidyl peptidase IV inhibitors for the treatment of impaired glucose tolerance and type 2 diabetes*. Curr Opin Investig Drugs, 2003. 4(4): p. 412-20).

The observation that GLP-1 not only increases the proliferation of beta cells (Buteau, J., et al., *Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells.* Diabetologia, 1999. 42(7): p. 856-64) and prevents their apoptosis (Urusova, I. A., et al., *GLP-1 inhibition of pancreatic islet cell apoptosis*. Trends Endocrinol Metab, 2004. 15(1): p. 27-33), but also stimulates their neogenesis, inducing the differentiation of new beta cells from ductal progenitor cells (Bulotta, A., et al., *Cultured pancreatic ductal cells undergo cell cycle re-distribution and beta-cell-like differentiation in response to glucagon-like peptide-1*. J Mol Endocrinol, 2002. 29(3): p. 347-60), has led to interest in this peptide for a possible cure for T1D. Indeed, the importance of GLP-1 in islet generation is seen in mice lacking the GLP-1 receptor, which have islets with fewer beta cells and abnormal glucose tolerance (Scrocchi, L. A., et al., *Identification of glucagon-like peptide 1 (GLP-1) actions essential for glucose homeostasis in mice with disruption of GLP-1 receptor signaling*. Diabetes, 1998. 47(4): p. 632-9). The regeneration of islet cells and increase in pancreatic beta cell mass has been demonstrated in animal models (Xu, G., et al., *Exendin-4 stimulates both beta-cell replication and neogenesis, resulting in increased beta-cell mass and improved glucose tolerance in diabetic rats*. Diabetes, 1999. 48(12): p. 2270-6)

by GLP-1 and other agonists of the GLP-1 receptor and, further, GLP-1 has been shown to attenuate the development of insulin-insufficient diabetes after partial pancreatectomy (Xu, G., et al., *Exendin-4 stimulates both beta-cell replication and neogenesis, resulting in increased beta-cell mass and improved glucose tolerance in diabetic rats*. Diabetes, 1999. 48(12): p. 2270-6). Therefore, GLP-1 treatment can potentially regenerate destroyed islets in T1D. Unfortunately, native GLP-1 as a drug is not commercially viable without the present invention. The present invention is capable of providing many benefits that have long been sought by many.

Figure 35:
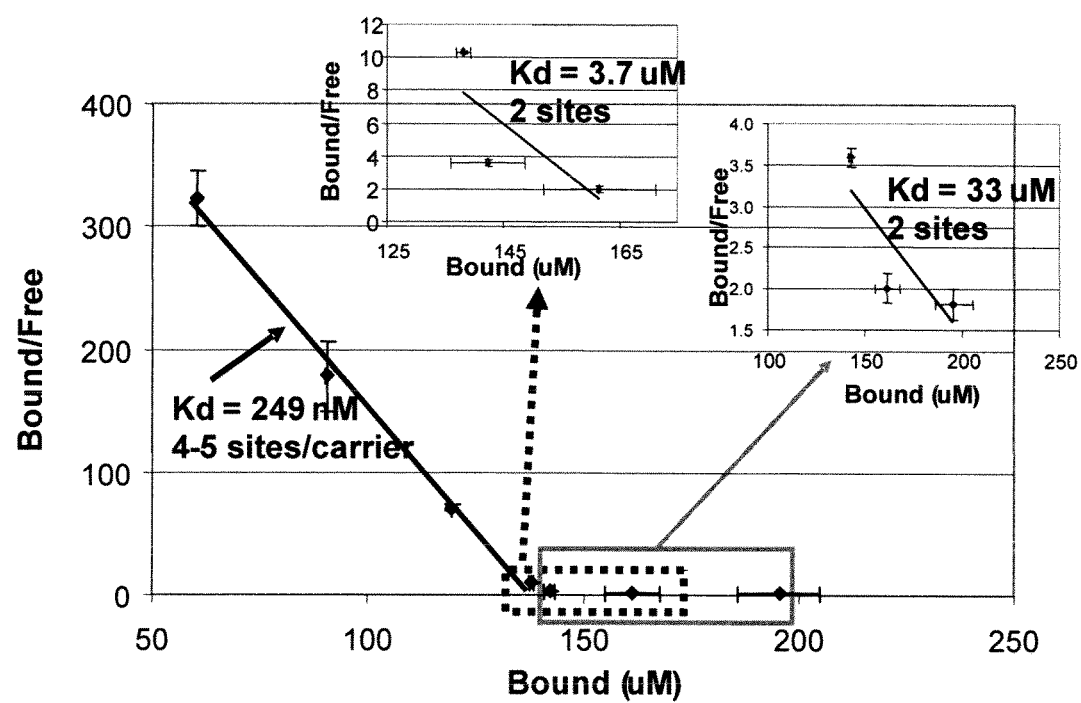
FIG. 35. This shows that PGC-HC based on C18 (C18-20PLPEG5-55; this is a 20 kDa polylysine where 55% of the amino groups were reacted with PEG succinate of 5 kDa molecular weight and the remaining aminogroups were reacted with stearic acid or C18) binds peptides (e.g. GLP-1) with 4-5 sites with Kd in nanomolar range (249 nM). Other sites have lower affinity with two sites with Kd of 2.7 uM and another 2 sites with Kd of 33 uM. In this experiment 10 mg of carrier was loaded (as described in FIG. 34, acetone method) with varying amounts of GLP1. Each loaded carrier was dissolved in 1 ml PBS and allowed to equilibrate for 2 hours. Each solution containing free and bound GLP1 was filtered through 100 kDa molecular cut off filter and each filtrate containing free GLP 1 was quantified by reverse phase HPLC. The bound GLP1 from each solution was released by 70% acetonitrile and similarly quantified by HPLC.
Figure 36:
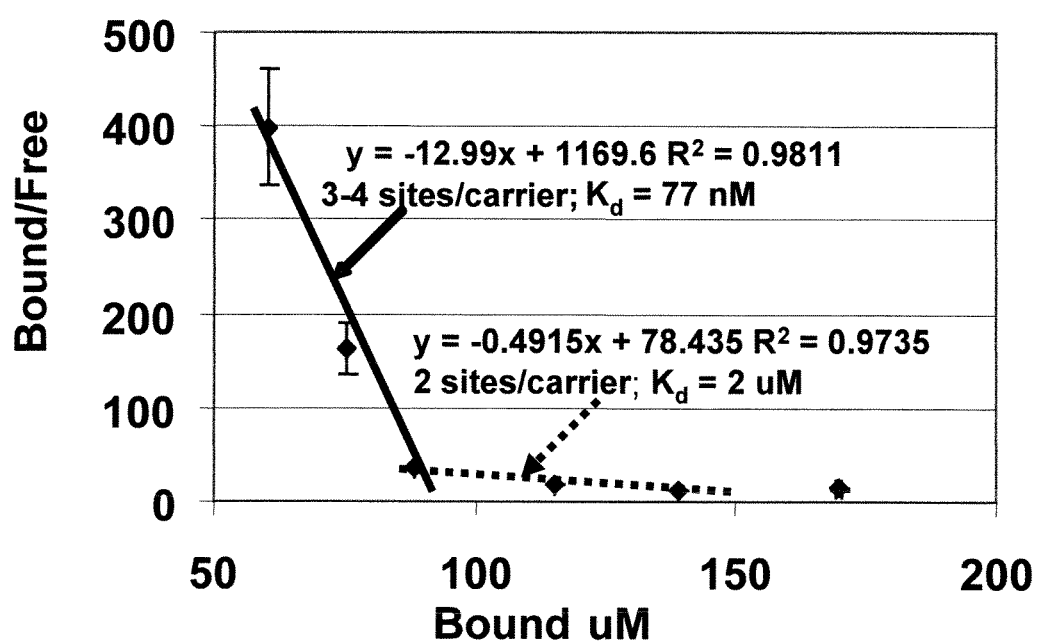
FIG. 36. This shows that PGC-HC based on C24 (C24-20PLPEG5-55; this is a 20 kDa polylysine where 55% of the amino groups were reacted with PEG succinate of 5 kDa molecular weight and the remaining aminogroups were reacted with lignoceric acid or C24) binds peptides (e.g. GLP-1) with 3-4 sites with tight Kd in nanomolar range (77 nM). Another site has lower affinity with two sites with Kd of 2 uM. Other lower affinity site was not analyzed. In this experiment 10 mg of hydrophobic core carrier was loaded (as described in FIG. 34, acetone method) with varying amounts of GLP1. Each loaded carrier was dissolved in 1 ml PBS and allowed to equilibrate for 2 hours. Each solution containing free and bound GLP1 was filtered through 100 kDa molecular cut off filter and each filtrate containing free GLP1 was quantified by reverse phase HPLC. The bound GLP1 from each solution was released by 70% acetonitrile and similarly quantified by HPLC.
Figure 42:
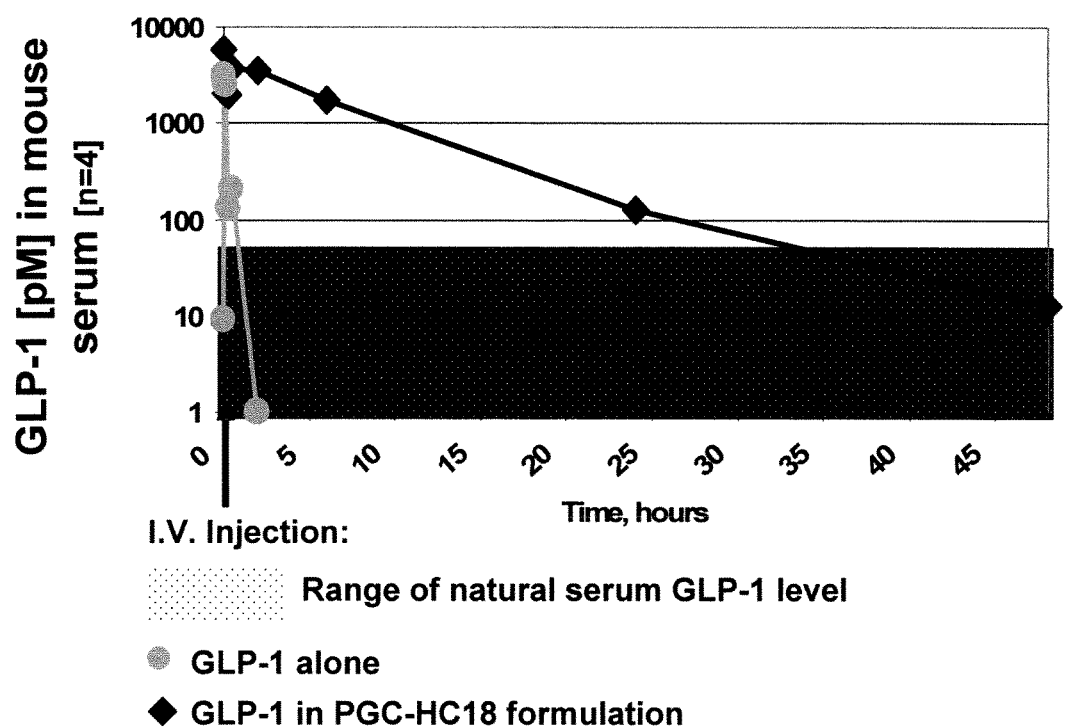
FIG. 42. Time dependent decrease in Total GLP1 in the blood after iv administration of GLP 1 and formulated GLP 1 (PGC-HC18 containing 2% by weight of GLP 1). The PGC-HC18 used in the formulation is a 20 kDa polylysine where 55% of the amino groups were reacted with PEG succinate of 5 kDa molecular weight and the remaining aminogroups were reacted with stearic acid or C18. The elimination half-life of GLP 1 administered alone is just a few minutes while the formulated GLP 1 has half-life of at least 6 hours. Female Balb/c mice were injected i.v. with 2 mg GLP-1 alone or 2 mg GLP-1 in PGC-HC18 formulation. Terminal blood draws were done at given time points. The total GLP 1 (PGC-HC18 bound and unbound) are measured by Elisa kit from Linco (LINCO Research, St. Charles, Mo.).

The present invention includes formulation GLP-1 into at least two of our carriers with dissociation constants of 77 and 249 nM (FIGS. 35 & 36). These Kds are far lower than the Km of DPP4 for GLP-1, thus protecting GLP-1 from degradation. This protection coupled with the increase in effective size, preventing kidney elimination, extended the circulation half-life of our native GLP-1 formulation to surprising extent (FIGS. 42-44) and lowered the glucose level in streptozotocin-induced diabetic rats (FIG. 45). In comparison to GLP-1 analogs, approved or nearing FDA approval, our long-acting GLP-1-formulations have a half-life much greater than what has been achieved with the protease resistant GLP-1 analog (FDA approved Exenatide; t1/2=4 hrs, administered twice a day) or non-protease resistant Liraglutide (Fatty acid linked GLP-1 bound to albumin; t1/2=10 hrs, planned to be administered once a day). It is important to note that our native GLP-1 is unlikely to cause antibody formation that has been seen in patients treated with Exenatide (Byetta). In addition, because of the long circulation half-life of formulated native GLP-1, it is expected to be administered less frequently. Although long acting Exenatide (Byetta-LAR) is under development, our approach is different from Byetta-LAR. Byetta-LAR uses a polymer (polylactic acid that degrades with time) that dissolves under the skin and releases free GLP-1 analog slowly. Our formulation is injected under the skin and the carrier along with GLP-1 circulates in the blood as evident from our measurement of bound and free GLP-1 in the blood where 87.5% of total GLP-1 is bound to the carrier circulating in the blood and the remaining 12.5% is free. This is just one demonstration of the usefulness of the invention and is not intended to limit the scope of the invention.

Another embodiment the present invention relates to a method of treating a patient for insulin-insufficient diabetes comprising; administering to the patient in need thereof a therapeutically effective amount of any of the hydrophobic-core carrier compositions described above, wherein the load molecule is GLP-1.

In another embodiment, the present invention relates to a method of treating a patient for insulin-insufficient diabetes comprising; administering to the patient in need thereof a therapeutically effective amount of any of the hydrophobic-core carrier compositions comprising; a polyamino acid carrier, a methoxy polyethylene glycol protective chain covalently attached to the said polyamino acid carrier, a hydrophobic fatty acid chain covalently attached to the said polyamino acid carrier, a load molecule reversibly bound to the hydrophobic fatty acid chain, wherein the load molecule is GLP-1.

Native-Gastrin and Native-EGF are Subject to Similar Limitation as Native GLP-1;

Transgenic over-expression of gastrin and EGF receptor ligands stimulates islet neogenesis in adult mice, significantly increasing islet cell mass (Wang, T. C., et al., *Pancreatic gastrin stimulates islet differentiation of transforming growth factor alpha-induced ductular precursor cells*. J Clin Invest, 1993. 92(3): p. 1349-56). EGF receptor ligands such as EGF, TGF-alpha, and betacellulin increase the neogenesis and proliferation of insulin-producing beta-islet cells of the pancreas (Suarez-Pinzon, W. L., et al., *Combination therapy with epidermal growth factor and gastrin increases beta-cell mass and reverses hyperglycemia in diabetic NOD mice*. Diabetes, 2005. 54(9): p. 2596-601, Song, S. Y., et al., *Expansion of Pdx1-expressing pancreatic epithelium and islet neogenesis in transgenic mice overexpressing transforming growth factor alpha*. Gastroenterology, 1999. 117(6): p. 1416-26, Krakowski, M. L., et al., *Transgenic expression of epidermal growth factor and keratinocyte growth factor in beta-cells results in substantial morphological changes*. J Endocrinol, 1999. 162(2): p. 167-75, Cras-Meneur, C., et al., *Epidermal growth factor increases undifferentiated pancreatic embryonic cells in vitro: a balance between proliferation and differentiation*. Diabetes, 2001. 50(7): p. 1571-9, Huotari, M. A., J. Palgi, and T. Otonkoski, *Growth factor-mediated proliferation and differentiation of insulin producing INS-1 and RINm5F cells: 15 identification of betacellulin as a novel beta-cell mitogen*. Endocrinology, 1998. 139(4): p. 1494-9, Yamamoto, K., et al., *Recombinant human betacellulin promotes the neogenesis of beta-cells and ameliorates glucose intolerance in mice with diabetes induced by selective alloxan perfusion*. Diabetes, 2000. 49(12): p. 2021-7). In addition, pharmacological treatment of chronic streptozotocin-induced diabetic rats by systemic administration of EGF and gastrin results in normalization of glucose and improved glucose tolerance (Brand, S. J., et al., *Pharmacological treatment of chronic diabetes by stimulating pancreatic beta-cell regeneration with systemic co-administration of EGF and gastrin*. Pharmacol Toxicol, 2002. 91(6): p. 414-20). Histological analysis shows increased beta-cell mass with increased BrdU labeling indicating neogenesis. Importantly, evidence indicate that growth factors such as EGF, also cause induction of immune tolerance towards newly regenerated beta-cells (Suarez-Pinzon, W. L., et al., *Combination therapy with epidermal growth factor and gastrin increases beta-cell mass and reverses hyperglycemia in diabetic NOD mice*. Diabetes, 2005. 54(9): p. 2596-601). To overcome the limitation of native gastrin and native EGF having short biological half-life (both have half-life of few minutes (Hansen, C. P., et al., *Pharmacokinetics and organ metabolism of carboxyamidated and glycine-extended gastrins in pigs*. Am J Physiol, 1996. 271(1 Pt 1): p. G156-63, Lev-Ran, A., et al., *Origin of urinary epidermal growth factor in humans: excretion of endogenous EGF and infused [131I]-human EGF and kidney histochemistry*. Clin Exp Pharmacol Physiol, 1992. 19(10): p. 667-73, Senekowitsch-Schmidtke, R., et al., *In vivo evaluation of epidermal growth factor (EGF) receptor density on human tumor xenografts using radiolabeled EGF and anti-(EGF receptor) mAb 425*. Cancer Immunol Immunother, 1996. 42(2): p. 108-14, Feng, J., et al., *Tissue distribution and plasma clearance of heparin-binding EGF-like growth factor (HB-EGF) in adult and newborn rats*. Peptides, 2005), analogs of EGF and gastrin were used which were administered twice daily by IP injection (U.S. Pat. No. 6,992,060, Suarez-Pinzon, W. L., et al., *Combination therapy with epidermal growth factor and gastrin increases beta-cell mass and reverses hyperglycemia in diabetic NOD mice*. Diabetes, 2005. 54(9): p. 2596-601). Again, this is an example in the art teaching away from the use of native Gastrin and native EGF.

Another embodiment the present invention relates to a method of treating a patient for insulin-insufficient diabetes comprising; administering to the patient in need thereof a therapeutically effective amount of any of the hydrophobic-core carrier compositions described above, wherein the load molecule is EGF and; any of the hydrophobic-core carrier compositions described above, wherein the load molecule is Gastrin.

Another embodiment the present invention relates to a method of treating a patient for insulin-insufficient diabetes comprising; administering to the patient in need thereof a therapeutically effective amount of any of the hydrophobic-core carrier compositions described above, wherein the load molecule is GLP-1 and; any of the hydrophobic-core carrier compositions described above, wherein the load molecule is Gastrin Omeprazole irreversibly inhibits proton pumps in the stomach until the synthesis of new pump occurs (m, W. B., D. P. Blakeman, and J. P. Davis, *Irreversible inactivation of rat gastric (H+-K+)-ATPase in vivo by omeprazole.* Biochem Biophys Res Commun, 1985. 126(1): p. 78-82, Keeling, D. J., et al., *Studies on the mechanism of action of omeprazole.* Biochem Pharmacol, 1985. 34(16): p. 2967-73). It has long been known that proton pump inhibition results in hypergastrinemia where serum gastrin level can increase from 15 μg/ml to over 200 μg/ml (Lamberts, R., et al., *Long-term omeprazole treatment in man: effects on gastric endocrine cell populations.* Digestion, 1988. 39(2): p. 126-35) and in those with already high levels of gastrin (Zollinger-Ellison syndrome) omeprazole can increase it further to 700 μg/ml (Cadranel, J. F., et al., *[Long-term efficacy and tolerability of omeprazole in 20 patients with severe Zollinger-Ellison syndrome].* Gastroenterol Clin Biol, 1989. 13(8-9): p. 654-62). Omeprazole has been in use for over 20 years and its safety has been tested over time ($LD_50$>4 g/Kg) for the treatment of gastric esophageal reflux disease (GERD) and other peptic diseases. Other proton pump inhibitors such as H2 receptor blocker are also use for the same indication (Schentag, J. J. and T. F. Goss, *Pharmacokinetics and pharmacodynamics of acid-suppressive agents in patients with gastroesophageal reflux disease.* Am J Hosp Pharm, 1993. 50(4 Suppl 1): p. S7-10). Treatment with omeprazole should elevate gastrin level to at least 3 times and in most cases 10 times the normal (Halter, F., et al., *Effect of acid inhibition on the growth of parietal cells.* Scand J Gastroenterol Suppl, 1986. 125: p. 9-13, Hakanson, R., et al., Evidence that gastrin enhances 45Ca uptake into bone through release of a gastric hormone. Regul Pept, 1990. 28(1): p. 107-18, Van Nieuwenhove, Y., et al., *Gastrin stimulates epithelial cell proliferation in the esophagus of rats.* Virchows Arch, 1998. 432(4): p. 371-5, Koop, H., M. Klein, and R. Arnold, *Serum gastrin levels during long-term omeprazole treatment.* Aliment Pharmacol Ther, 1990. 4(2): p. 131-8, Larson, G. M., H. W. Sullivan, and P. Rayford, *Omeprazole-induced hypergastrinemia: role of gastric acidity.* J Surg Res, 1986. 40(5): p. 504-9, Larson, G. M., H. W. Sullivan, and P. L. Rayford, *Relationship of omeprazole-induced hypergastrinemia to gastric pH.* Surgery, 1986. 100(2): p. 175-80, Creutzfeldt, W. and R. Lamberts, *Is hypergastrinaemia dangerous to man?* Scand J Gastroenterol Suppl, 1991. 180: p. 179-91), and this elevation is sustained (Klinkenberg-Knol, E. C., *The role of omeprazole in healing and prevention of reflux disease.* Hepatogastroenterology, 1992. 39 Suppl 1: p. 27-30). Although there are other derivatives of omeprazole, the use of omeprazole has long been tested and the resulting increase in serum gastrin is very consistent. Omeprazole and its derivatives are still the gold standard for comparison of new generations of proton pump inhibitors and the proof of effectiveness of proton pump inhibitor is the increase in serum gastrin level (Yu, K. S., et al., *Pharmacokinetic and pharmacodynamic evaluation of a novel proton pump inhibitor, YH*1885, *in healthy volunteers.* J Clin Pharmacol, 2004. 44(1): p. 73-82). Another embodiment of the present invention relates to the use of native GLP-1 or native EGF formulated with the hydrophobic-core carrier composition of the present invention in combination with proton-pump inhibitor to elevate Gastrin level in the blood to treat insulin-insufficient diabetes by inducing beta-islet cell regeneration.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is GLP-1 and further administering to the patient a proton-pump inhibitor. In further embodiment, the proton pump inhibitor may be omeprazole. In further embodiment, omeprazole is administered at dose of less than 4 g/Kg of patient weight but preferably less than 500 mg/kg of patient and even more preferably less than 100 mg/Kg of patient weight.

Another embodiment the present invention relates to a method of treating a patient for insulin-insufficient diabetes comprising; administering to the patient in need thereof a therapeutically effective amount of any of the hydrophobic-core carrier compositions described above, wherein the load molecule is an Epidermal Growth Factor (EGF) receptor ligand.

Another embodiment the present invention relates to a method of treating a patient for insulin-insufficient diabetes comprising; administering to the patient in need thereof a therapeutically effective amount of any of the hydrophobic-core carrier compositions described above, wherein the load molecule is Epidermal Growth Factor (EGF) receptor ligand and further administering to the patient a proton-pump inhibitor. In further embodiment, the proton pump inhibitor may be omeprazole. In further embodiment, omeprazole is administered at dose of less than 4 g/Kg of patient weight but preferably less than 500 mg/kg of patient and even more preferably less than 100 mg/Kg of patient weight.

Another embodiment the present invention relates to a method of treating a patient for insulin-insufficient diabetes comprising; administering to the patient in need thereof a therapeutically effective amount of any of the hydrophobic-core carrier compositions described above, wherein the load molecule is EGF.

Another embodiment the present invention relates to a method of treating a patient for insulin-insufficient diabetes comprising; administering to the patient in need thereof a therapeutically effective amount of any of the hydrophobic-core carrier compositions described above, wherein the load molecule is GLP-1 and; any of the hydrophobic-core carrier compositions described above, wherein the load molecule is Gastrin Another embodiment the present invention relates to a method of treating a patient for insulin-insufficient diabetes comprising; administering to the patient in need thereof a therapeutically effective amount of any of the hydrophobic-core carrier compositions described above, wherein the load molecule is EGF and further administering to the patient a proton-pump inhibitor. In further embodiment, the proton pump inhibitor may be omeprazole. In further embodiment, omeprazole is administered at dose of less than 4 g/Kg of patient weight but preferably less than 500 mg/kg of patient and even more preferably less than 100 mg/Kg of patient weight.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is TGF-alpha.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is TGF-alpha and further administering to the patient a proton-pump inhibitor. In further embodiment, the proton pump inhibitor may be omeprazole. In further embodiment, omeprazole is administered at dose of less than 4 g/Kg of patient weight but preferably less than 500 mg/kg of patient and even more preferably less than 100 mg/Kg of patient weight.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is Betacellulin.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is Betacellulin and further administering to the patient a proton-pump inhibitor. In further embodiment, the proton pump inhibitor may be omeprazole. In further embodiment, omeprazole is administered at dose of less than 4 g/Kg of patient weight but preferably less than 500 mg/kg of patient and even more preferably less than 100 mg/Kg of patient weight.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is Gastrin/Cholecystokinin receptor ligand.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is Gastrin.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is Gastrin and further administering to the patient a proton-pump inhibitor. In further embodiment, the proton pump inhibitor may be omeprazole. In further embodiment, omeprazole is administered at dose of less than 4 g/Kg of patient weight but preferably less than 500 mg/kg of patient and even more preferably less than 100 mg/Kg of patient weight. The combination of hydrophobic-core carrier compositions containing Gastrin and omeprazole will reduce the required dose of hydrophobic-core carrier compositions containing Gastrin.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is Cholecystokinin.

Another embodiment the present invention relates to a method of treating a patient for insulin-insufficient diabetes comprising administering to the patient in need thereof a therapeutically effective amount of any of the hydrophobic-core carrier compositions described above, wherein the load molecule is Cholecystokinin and further administering to the patient a proton-pump inhibitor. In further embodiment, the proton pump inhibitor may be omeprazole. In further embodiment, omeprazole is administered at dose of less than 4 g/Kg of patient weight but preferably less than 500 mg/kg of patient and even more preferably less than 100 mg/Kg of patient weight. The combination of hydrophobic-core carrier compositions containing Cholecystokinin and omeprazole will reduce the required dose of hydrophobic-core carrier compositions containing Cholecystokinin.

It is the intention of the present invention to provide a method of treatment of various diseases described in the "The Merk Manual of Diagnosis and Therapy" (published 1992 by Merck Laboratories which is a division of Merck & Co., Inc, Rahway, N.J.) using compositions described in the present invention along with appropriate load molecule selected from that described in PDR or Physician Desk Reference (published 2001 by Medical Economics Company, Inc. Montvale, N.J.). The Merk Manual of Diagnosis and Therapy and the PDR are hereby incorporated by reference. The appropriateness of a load molecule for particular disease can be ascertained by checking "The Merk Manual of Diagnosis and Therapy" or the PDR.

EXEMPLIFICATION

Synthetic Method Overview

Hydrophobic-core carriers of the present invention include a central carrier chain, a hydrophobic group, a protecting group, and, optionally, a targeting group. Each group is linked together and the hydrophobic group is capable of forming reversible linkages with a load molecule such as a drug, therapeutic agent, or diagnostic agent. The reversible linkage between the hydrophobic-core carrier and a load molecule includes a hydrophobic interaction.

The synthesis of a hydrophobic-core carrier load molecule complex from a polymeric carrier containing amino, carboxyl, or hydroxyl groups generally involves three synthetic stages: 1) covalent modification of a back bone carrier with protective chains; 2) modification of the product from step 1) with hydrophobic groups, such as, for example, palmitic acid; and 3) incubating the product from step 2) with a load molecule, such as, for example, incubation with GLP-1 to achieve formation of a hydrophobic-core carrier-GLP-1 complex.

Example 1

Preparation of N-Hydroxysuccinamide Esters of Fatty Acids and Aromatic-Alkyl Carboxylic Acids The N-hydroxysuccinamide esters of fatty and aromatic-alkyl carboxylic acids will facilitate the synthesis of hydrophobic-core carriers of the present invention since these esters react readily with amino groups along the carrier. The following method was taken from Lapidot et al. [Lapidot, Y., Rappoport, S. and Wolman, Y. (1967) J. Lipid Res., 8, 142]:

(i) prepare a 230 mM solution of N-hydroxysuccinimide by dissolving 3.45 g (30 nmol) in 30 ml of ethyl acetate dried over molecular sieve pellets in a stoppered 250-ml glass conical flask; (ii) to the above solution add 30 nmol of desired fatty acid; (iii) prepare a solution containing 30 mmol (6.18 g of dicyclohexyl carbodiimide in 10 ml ethyl acetate, and add it to the solution of fatty acid; (iv) allow the reaction to proceed overnight at room temperature; (v) remove the precipitated dicyclohexyl urea by filtration using a suction tap; (vi) evaporate the filtrate to dryness on a rotary evaporator, and purify it by re-crystallization from ethanol; and (vii) check the purity by TLC, using the solvent system: (a) chloroform, (b) petroleum (b.p. 40-60° C.)-diethyl ether, 8:2. Stain for N-hydroxysuccinimide and ester (red color) by spraying with 10% hydroxylamine in 0.1M NaOH, followed after 2 min by 5% $FeCl_3$ in 1.2 M HCl. Yields of 80-90% can be obtained.

Other activated fatty acids and aromatic alkyl carboxylic acids are commercially available (for example from Sigma-Aldrich Chem. Co., St Louis, Mo.) in the form of fatty acid anhydride, fatty acyl-halide, aromatic-alkyl-carboxyl-anhydride, or aromatic-alkyl-acyl-halide (such a -acyl-Cl and -acyl-Br). For example stearic anhydride will react spontaneously with amino groups of the carrier to form amide bonds attaching the $CH_3(CH_2)_{16}CO—$ of the stearic anhydride and releasing the other portion of stearic anhydride as stearic acid. Neutralization of stearic acid product with basic buffer will help drive the reaction to completion. A similar reaction can be done using benzoic anhydride to attach hydrophobic phenyl groups to the carrier. Similarly, alkyl-acyl-halide or benzyl-alkyl-acyl-halide will react with amino groups or, when heated, with hydroxyl groups as well. This will allow addition of hydrophobic group to the carrier.

Example 2

Synthesis of MPEG-poly-L-lysine (5000; 40,000; 73%) (PLPEG-I)

Figure 9:
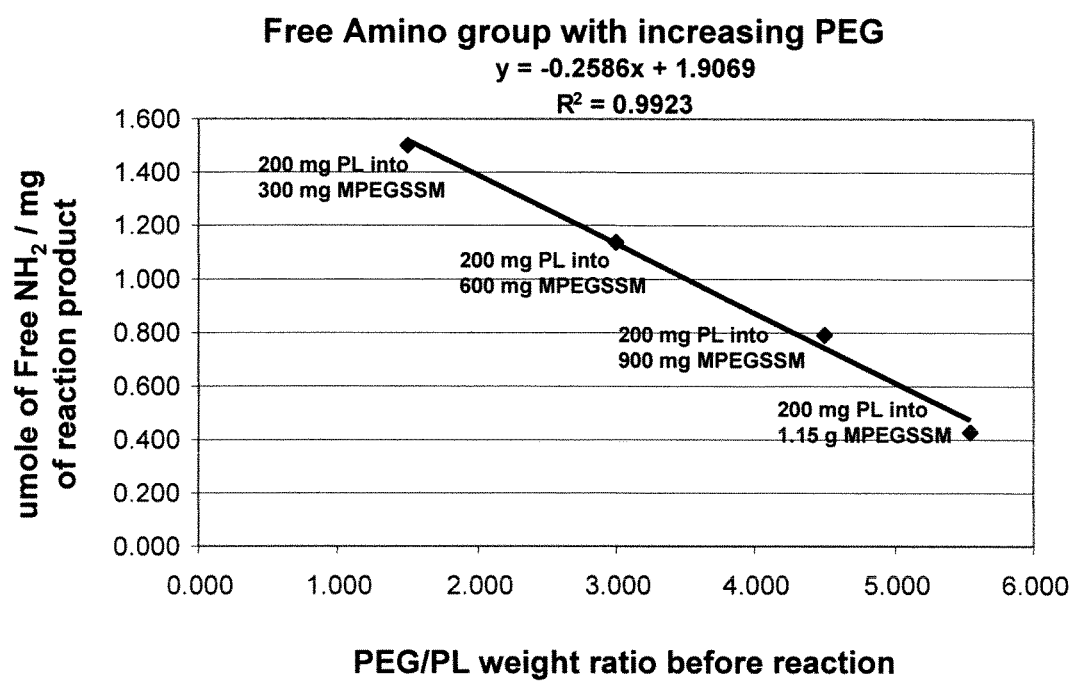
FIG. 9 depicts the graph of free epsilon amino groups in the polylysine (PL) per mg of product after reacting some of the epsilon amino groups with various concentration of MPEG. The y-axis is the amount of free epsilon amino groups per mg of product (PLPEG) and the x-axis is the ratio of the reactants (PEG and PL) prior to the reaction.

The reagents, MPEG-succinimdyl-succinate and polylysine, are commercially available and their syntheses are well known in the art. Poly-L-lysine (200 mg; Polylysine Hydrobromide; Sigma chemical Co.; DPvis: 264; MWvis: 55,200; DPmalls: 190; MWmalls: 39,800; 0.7 mmoles aminogroup by TNBS assay Sparado et al. Anal Biochem 96:317, 1979) was dissolved in 10 ml of 0.1M carbonate buffer pH 8.35 and 1150 mg of MPEG-succinimdyl-succinate was added, vortexed, and incubated overnight at room temperature. The next day, aliquots were taken and the amount of amino groups remaining was quantified using trinitrobenzenesulfonic acid (Sparado et al. Anal Biochem 96:317, 1979). The result indicated that 73% of amino group had been conjugated to MPEG. To cap the carboxyl terminal of polylysine that can potentially interfere with the next reaction (addition of hydrophobic group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 860 mg. The resulting product has an estimated Mw of 730 kDa based on the number of amino groups that had been derivatized by MPEG. The number of free amino groups per mg of final product is 0.43 umole/mg (FIG. 9). It should be noted that if MPEG-succinimdyl-succinate used is contaminated with free succinate, which is quite common, the amount of PEG will be less than what is expected from the amino group analysis and will be inconsistent with the amount of amino group per mg of final product.

Example 3

Synthesis of MPEG-Poly-L-Lysine (5000; 40,000; 55%) (PLPEG-II)

The reagents, MPEG-succinimdyl-succinate and polylysine, are commercially available and their syntheses are well known in the art. Poly-L-lysine (200 mg; Polylysine Hydrobromide; Sigma chemical Co.; DPvis:264; MWvis: 55,200; DPmalls: 190; MWmalls: 39,800; 0.7 mmoles aminogroup by TNBS assay Sparado et al. Anal Biochem 96:317, 1979) was dissolved in 10 ml of 0.1 M carbonate buffer pH 8.35 and 900 mg of MPEG-succinimdyl-succinate was added, vortexed, and incubated overnight at room temperature. The next day, aliquots were taken and the amount of amino groups remaining was quantified using trinitrobenzenesulfonic acid (Sparado et al. Anal Biochem 96:317, 1979). The result indicated that 55% of the amino groups had been conjugated to MPEG. To cap the carboxyl terminal of polylysine that can potentially interfere with the next reaction (addition of hydrophobic group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 860 mg. The resulting product has an estimated Mw of 560 kDa based on the number of amino groups that had been derivatized by MPEG. The number of free amino groups per mg of final product is 0.795 umole/mg (FIG. 9). It should be noted that if MPEG-succinimdyl-succinate used is contaminated with free succinimdyl-succinate, the amount of PEG will be less than what is expected from the amino group analysis and will be inconsistent with the amount of amino group per mg of final product.

Example 4

Synthesis of MPEG-Poly-1-Lysine (5000; 40,000; 22%) (PLPEG-III)

The reagents, MPEG-succinimdyl-succinate and polylysine, are commercially available and their syntheses are well known in the art. Poly-L-lysine (200 mg; Polylysine Hydrobromide; Sigma chemical Co.; DPvis: 264; MWvis: 55,200; DPmalls: 190; MWmalls: 39,800; 0.7 mmoles aminogroup by TNBS assay Sparado et al. Anal Biochem 96:317, 1979) was dissolved in 10 ml of 0.1 M carbonate buffer pH 8.35 and 600 mg of MPEG-succinimdyl-succinate was added, vortexed, and incubated overnight at room temperature. The next day, aliquots were taken and the amount of amino groups remaining was quantified using trinitrobenzenesulfonic acid (Sparado et al. Anal Biochem 96:317, 1979). The result indicated that 22% of amino groups had been conjugated to MPEG. To cap the carboxyl terminal of polylysine that can potentially interfere with the next reaction (addition of hydrophobic group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 320 mg. The resulting product has an estimated Mw of 250 kDa based on the number of amino groups that had been derivatized by MPEG. The number of free amino groups per mg of final product is 1.14 umole/mg (FIG. 9). It should be noted that if MPEG-succinimdyl-succinate used is contaminated with free succinimdyl-succinate, the amount of PEG will be less than what is expected from the amino group analysis and will be inconsistent with the amount of amino group per mg of final product.

Example 5

Synthesis of MPEG-Poly-1-Lysine (5000; 40,000; 9%) (PLPEG-IV)

The reagents, MPEG-succinimdyl-succinate and polylysine, are commercially available and their syntheses are well known in the art. Poly-L-lysine (200 mg; Polylysine Hydrobromide; Sigma chemical Co.; DPvis: 264; MWvis: 55,200; DPmalls: 190; MWmalls: 39,800; 0.7 mmoles aminogroup by TNBS assay Sparado et al. Anal Biochem 96:317, 1979) was dissolved in 10 ml of 0.1 M carbonate buffer pH 8.35 and 300 mg of MPEG-succinimdyl-succinate was added, vortexed, and incubated overnight at room temperature. The next day, aliquots were taken and the amount of amino group remaining was quantified using trinitrobenzenesulfonic acid (TNBS) (Sparado et al. Anal Biochem 96:317, 1979). The result indicated that 9% of amino groups had been conjugated to MPEG. To cap the carboxyl terminal of polylysine that can potentially interfere with the next reaction (addition of hydrophobic group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 300 mg. The resulting product has an estimated Mw of 125 kDa based on the number of amino groups that had been derivatized by MPEG. The number of free amino groups per mg of final product is 1.5 umole/mg (FIG. 9). It should be noted that if MPEG-succinimdyl-succinate used is contaminated with free succinimdyl-succinate, the amount of PEG will be less than what is expected from the amino group analysis and will be inconsistent with the amount of amino group per mg of final product.

Example 6

Synthesis of MPEG-Poly-1-Lysine-C12 (PLPEG-III-C12)

PLPEG-III-C12 is a hydrophobic-core carrier containing $CH_3(CH_2)_{10}CO$— hydrophobic groups attached to the epsilon amino group of the remaining lysine residues. Twenty mg of PLPEG-III from Example 4 was dissolved to 2 ml with 0.1 M carbonate buffer pH 8.35. Fifty mg of lauric acid, sodium salt (Acros Organics, N.J.), was dissolved with 2 ml of 30% acetonitrile:water and to this solution 25 mg of NHSS(N-hydroxysuccinimide sulfate; Pierce, Rockford, Ill.) was added followed by 100 mg of EDC (1-ethyl-3-[3-dimethylaminopropyl]carbodiimide hydrochloride; Pierce, Rockford, Ill.). This solution was added drop-wise to the 2 ml solution of PLPEG-III, and incubated at room temperature. The next day, aliquots were taken and the amount of amino group remaining was quantified using trinitrobenzenesulfonic acid (NBS) (Sparado et al. Anal Biochem 96:317, 1979). The result indicated that no free amino groups were remaining. The remaining soluble fatty acids and NHSS are removed by passing the solution through 2 ml anion exchange resin (Mono-Q, Bio-Rad, Hercules, Calif.) equilibrated with 50% acetonitrile water. The eluent was then desalted on 20 ml Superdex 200 (Amersham Biosciences Corp, Westborough, Mass.) equilibrated with 50% Acetonitrile/water and the void volume containing PLPEG-III-C12 was lyophilized and weighed giving a yield of 12 mg.

Example 7

Synthesis of MPEG-Poly-1-Lysine-C18 (PLPEG-III-C18)

PLPEG-III-C18 is a hydrophobic-core carrier containing $CH_3(CH_2)_{16}CO$— hydrophobic group attached to the epsilon amino group of the remaining lysine residues. Twenty mg of PLPEG-III from Example 4 was increased to 2 ml with 0.1 M carbonate buffer pH 8.35. Fifty mg of stearic acid, sodium salt (Fisher, Houston, Tex.), was dissolved with 2 ml of acetonitrile and to this solution 25 mg of NHSS(N-hydroxysuccinimide sulfate; Pierce, Rockford, Ill.) was added followed by 100 mg of EDC (1-ethyl-3-[3-dimethylaminopropyl]carbodiimide hydrochloride; Pierce, Rockford, Ill.). This was added drop wise to the 2 ml solution of PLPEG-III, and incubated at room temperature. The next day, aliquots were taken and the amount of amino groups remaining was quantified using trinitrobenzenesulfonic acid (TNBS) (Sparado et al. Anal Biochem 96:317, 1979). The result indicated that no free amino groups were remaining. The remaining soluble fatty acids and NHSS are removed by passing the solution through 2 ml anion exchange resin (Mono-Q, Bio-Rad, Hercules, Calif.) equilibrated with 50% acetonitrile water. The eluent was then desalted on 20 ml Superdex 200 (Amersham Biosciences Corp, Westborough, Mass.) equilibrated with 50% Acetonitrile/water and the void volume containing PLPEG-III-C18 was lyophilized and weighed giving a yield of 18 mg.

Example 8

Synthesis of MPEG-poly-1-lysine-C8 (PLPEG-III-C8)

PLPEG-III-C8 is a hydrophobic-core carrier containing $CH_3(CH_2)_6CO$— hydrophobic group attached to the epsilon amino group of the remaining lysine residues. Twenty mg of PLPEG-III from Example 4 was increased to 2 ml with 0.1 M carbonate buffer pH 8.35. Fifty mg of caprylic acid, sodium salt (Sigma chemical Co. St. Louis, Mo.), was dissolved with 2 ml of 30% acetonitrile:water and to this solution 25 mg of NHSS(N-hydroxysuccinimide sulfate; Pierce, Rockford, Ill.) was added followed by 100 mg of EDC (1-ethyl-3-[3-dimethylaminopropyl]carbodiimide hydrochloride; Pierce, Rockford, Ill.). This was added drop-wise to the 2 ml solution of PLPEG-III, and incubated at room temperature. The next day, aliquots were taken and the amount of amino groups remaining was quantified using trinitrobenzenesulfonic acid (NBS) (Sparado et al. Anal Biochem 96:317, 1979). The result indicated that no free amino groups were remaining. The remaining soluble fatty acids and NHSS are removed by passing the solution through 2 ml anion exchange resin (Mono-Q, Bio-Rad, Hercules, Calif.) equilibrated with 50% acetonitrile water. The eluent was then desalted on 20 ml Superdex 200 (Amersham Biosciences Corp, Westborough, Mass.) equilibrated with 50% Acetonitrile/water and the void volume containing PLPEG-III-C8 was lyophilized and weighed giving a yield of 8 mg.

Example 9

Synthesis of MPEG-Poly-1-Lysine-C12 (PLPEG-II-C12)

PLPEG-II-C12 is a hydrophobic-core carrier containing $CH_3(CH_2)_{10}CO$— hydrophobic group attached to the epsilon amino group of the remaining lysine residues. Forty mg of PLPEG-II from Example 3 was increased to 4 ml with 0.1 M carbonate buffer pH 8.35. Fifty mg of lauric acid, sodium salt (Acros Organics, N.J.), was dissolved in 2 ml of 30% acetonitrile:water and to this solution 25 mg of NHSS(N-hydroxysuccinimide sulfate; Pierce, Rockford, Ill.) was added followed by 100 mg of EDC (1-ethyl-3-[3-dimethyl-aminopropyl]carbodiimide hydrochloride; Pierce, Rockford, Ill.). This was added drop-wise to the 4 ml solution of PLPEG-III, and incubated at room temperature. The next day, aliquots were taken and the amount of amino groups remaining was quantified using trinitrobenzenesulfonic acid (NBS) (Sparado et al. Anal Biochem 96:317, 1979). The result indicated that no free amino groups were remaining. The remaining soluble fatty acids and NHSS are removed by passing the solution through 2 ml anion exchange resin (Mono-Q, Bio-Rad, Hercules, Calif.) equilibrated with 50% acetonitrile:water. The eluent was then desalted on 20 ml Superdex 200 (Amersham Biosciences Corp, Westborough, Mass.) equilibrated with 50% Acetonitrile/water and the void volume containing PLPEG-II-C12 was lyophilized and weighed giving a yield of 25 mg.

Example 10

Binding of GLP-1 to PLPEG-II-C12

Figure 10:
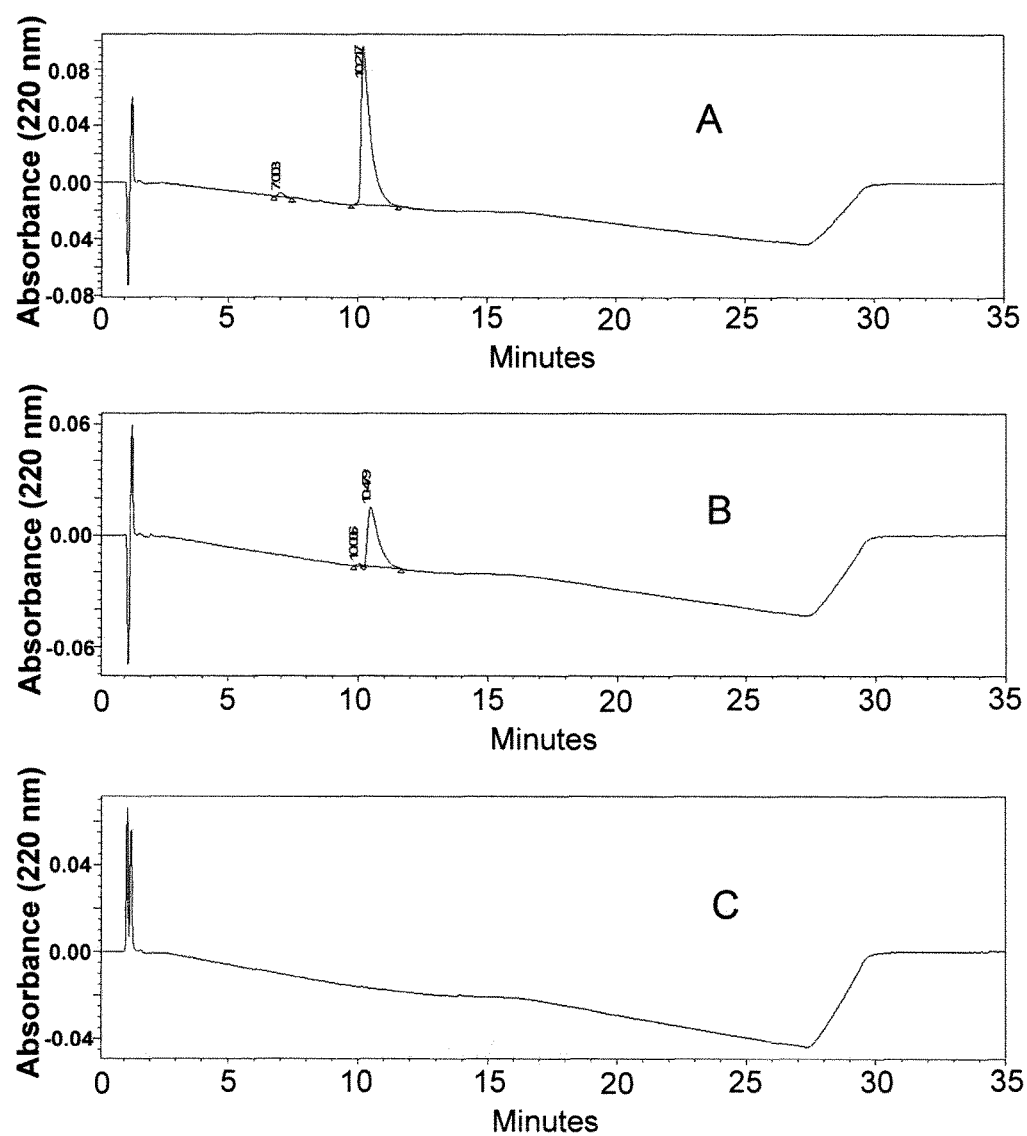
FIG. 10 depicts the HPLC tracings of the free GLP-1 after incubation with the PLPEG-III-C12 and PLPEG-III; A) Total GLP-1 is 180 µg in 0.5 ml of PBS. This is a 50 µl injection of GLP-1 passed through 100 kDa filter. Total available GLP-1 for binding to the carrier is 144 µg; B) a 50 µl injection of GLP-1 that did not bind to 450 µg PLPEG carrier. Non-binding GLP-1 passed through 100 kDa filter. Total GLP-1 that did not bind is 55 µg. Total capacity of PLPEG without C12 is 89 µg or 20% of its weight; C) this is a 50 µl injection of GLP-1 that did not bind to 450 µg C12-PLPEG carrier. Non-binding GLP-1 should pass through 100 kDa filter. Total GLP-1 that did not bind is 0 µg. Total capacity of 450 µg C12-PLPEG is at least 144 µg (all available). The tracings demonstrate that the presence of hydrophobic moieties in the hydrophobic-core carrier increase the binding of load molecules (in this case GLP-1) to the carrier.
Figure 11:
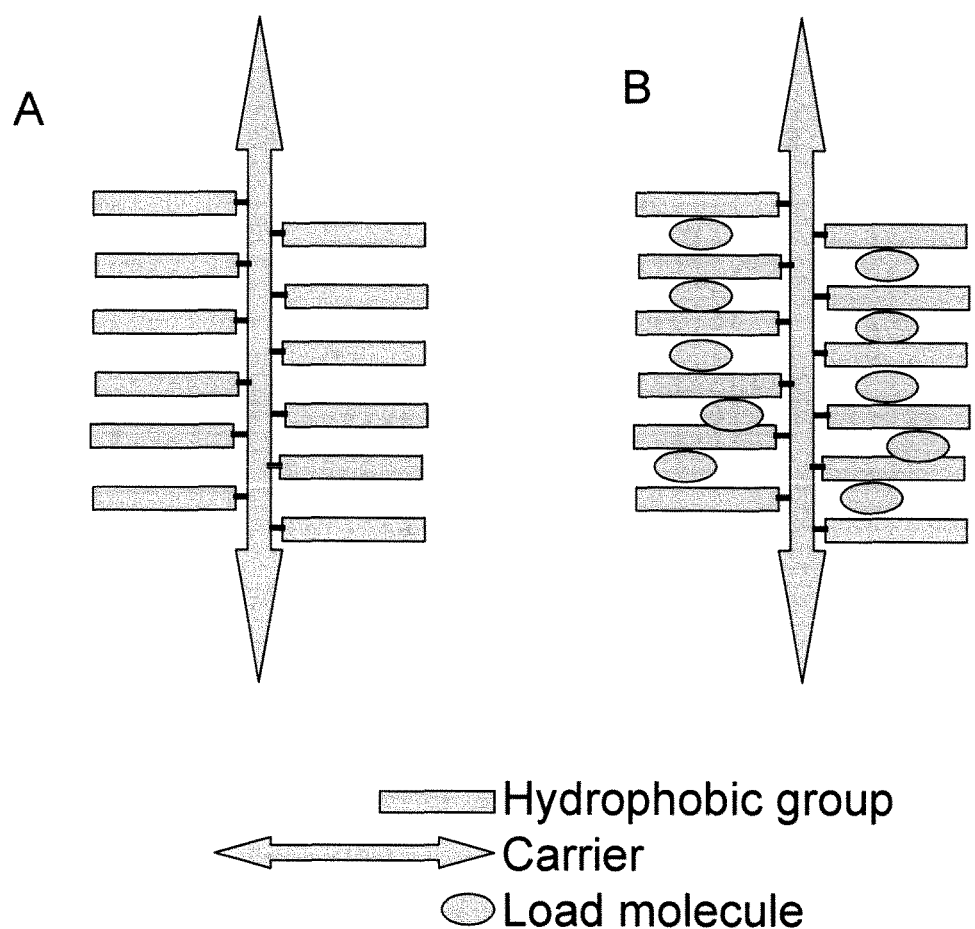
FIG. 11 depicts a diagram of two embodiments of the hydrophobic-core composition of the present invention comprising a carrier, a hydrophobic group, with (B) and without (A) load molecule.
Figure 12:
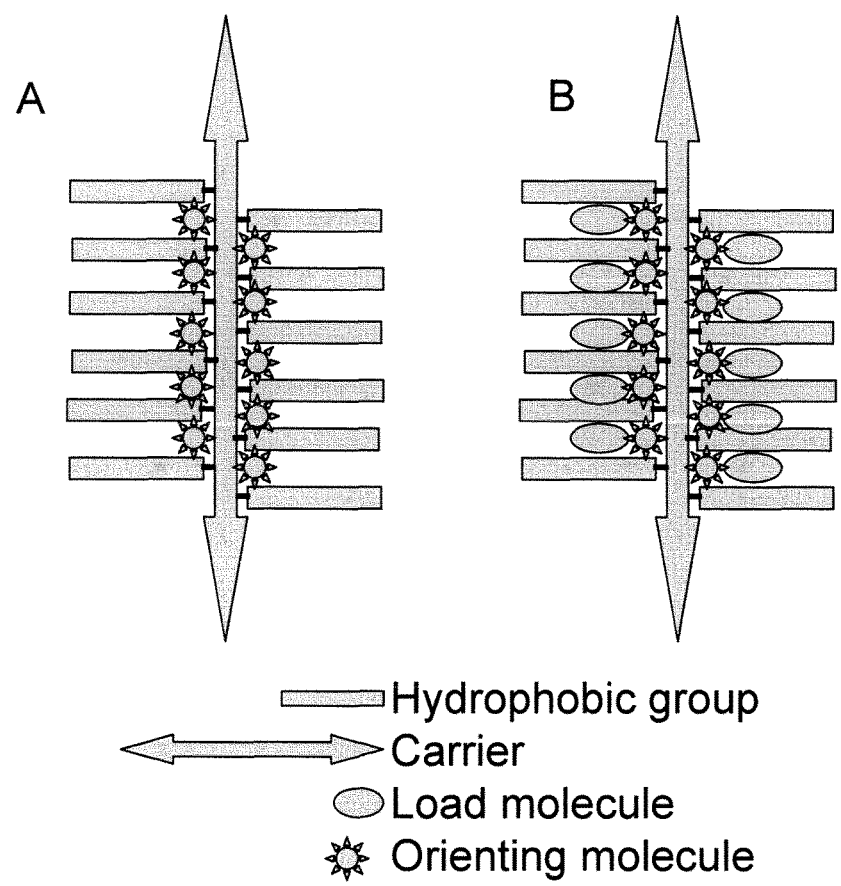
FIG. 12 depicts a diagram of two embodiments of the hydrophobic-core composition of the present invention comprising a carrier, a hydrophobic group, an orienting molecule, with (B) and without (A) load molecule.
Figure 13:
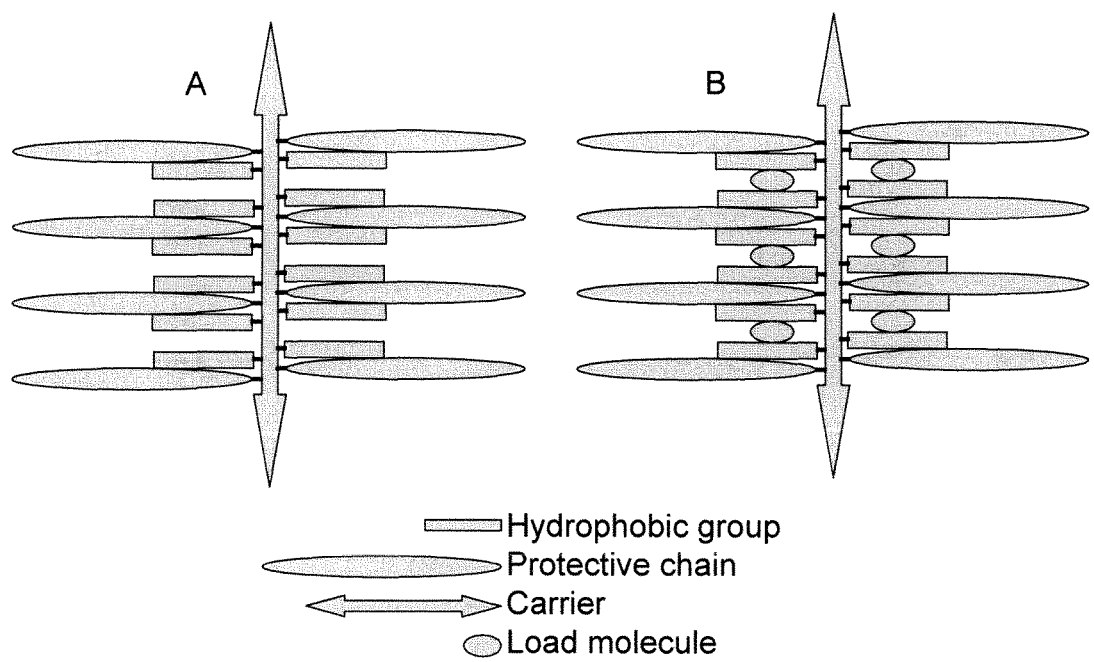
FIG. 13 depicts a diagram of two embodiments of the hydrophobic-core composition and without (A) load molecule, wherein the hydrophobic groups are bonded to the carrier independently of the protective groups. The density of hydrophobic moieties in the core of this composition will not be as high as when all the sites on the carrier are occupied by hydrophobic groups.
Figure 14:
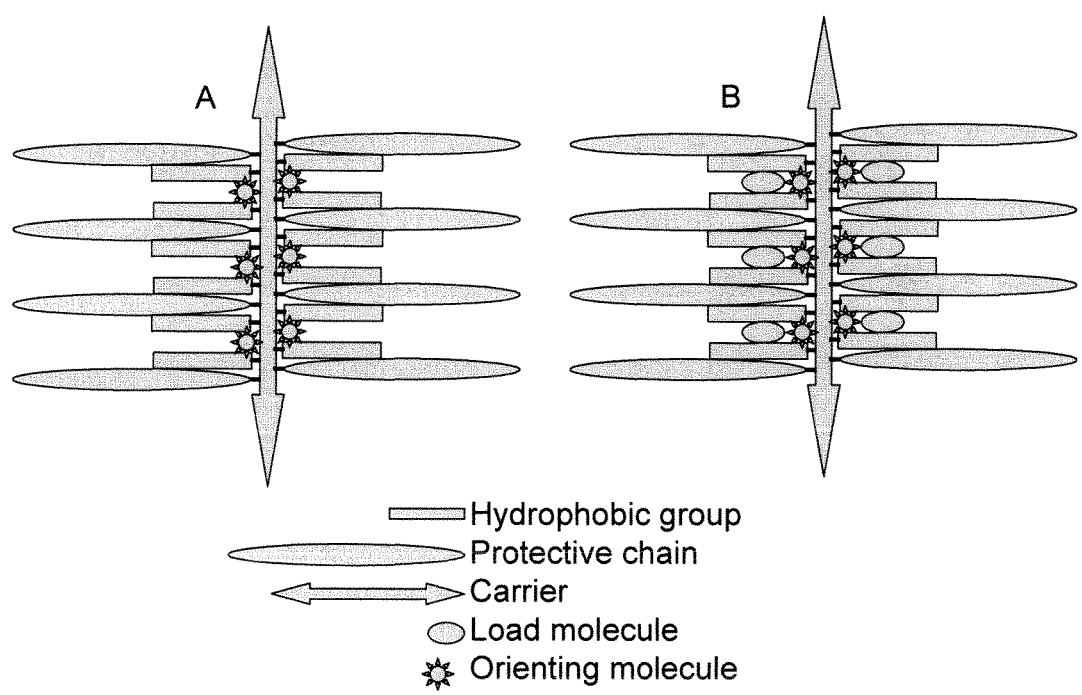
FIG. 14 depicts a diagram of two embodiments of the hydrophobic-core composition of the present invention comprising a carrier, a protective chain, a hydrophobic group, an orienting molecule, with (B) and without (A) load molecule, wherein the hydrophobic groups are bonded directly to the carrier independently of the protective groups. The density of hydrophobic groups in the core of this composition will not be as high as when all the sites on the carrier are occupied by hydrophobic moieties.
Figure 15:
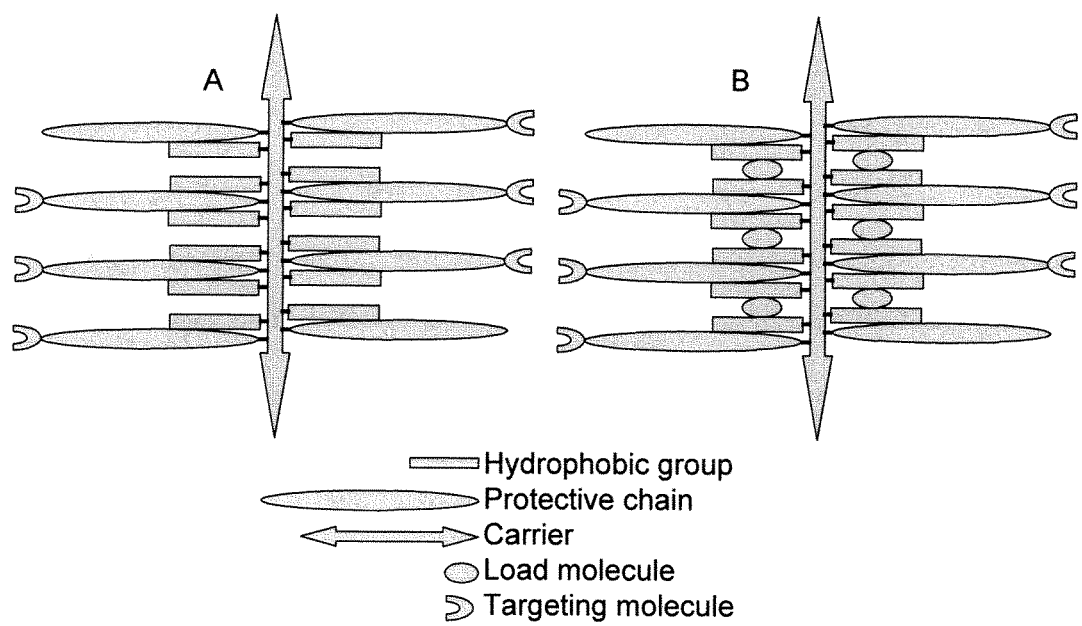
FIG. 15 depicts a diagram of two embodiments of the hydrophobic-core composition of the present invention comprising a carrier, a protective chain, a targeting molecule, a hydrophobic group, with (B) and without (A) load molecule wherein the hydrophobic groups are bonded to the carrier independently of the protective groups. The density of hydrophobic groups on the carrier will not be as high as when all the sites in the core are occupied by hydrophobic groups.
Figure 16:
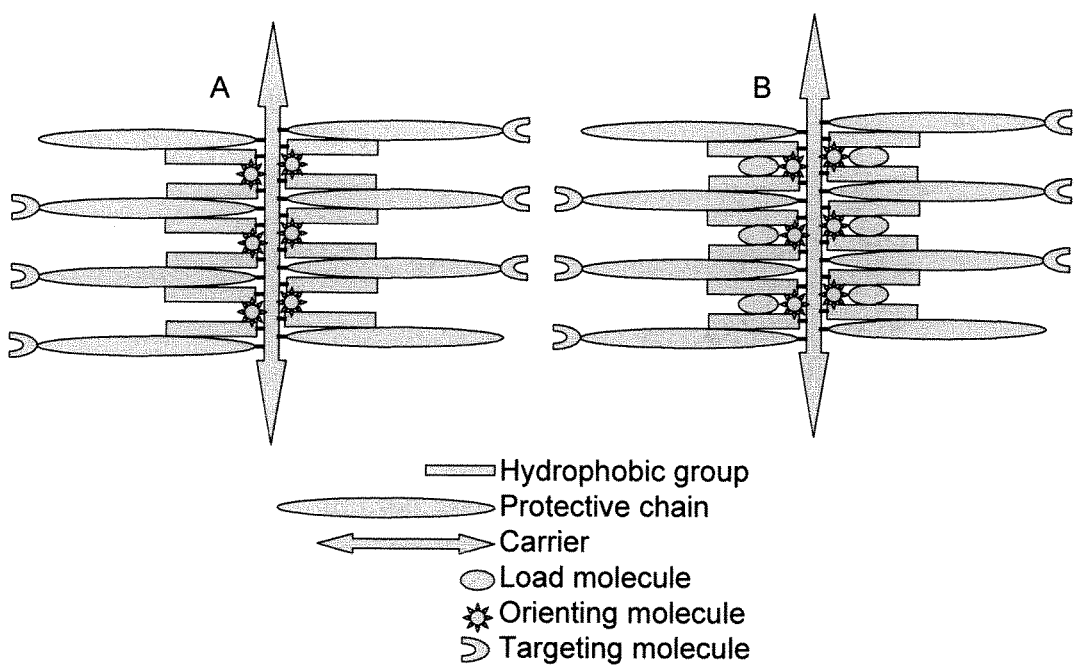
FIG. 16 depicts a diagram of two embodiments of the hydrophobic-core composition of the present invention comprising a carrier, a protective chain, a targeting molecule, a hydrophobic group, an orienting molecule, with (B) and without (A) load molecule wherein the hydrophobic groups are bonded to the carrier independently of the protective groups. The density of hydrophobic groups on the carrier will not be as high as when all the sites of the carrier are occupied by hydrophobic moieties.
Figure 17:
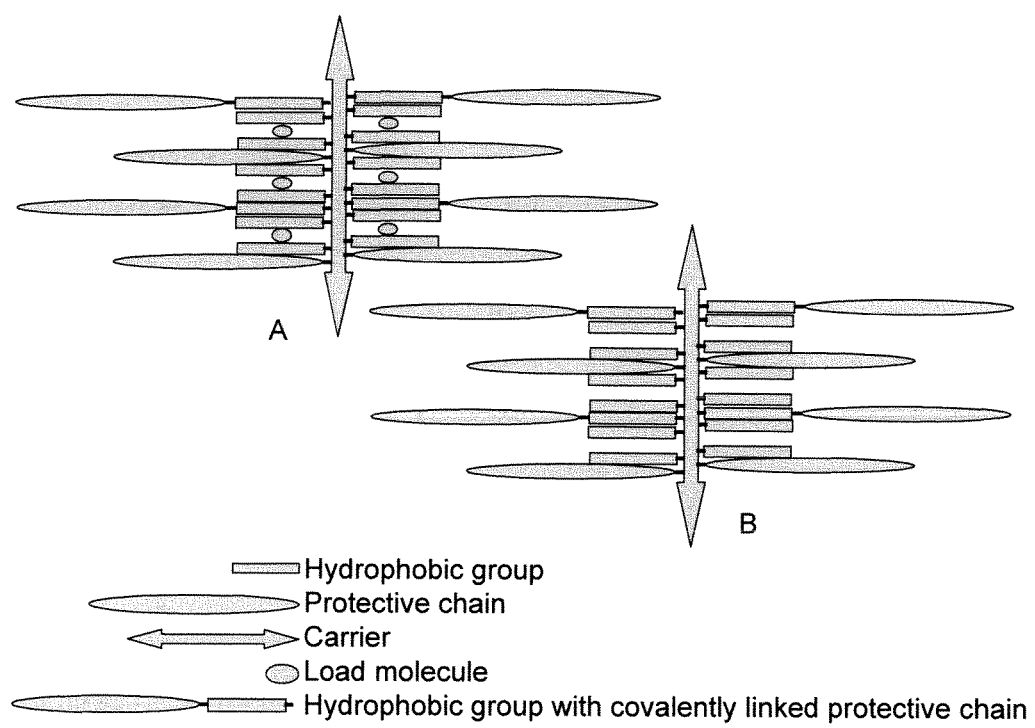
FIG. 17 depicts a diagram of two embodiments of the hydrophobic-core composition of the present invention comprising a carrier, a protective chain bonded directly to the carrier, a hydrophobic group with a covalently linked protective chain, a hydrophobic group without a covalently linked protective chain, with (A) and without (B) load molecule.
Figure 18:
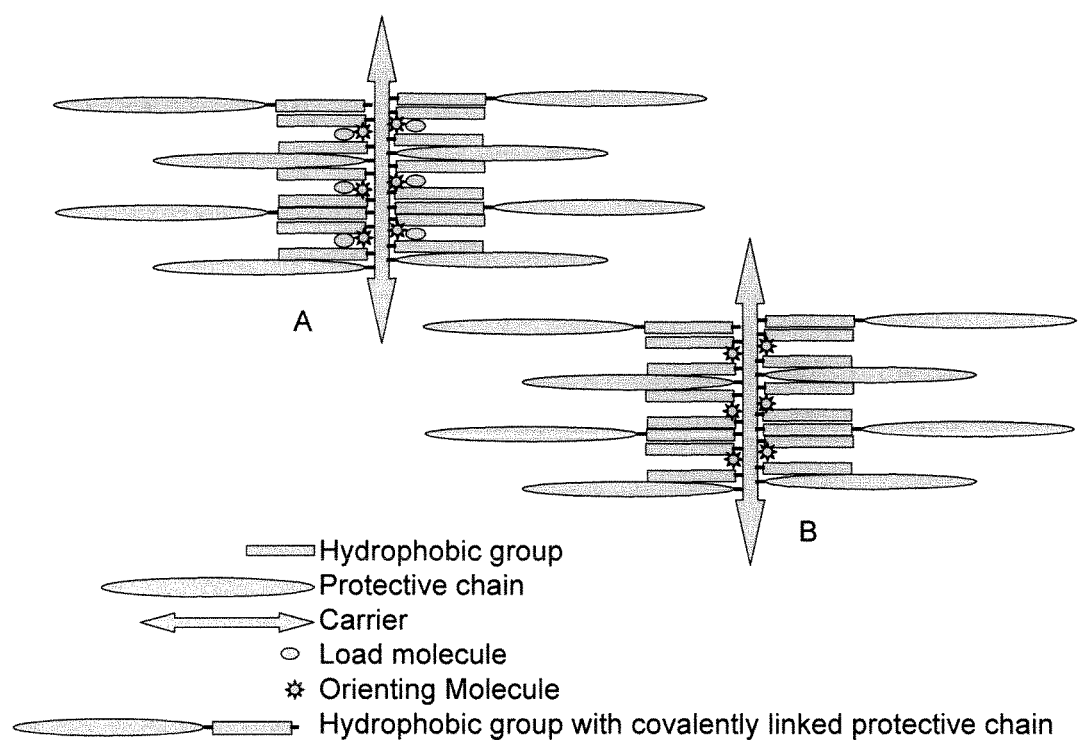
FIG. 18 depicts a diagram of two embodiments of the hydrophobic-core composition of the present invention comprising a carrier, a protective chain bonded directly to the carrier, a hydrophobic group with a covalently linked protective chain, a hydrophobic group, an orienting molecule with (A) and without (B) load molecule.
Figure 19:
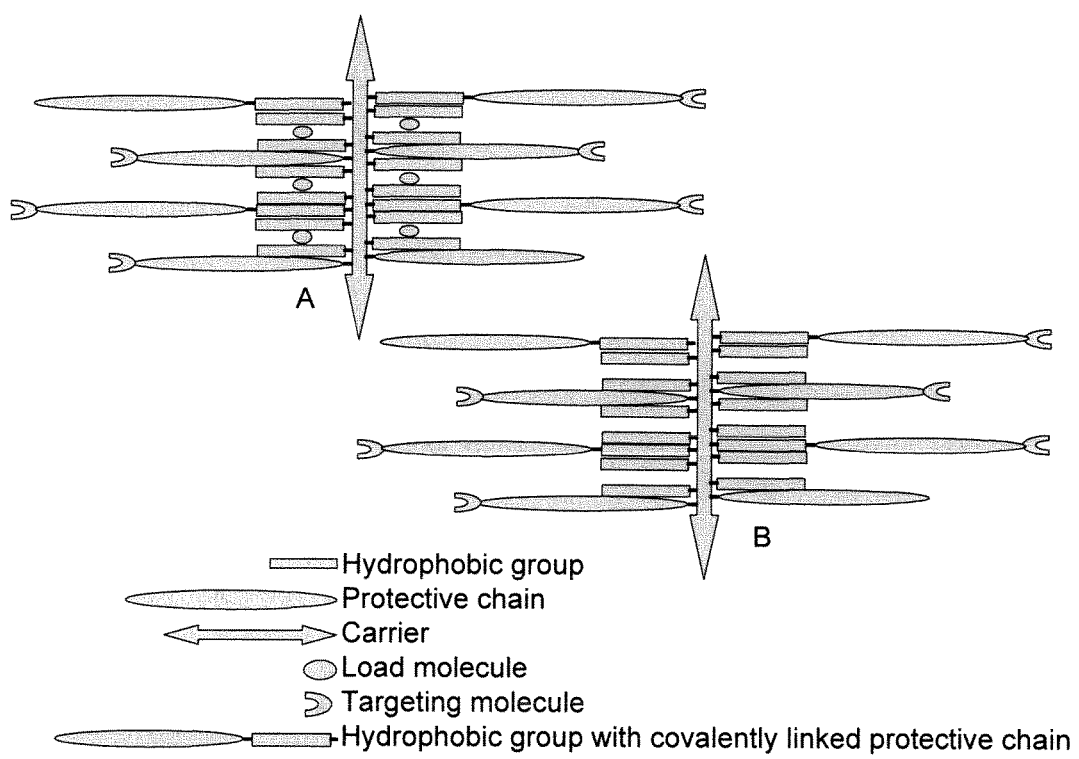
FIG. 19 depicts a diagram of two embodiments of the hydrophobic-core composition of the present invention comprising a carrier, a protective chain bonded directly to the carrier, a hydrophobic group with a covalently linked protective chain, a targeting molecule, a hydrophobic group without covalently linked protective chain, with (A) and without (B) load molecule.
Figure 20:
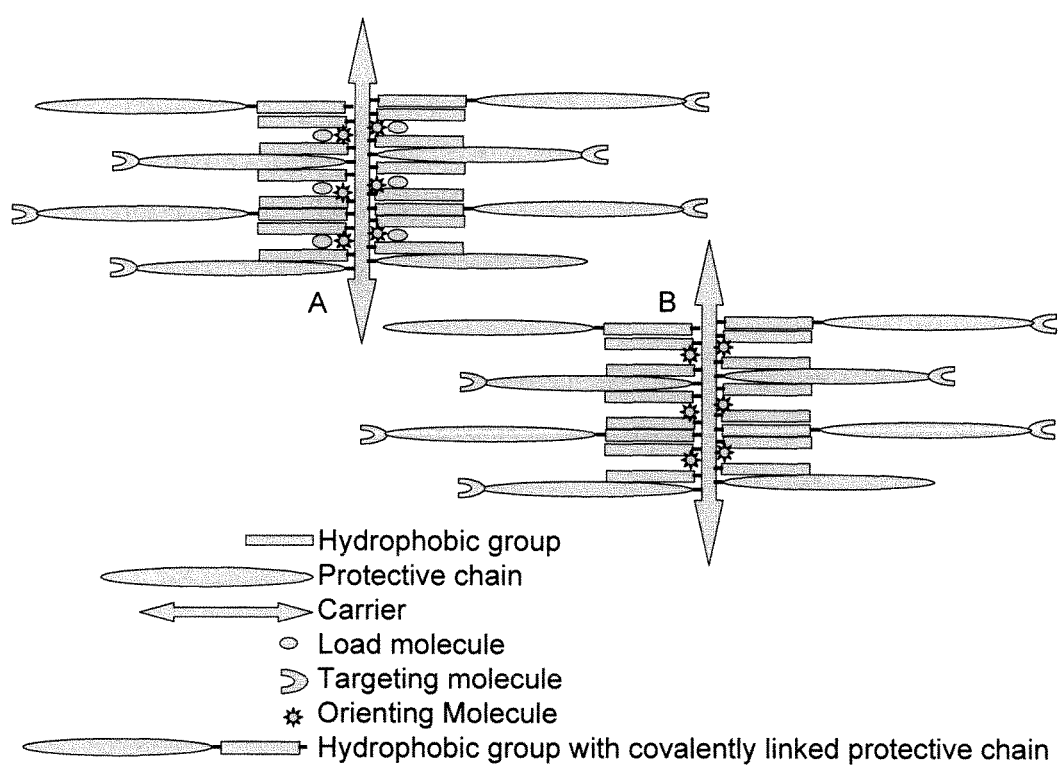
FIG. 20 depicts a diagram of two embodiments of the hydrophobic-core composition of the present invention comprising a carrier, a protective chain bonded directly to the carrier, a hydrophobic group with a covalently linked protective chain, a targeting molecule, a hydrophobic group without covalently linked protective chain, an orienting molecule, with (A) and without (B) load molecule.
Figure 21:
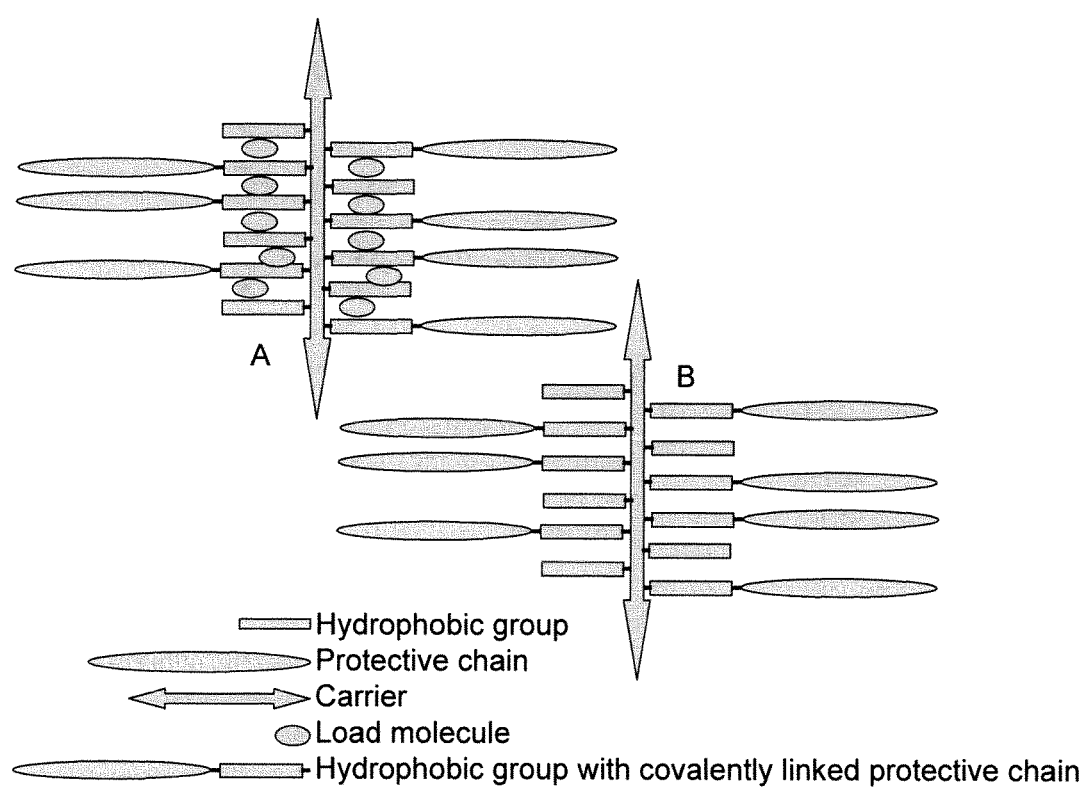
FIG. 21 depicts a diagram of two embodiments of the hydrophobic-core composition of the present invention comprising a carrier, a hydrophobic group with a covalently linked protective chain, a hydrophobic group without covalently linked protective chain, with (A) and without (B) load molecule.
Figure 22:
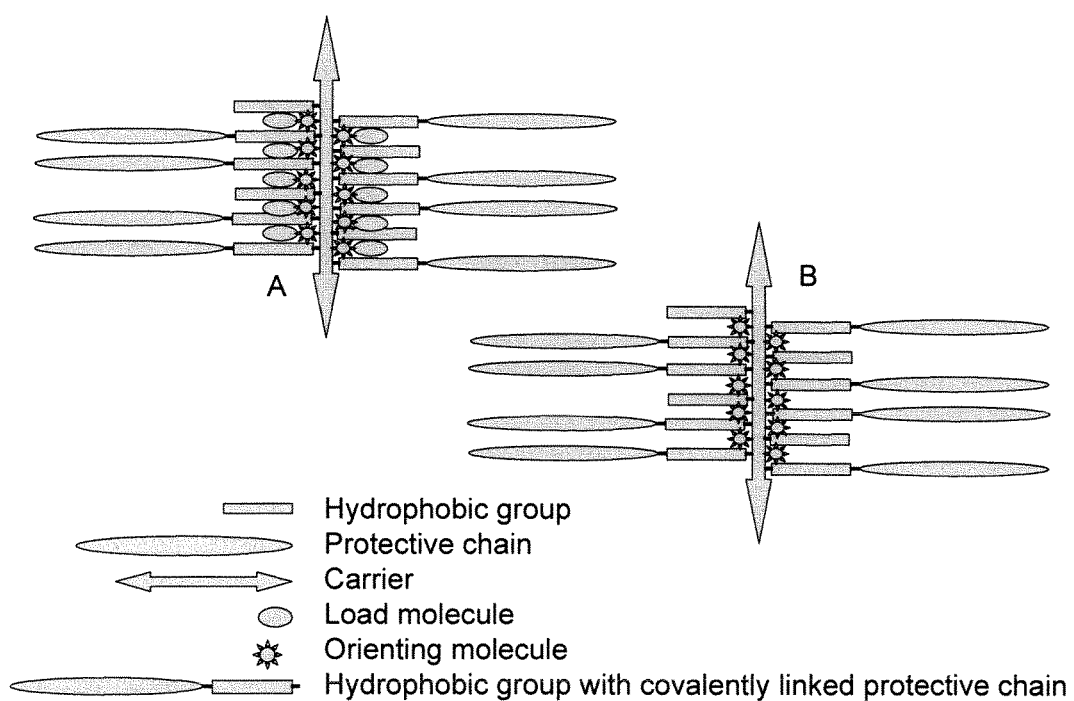
FIG. 22 depicts a diagram of two embodiments of the hydrophobic-core composition of the present invention comprising a carrier, a hydrophobic group with a covalently linked protective side chain, a hydrophobic group without a covalently linked protective chain, an orienting molecule, with (A) and without (B) load molecule.
Figure 23:
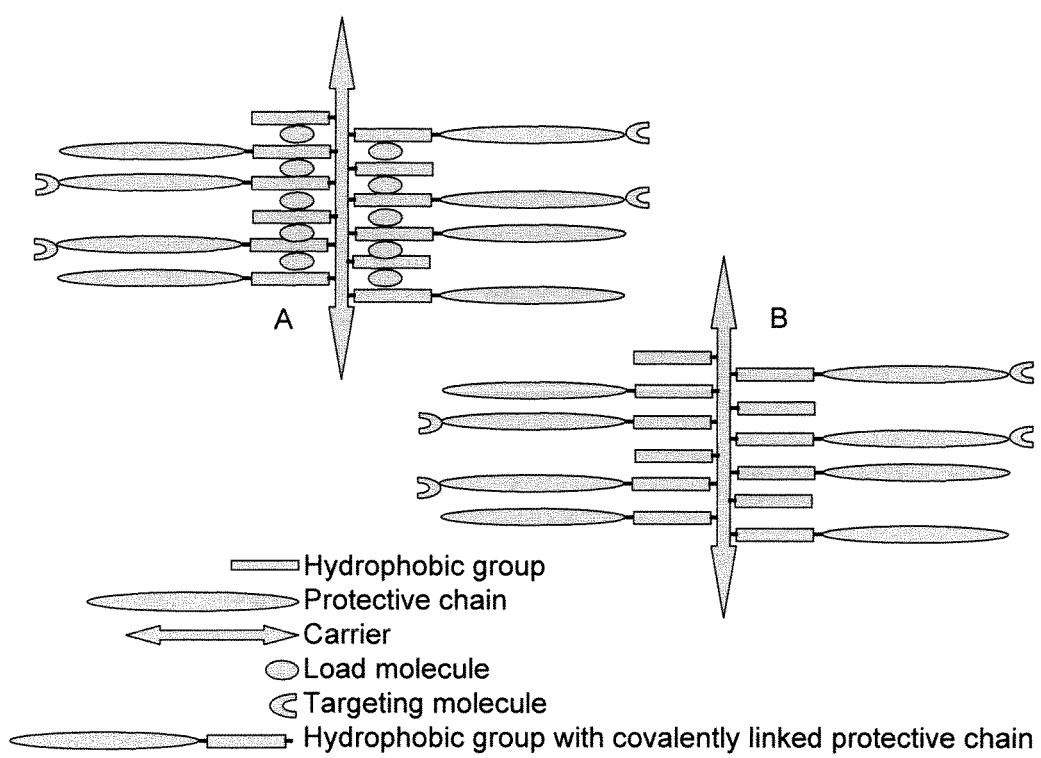
FIG. 23 depicts a diagram of two embodiments of the hydrophobic-core composition of the present invention comprising a carrier, a hydrophobic group with a covalently linked protective chain, a targeting molecule, a hydrophobic group without covalently linked protective chain, with (A) and without (B) load molecule.
Figure 24:
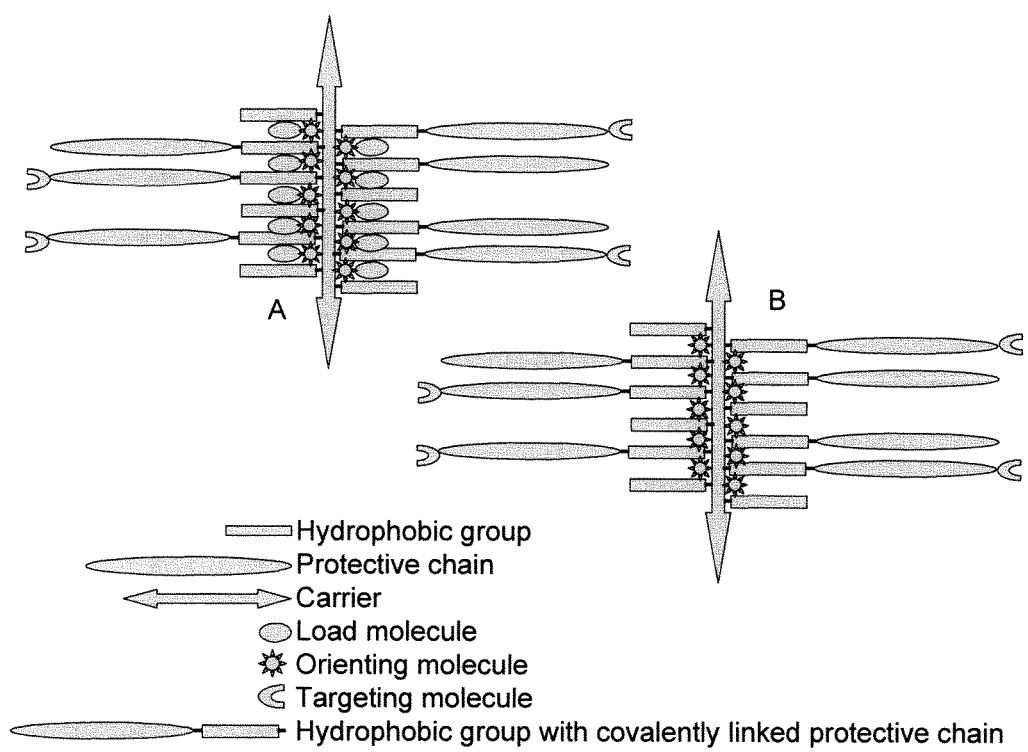
FIG. 24 depicts a diagram of two embodiments of the hydrophobic-core composition of the present invention comprising a carrier, a hydrophobic group with a covalently linked protective chain, a targeting molecule, a hydrophobic group without covalently linked protective chain, an orienting molecule, with (A) and without (B) load molecule.
Figure 25:
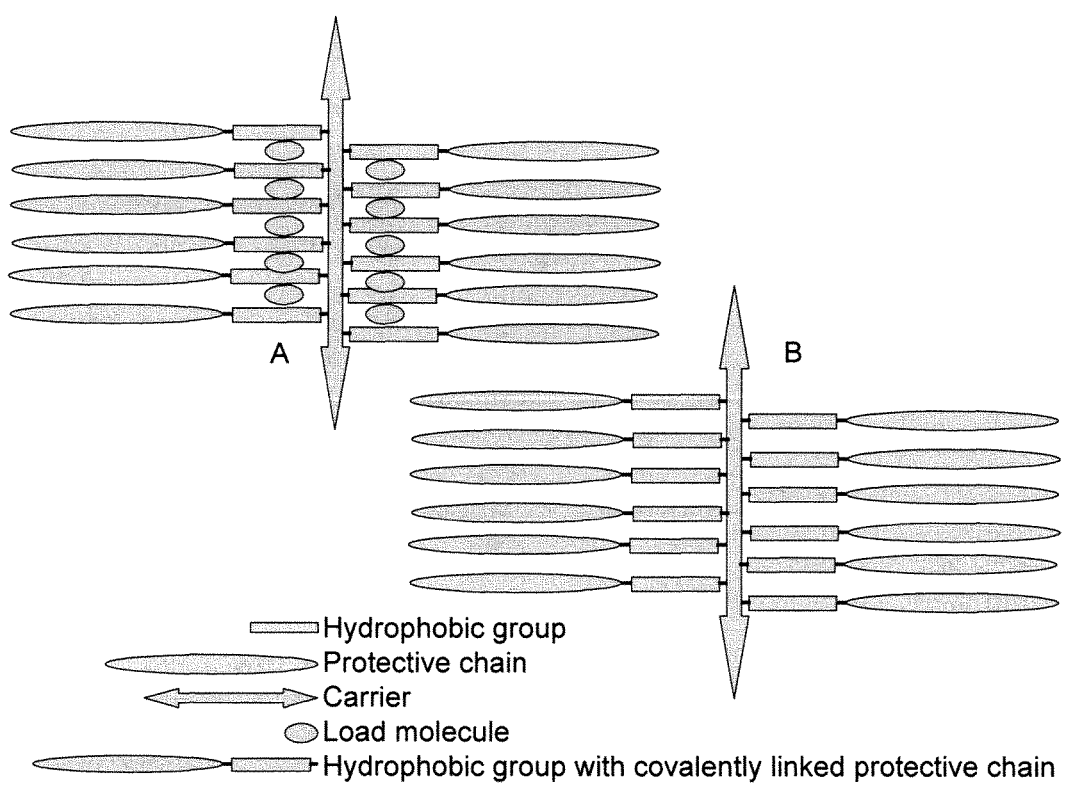
FIG. 25 depicts a diagram of two embodiments of the hydrophobic-core composition of the present invention comprising a carrier, a hydrophobic group with a covalently linked protective chain, with (A) and without (B) load molecule.
Figure 26:
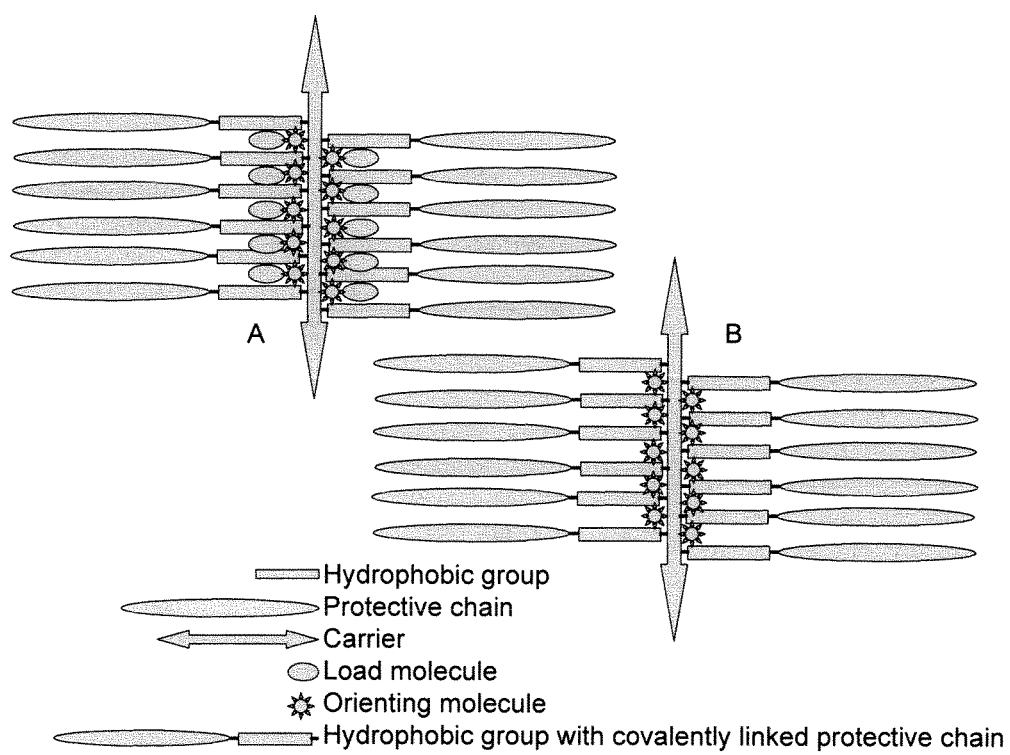
FIG. 26 depicts a diagram of two embodiments of the hydrophobic-core composition of the present invention comprising a carrier, a hydrophobic group with a covalently linked protective chain, an orienting molecule with (A) and without (B) load molecule.
Figure 27:
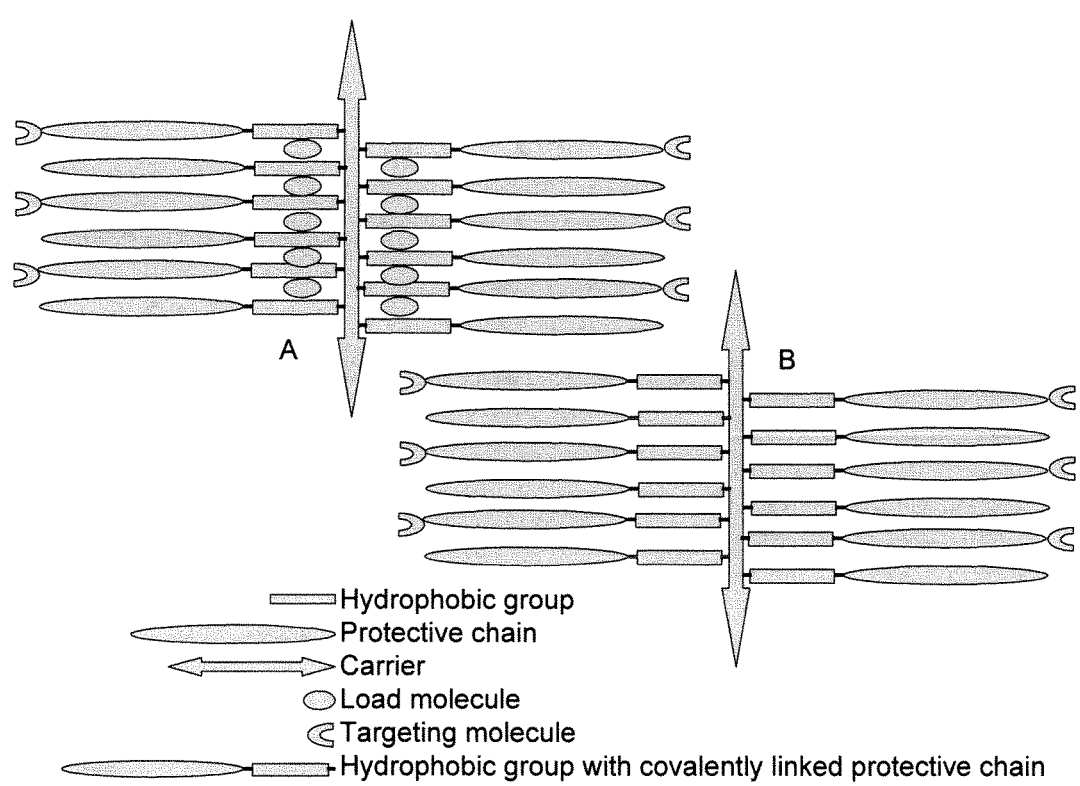
FIG. 27 depicts a diagram of two embodiments of the hydrophobic-core composition of the present invention comprising a carrier, a targeting molecule, a hydrophobic group with a covalently linked protective chain with (A) and without (B) load molecule.
Figure 28:
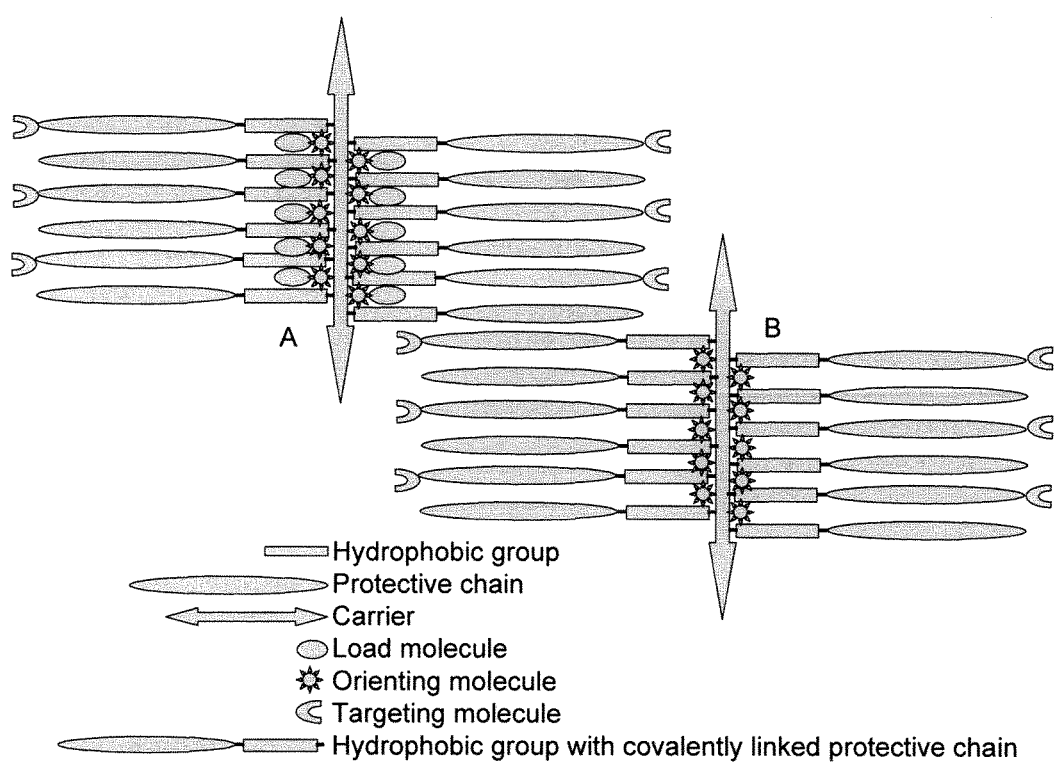
FIG. 28 depicts a diagram of two embodiments of the hydrophobic-core composition of the present invention comprising a carrier, a targeting molecule, a hydrophobic group with a covalently linked protective chain, an orienting molecule with (A) and without (B) load molecule.
Figure 29:
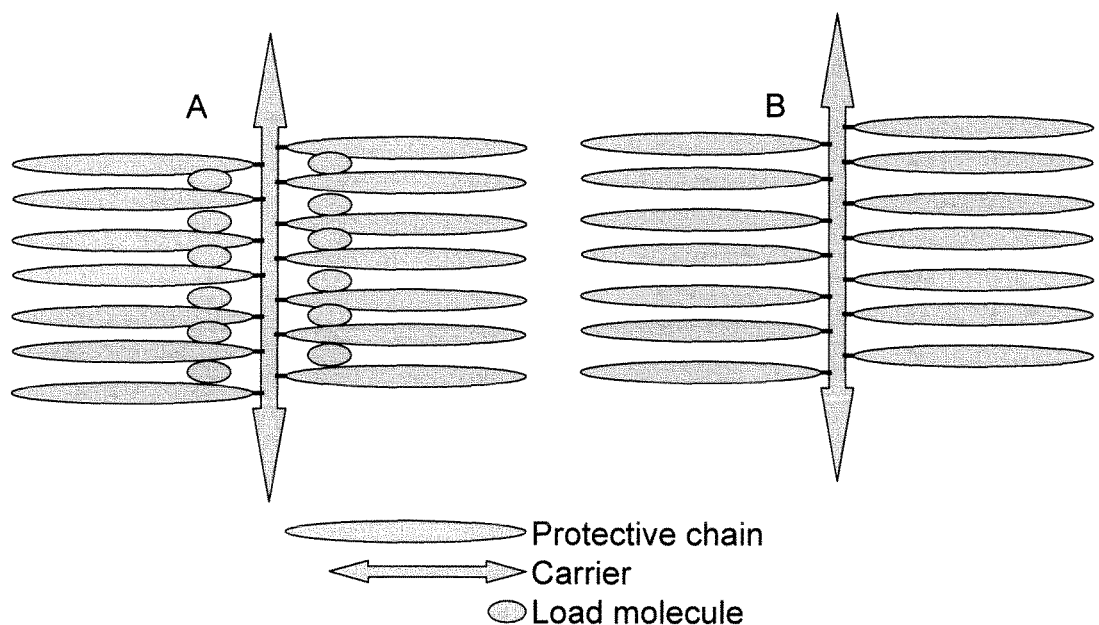
FIG. 29 depicts a diagram of two embodiments of the hydrophobic-core composition of the present invention comprising a carrier, a protective chain wherein the protective chain provides the hydrophobicity and is bonded directly to the carrier, with (A) and without (B) a load molecule.

Six polypropylene microcentrifuge tubes were prepared in triplicate. Aliquots (90 ul) of PLPEG-II-C12 stock (5 mg/ml) from Example 9 were placed in polypropylene microcentrifuge tubes 1 and 2. Aliquots (90 ul) of PLPEG-II stock (5 mg/ml) were placed in polypropylene microcentrifuge tubes 3 and 4. Tubes 3 and 4 contain the PLPEG-II without C12 fatty acid derivatization. However it should be noted that they contain succinate derivatives at the base of the protective group which are equivalent to C4. Sixty ul aliquots of GLP-1 (3 mg/ml; 7-36 amidated Human GLP-1, Polypeptide Lab. GmbH, Germany) were added to tubes 2, 4, and 6. Fifty ul aliquots of 1.5 M NaCl/0.5M $PO_4$ buffer, pH 7.35 were added to all tubes. Contents of all tubes were increased to 0.5 ml with water, giving final buffer and NaCl concentration of 50 mM phosphate/150 mM Nacl/pH 7.35. The solutions were mixed and lyophilized. The next day, all the solutions were made up to 0.5 ml with water and were passed through a 100 kDa cut-off membrane (from Millipore, Bedford, Mass.) by centrifugation. The GLP-1 that went through the filter was the concentration of free GLP-1 in solution. The control tubes without the PLPEG-II-C12 or PLPEG-II (tube 6) will be the total amount of GLP-1 available for binding. The control for tube 6 is tube 5, which is buffer alone. The amount of bound load molecule can be calculated by subtracting the amount of free load molecule from the corresponding control that received the same concentration of load molecule but without the hydrophobic-core carrier. The quantification of load molecules that passed through the filter was done by HPLC (see FIG. 10). The result indicated that PLPEG-II without C12 fatty acid modification is capable of binding GLP-1 equivalent to 20% its weight. However, the PLPEG-II with C12 fatty acid modification showed binding of all the available GLP-1. This indicates that PLPEG-II-C12 can bind GLP-1 equivalent to at least 32% its weight. The amount of free GLP-1 cannot be detected using conventional HPLC-UV detection, indicating that the amount of free GLP-1 is below 10 nM. The exact amount of free GLP-1 under this condition can be ascertained by using Elisa kit for GLP-1 (Linco, St. Charles, Mo.).

Example 11

Figure 31:
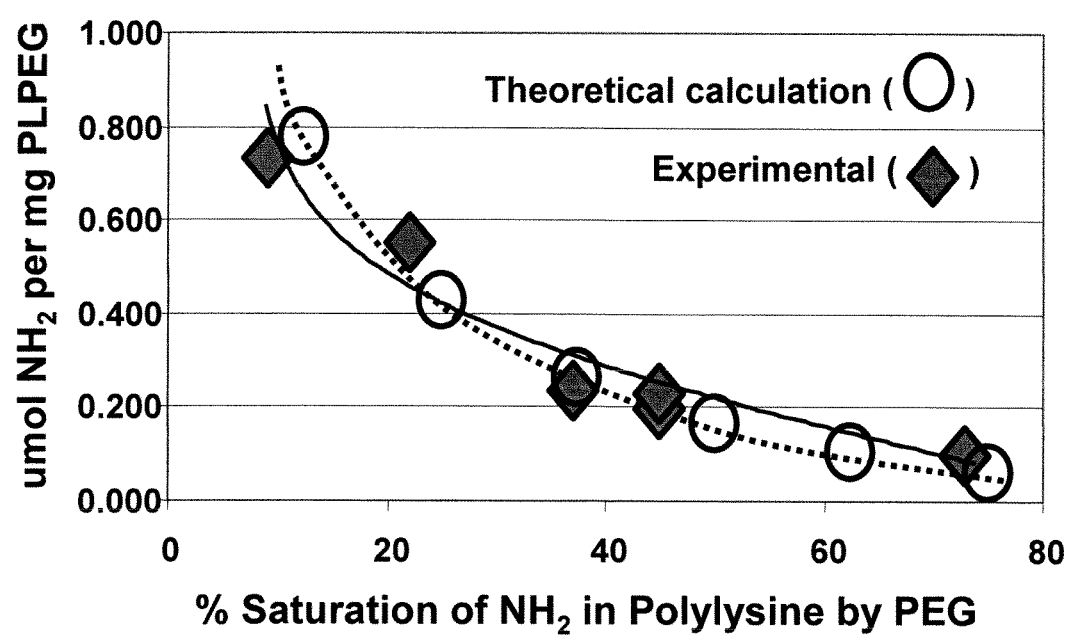
FIG. 31 is a graph showing the theoretical and actual relationship between the amount of amino-group/mg of PLPEG (polylysine-polyethyleneglycol copolymer) and % amino-group saturation of polylysine. This is very useful as secondary confirmation of the composition of PLPEG. This PEGylation process is quite reproducible and adjustable during synthesis by continuing the reaction until the desired % PEGylation is achieved using TNBS amino group assay as a feedback guide during the reaction. The yield is about 50-60% (5-6 gr) of the starting materials. The theoretical prediction was calculated using the following equation: $X=[100\times(C-Y)]/5YC+C]$; where X is the % saturation; Y is the mmol $NH_2$ per gram of PLPEG as determined by TNBS; C is the mmol of $NH_2$ per gram of PL (polylysine) as determined by TNBS. The 5 in the term 5YC in the equation represent the size of PEG used which in this case is 5 kDa, thus 5YC. If 10 kDa PEG is used, this will be 10 YC. This is useful because once PLPEG product is formed, the percent saturation of the amino group of polylysine can be determined by a single TNBS assay of the final product to determine Y from which X can be calculated.
Figure 32:
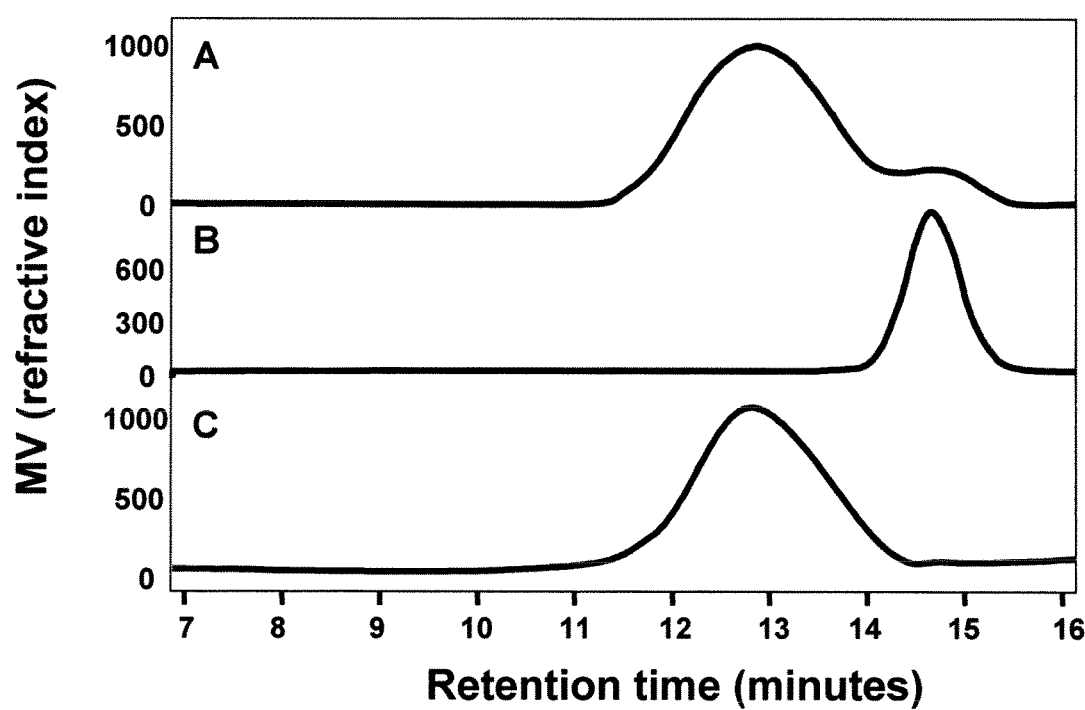
FIG. 32. These are Gel Filtration Chromatograms of the products of the reaction before and after clean up through 100 kDa MWCO membrane (Amersham Biosciences, Needham, Mass.) showing that all unreacted PEG had been removed. The column used was Ultrahydrogel linear (0.78× 30 cm, Waters) eluted at flow rate of 0.6 ml/min PBS. The materials were detected using refractive index detector. Panel A is 20PLPEG5-55 (20 kDa polylysine where 55% of the amino groups were reacted with PEG succinate of 5 kDa molecular weight) prior to clean-up from unreacted 5 kDa PEG. Panel B is 5 kDa PEG alone. Panel C is 20PLPEG5-55 after clean up.
Figure 33:
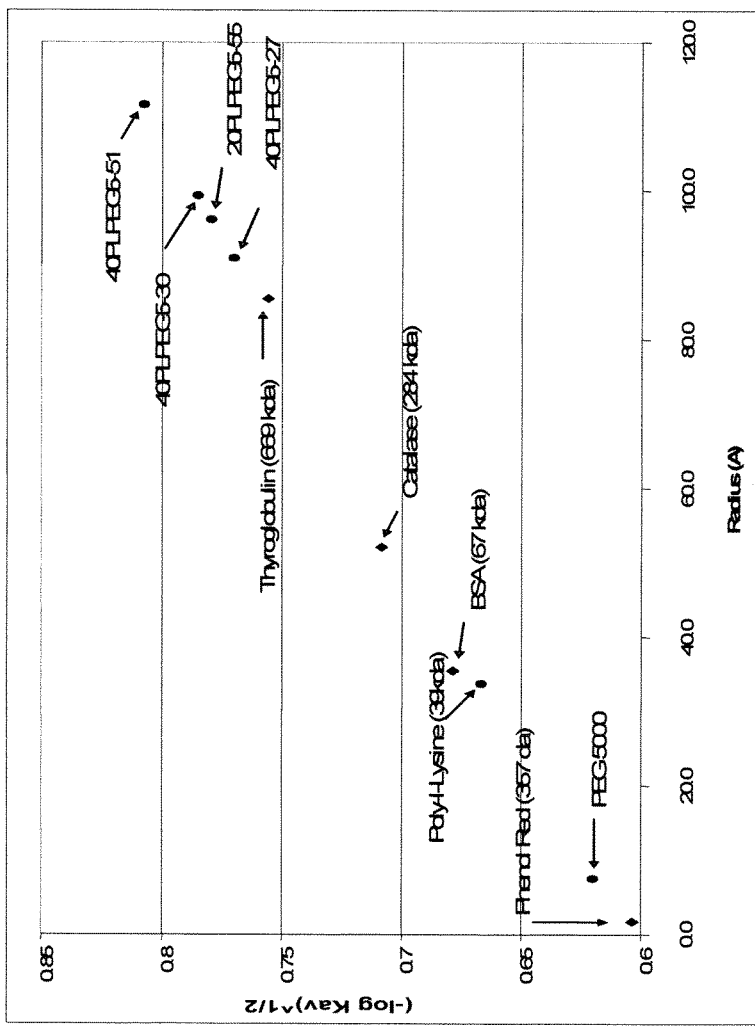
FIG. 33. These are the stokes radii of various carriers along with proteins of known stokes radii. These were analyzed on the Ultrahydrogel Linear column (0.78 cm diameter×30 cm length) using PBS with 15% Acetonitrile at a flow rate of 0.6 ml/min as mobile phase. The 20PL-PEG5-55 (20 kDa polylysine where 55% of the amino groups were reacted with PEG succinate of 5 kDa molecular weight), 40PL-PEG5-30 (40 kDa polylysine where 30% of the amino groups were reacted with PEG succinate of 5 kDa molecular weight), 40PL-PEG5-51 (40 kDa polylysine where 51% of the amino groups were reacted with PEG succinate of 5 kDa molecular weight), and 40PL-PEG5-27 (40 kDa polylysine where 27% of the amino groups were reacted with PEG succinate of 5 kDa molecular weight) are larger than the glomerular filtration cut off that is above 4 nm (40 Angstrom) in diameter (or 20 Angstrom in radius). Proteins with known stokes radii were used as reference including Thyroglobulin (669 kDa; 85.5 Angstroms stokes radius), Catalase (248 kDa; 52.2 Angstrom stokes radius), and BSA (67 kDa; 35.5 Angstrom stokes radius).

Synthesis of 20PLPEG5-55 and Quality Assurance:

To determine the theoretical and actual relationship between the amount of amino-group/mg of PLPEG (polylysine-polyethyleneglycol copolymer) and % amino-group saturation of polylysine, an equation was developed to predict the saturation of polylysine based on the amino group measured by TNBS reaction expressed per mg of the final PLPEG product. This is useful only if the PEG used in the reaction is 95-100% purity from any carboxyl containing compounds. The equation is very useful as secondary confirmation of the composition of PLPEG. The theoretical prediction was calculated using the following equation: $X=[100\times(C-Y)]/5YC+C]$; where X is the % saturation; Y is the mmol $NH_2$ per gram of PLPEG as determined by TNBS; C is the mmol of $NH_2$ per gram of PL (polylysine) as determined by TNBS. The 5 in the term 5YC in the equation represent the size of PEG used which in this case is 5 kDa, thus 5YC. If 10 kDa PEG is used, this will be 10YC. This is useful because once PLPEG product is formed, the percent saturation of the amino group of polylysine can be determined by a single TNBS assay of the final product to determine Y from which X can be calculated. This equation was tested against experimental data by synthesizing PLPEG using high purity MPEG-sucinate as follows. 1 gm of 20 PL (this time 1 gm has 1.7 mmol NH2) was dissolved in 100 ml of 200 mM HEPES. On a separate container 5 g of MPEGSuccinate in 25 ml of 10 mM MES pH=4.7 was activated by adding 250 mg of NHSS, followed by 500 mg EDC dissolved in water. Activation is allowed to proceed for 18-20 minutes. The activated MPEGSuccinate was added to 20 PL solution and allowed to react for 4 hrs. After 4 hrs, additional 5 g of MPEGSuccinate was activated and added as above and allowed to incubate overnight with stirring. The next day, amino group was measured and found to be 0.77 mmol indicating 55% saturation of amino group. A small portion of the sample was analyzed by size exclusion chromatography before (FIG. 32 panel A) and after washing by ultrafiltration through 100 kDa molecular cut-off filter (FIG. 32 panel C) and the diameter of the co-polymer was determined (FIG. 33). The washed sample was lyophilized (8 grams; designated 20PLPEG5-55) and the amount of aminogroup per mg of dried final product was determined by TNBS assay (Sparado et al. Anal Biochem 96:317, 1979). Using the equation above the percent PEG saturation was confirmed to be 55% (FIG. 31). Several more syntheses were performed and the theoretical was compared with experimental (FIG. 31).

Example 12

Synthesis of C18-20PLPEG5-55 (PGC-HC18):

8 gm of 20PLPEG5-55 (1.6 mmol NH2) was dissolved in 143 ml DCM with TEA (200 ul; Mw=101; 2 mmol). Stearic acid or C18 (570 mg; Mw=285; 2 mmol) was activated and stabilized by 230 mg NHS (Mw=115; 2 mmol) in 5.7 ml DMF by adding DCC (Mw=206; 0.47 ml=0.618 g=3.0 mmol) and incubating for 2 hrs (solution becomes insoluble as the insoluble NHS activated FA and Urea forms). The activated C18 was added to 20PLPEG5-55 solution and allowed to react. After 2 hrs the process was repeated and allowed to incubate over the weekend with stirring. Total volume is 160 ml (PLPEG is 50 mg/ml) and 40 ul of the reaction mixture was diluted to 1 ml water and 150 ul aliquots were assayed for amino groups (2 mg/ml; 0.002 umol-NH2/mg). The insoluble urea was filtered out using filter number 1 Whatman filter paper. The filtrate was concentrated by rotary evaporation and washed by ultrafiltration through 100 kDa molecular cut-off filter with 4l of 70% ethanol overnight followed by 1 L water. The sample was filtered sterilized through 0.2 um filter and lyophilized (6.7 g).

Example 13

Synthesis of C24-20PLPEG5-55:

3 gm of 20PLPEG5-55 (0.6 mmol NH2) was dissolved in 60 ml DCM 100 ul TEA was added. Lignoceric acid or C24 (Mw=368.6; 276 mg; 0.75 mmol) was activated and stabilized by NHS (86 mg; Mw=115; 0.75 mmol) in 2.7 ml DMF by adding DCC (Mw=206; 0.17 ml=0.226 g=1.1 mmol) and incubating for 2 hrs (insoluble urea precipitated as the NHS activated FA and Urea forms). The activated C24 was added to 20PLPEG5-55 solution and allowed to react. After 2 hrs the process was repeated and allowed to incubate overnight with stirring. Total volume at the end is 70 ml. Twenty-three ul of the reaction mixture was diluted to 1 ml water and 150 ul aliquots were assayed for amino groups (1 mg/ml) and found to contain 8 uM which is only slightly above 6 uM water blank. The insoluble urea was filtered out using number 1 Whatman filter paper. The filtrate was concentrated by rotary evaporation and washed by ultrafiltration through 100 kDa molecular cut-off filter with 4l of 70% ethanol overnight followed by 1 L water. The sample was filtered sterilized through 0.2 um filter and lyophilized (1.9 g).

Example 14

Loading of C18-PLPEG5-55 (PGC-HC18) with GLP1.

GLP1 (200 ug) was dissolved in 500 ul of 70% acetone/water (v/v) transferred to 10 mg of carrier in drying vial. The carrier containing 200 ug GLP 1 was evaporated in mild vacuum taking precautions not to freeze or violently boil the sample by controlling the amount of vacuum applied. When the solution was dry the vial was sealed for use at later time. The peptide sample in the vial is very stable at 4° C. for months. So far we have not seen degradation of GLP 1 under this condition. This process of loading was developed base on the following results shown in FIG. 34 using PGC-HC24. Once dry, the sample is capped and kept in the freezer or at 4° C. until use. Loaded carriers will normally be reconstituted in PBS for injection. All these are done under sterile condition. Alternatively, the final product can be filtered through 0.5 um filter after reconstitution. The filtered product can then be lyophilized. Solvent other than acetone can be used such as Acetonitrile Methanol or Ethanol. The purpose of these solvents is to partially solubilize the fatty acid and allow peptides to get closer. During drying, as the volatile solvent disappears, the peptide will get closer to the fatty acid and will bind to it. Note that all these solvent has boiling point lower than water. (Acetone bp=57° C.; Acetonitrile bp=80° C.; Methanol bp=65° C.; Ethanol bp=78° C.). The loading ratio will depend on the peptide and the desired blood concentration but normally around 2-20% relative to carrier weight. For GLP1 peptide only 4-5% binds at high affinity sites (nM) and the remaining 6% binds at the low affinity sites (uM). Because we wanted to maintain low GLP1 concentration the blood, we only used the high affinity site and thus we normally load 2% of the carrier weight.

Example 15

Determination of the Dissociation Constant (Kd) Between PGC-HC18 and GLP1.

Figure 37:
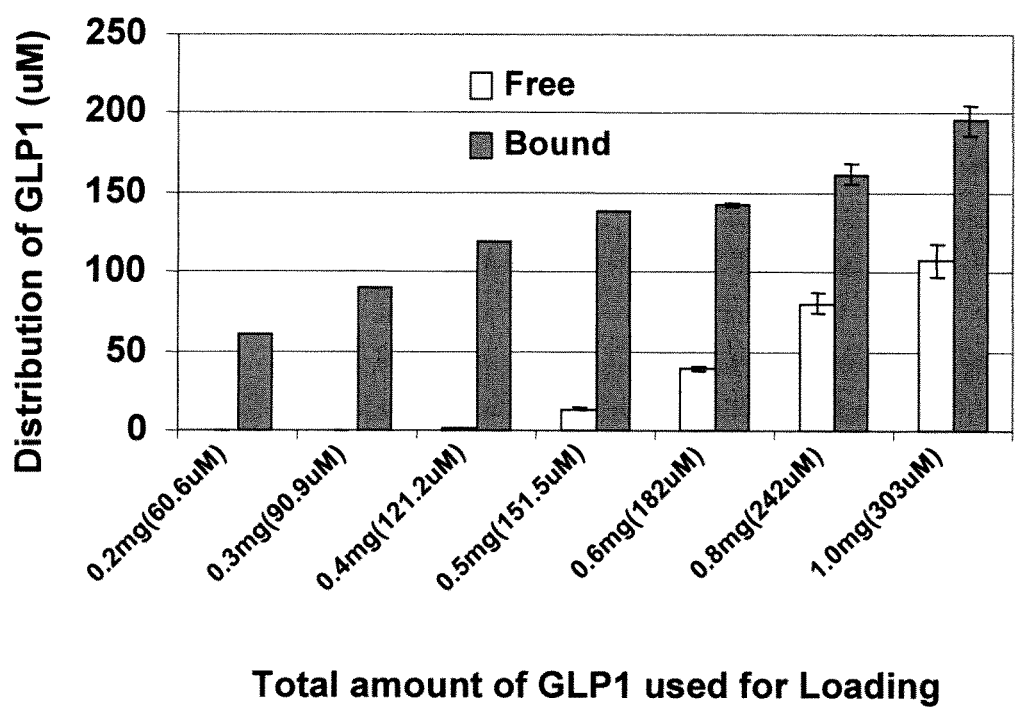
FIG. 37. This figure Shows loading of GLP-1 to C18-PL-PEGS-55 (this hydrophobic core carrier is a 20 kDa polylysine where 55% of the amino groups were reacted with PEG succinate of 5 kDa molecular weight and the remaining aminogroups were reacted with stearic acid or C18). The graph shows the amount bound (gray bar) and free (clear bar) GLP-1 when 10 mg of hydrophobic core carrier was loaded with various amount of GLP-1 (x-axis) using the Acetone Method described in FIG. 34. Each loaded carrier was dissolved in 1 ml PBS and allowed to equilibrate for 2 hours. Each solution containing free and bound GLP1 was filtered through 100 kDa molecular cut-off regenerated cellulose filter (Millipore, Bedford, Mass.). The filtrate containing the free and the bound released by 70% acetonitrile followed by similar filtration were quantified by reverse phase HPLC (n=9). As can be seen the loading capacity is between 4 to 5%, (0.4-0.5 mg/10 mg of Carrier) representing 4-5 sites per carrier. It should be noted that at 1.0 mg loading only ⅔ of the protein gets loaded. The increase in loading above the capacity is likely due to additional low affinity sites with Kd of 3.7 uM and 33 uM. These sites may be due to interaction with PEG or other combination of surfaces within the nanostructure.

PGC-HC18 is a hydrophobic core carrier made up of 20 kDa polylysine where 55% of the amino groups were reacted with PEG succinate of 5 kDa molecular weight and the remaining aminogroups were reacted with stearic acid or C18. Multiple tubes containing 5 mg of carrier/tube were mixed with 0.50, 0.40, 0.30, 0.25, 0.20, 0.15, 0.1 mg of GLP 1 in triplicate. The amount of GLP-1 mixed with carrier in each vial represented 2, 3, 4, 5, 6, 8, and 10% of the carrier weight. Blank tubes containing no carrier were also prepared and similarly treated in subsequent procedures. These samples were lyophilized and 100 ul aliquot of 70% Acetone was added to each vial and the samples were allowed to evaporate to dryness. The samples were reconstituted to 500 ul of PBS (pH 7.3) and the bound GLP1 were filtered out using 100 MWCO regenerated cellulose filter (Millipore, Bedford, Mass.) by centrifugation at 10,000×g for 12 minutes. The filtrates containing free GLP-1 were quantified by reverse phase HPLC. The materials left in the filter were washed 3 times with 100 ul of 70% acetonitrile by centrifugation as above and the liberated GLP 1 (bound portion) from each sample was quantified by reverse phase HPLC. The Bound/Free values were calculated and plotted against bound values (FIG. 35). The relative amounts of bound GLP-1 compared to free are shown in FIG. 37. The slopes of the regression line of the linear regions represented −1/Kd from which Kds were calculated (FIG. 35). It was found that there are three distinct Kds in each carrier. The Kd of 249 nM is the higher affinity site and the estimated number of site with this affinity is 4-5/carrier. The second Kd of 3.7 uM is an intermediate affinity representing 2 sites/carrier. The third Kd of 33 uM is the lowest affinity representing another 2 sites/carrier. The latter two affinities are not very relevant sites for the purpose of GLP-1 delivery since they have affinities that are closer to the Km (300 uM) of the DPP4 enzyme (GLP-1 degrading enzyme) to GLP-1.

Example 16

Determination of the Dissociation Constant (Kd) Between PGC-HC24 and GLP1.

PGC-HC24 is a hydrophobic core carrier made up of 20 kDa polylysine where 55% of the amino groups were reacted with PEG succinate of 5 kDa molecular weight and the remaining aminogroups were reacted with lignoceric acid or C24. Multiple tubes containing 5 mg of carrier/tube were mixed with 0.50, 0.40, 0.30, 0.25, 0.20, 0.15, 0.1 mg of GLP1 in triplicate. The amount of GLP-1 mixed with carrier represented 2, 3, 4, 5, 6, 8, and 10% of the carrier weight. Blank tubes containing no carrier were also prepared and similarly treated in subsequent procedures. These samples were lyophilized and 100 ul aliquot of 70% acetone was added to each tube and was allowed to evaporate to dryness. The samples were reconstituted to 500 ul of PBS (pH 7.3) and the bound GLP1 were filtered out using 100 MWCO regenerated cellulose filter (Millipore, Bedford, Mass.) by centrifugation at 10,000×g for 12 minutes. The filtrates containing free GLP-1 were quantified by reverse phase HPLC. The materials left in the filter were washed 3 times with 100 ul of 70% acetonitrile by centrifugation as above and the liberated GLP1 (bound portion) from each sample was quantified by reverse phase HPLC. The Bound/Free values were calculated and plotted against bound values (FIG. 36). The slopes of the regression line of the linear regions represented −1/Kd from which Kds were calculated. It was found that there are three distinct Kds in each carrier. The Kd of 77 nM is the higher affinity site and the estimated number of these site is 3-4. The second Kd of 2 uM is an intermediate affinity representing 2 sites. The latter affinity is not a very relevant site since it is closer to the Km (300 uM) of the DPP4 enzyme (GLP-1 degrading enzyme) to GLP-1.

Example 17

Testing of the Solution Stability of GLP1-Hydrophobic-Core Carrier (PGC-HC18) Complex.

Figure 38:
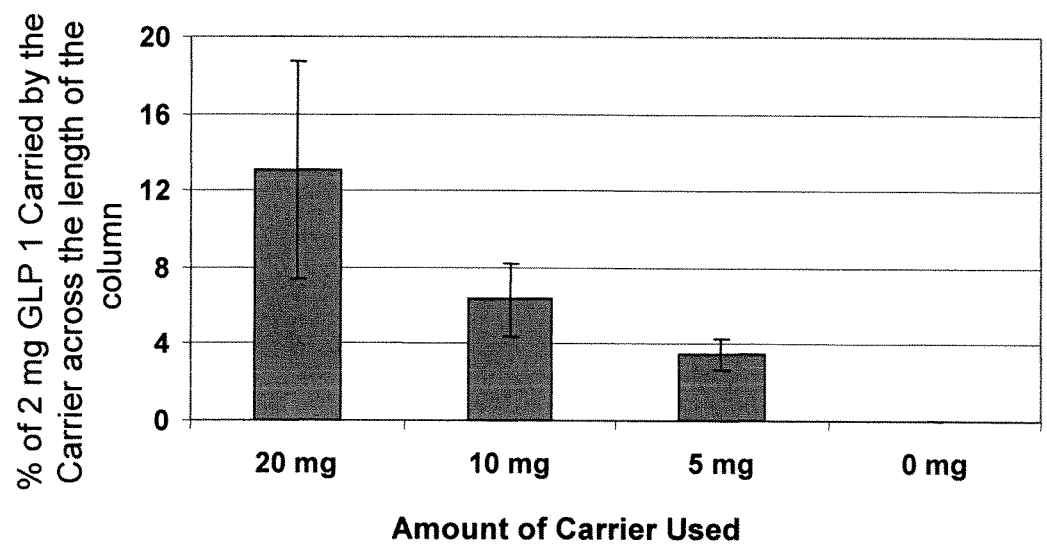
FIG. 38. The graph shows the amounts of GLP-1 that remained associated with the carrier after the carrier has gone through thousand equilibrations in PBS. Solution stability of GLP1-Hydrophobic Carrier (C18-20PLPEG555) complex was tested by monitoring the amount of GLP-1-Bound Carrier after the complex traverses a size exclusion column (0.78×30 cm). A total of 2 mg GLP-1 was loaded to various amounts of C18-carrier using acetone method outlined in FIG. 34. The solution containing both complexed (bound) and free GLP-1 was eluted through size exclusion chromatography (n=5) and monitored at 220 nm. Free GLP-1 comes out at total volume (Vt) while the carrier comes out at void volume (Vo). The carrier alone was used as a blank to quantify the area of GLP-1 associated with the carrier that comes out at Vo of BioSeptember 2000 column (0.78×30 cm; Phenomenex). It should be noted that the high standard deviation is due to high blank rather than the loading variability. This essentially shows that the complex is stable and the Kd of 249 nM is confirmed by this stability test.

PGC-HC18 is a hydrophobic core carrier made up of 20 kDa polylysine where 55% of the amino groups were reacted with PEG succinate of 5 kDa molecular weight and the remaining aminogroups were reacted with stearic acid or C18. Gel permeation chromatography elutes molecules based on size. The size of the PGC-HC18 is about 300 kDa while the size of GLP-1 is 3 kDa. When the PGC-HC18 is eluted alone in though a gel permeation column (Bio-September 2000 column; 0.78×30 cm; Phenomenex) it comes out close to the void volume (Vo), whereas GLP1 alone comes out at much later time closer to the total volume of the column or Vt. When the non-covalent complex between PGC-HC18 and GLP-1 are eluted though a gel permeation column, the complex will experience equilibration at each theoretical plate of this column and the strength of the interaction will be reflected by how much of GLP-1 remains associated with PGC-HC18 after thousands of equilibrations in PBS (pH 7.4). This was used as a secondary confirmation of the stability of the complex in addition to Kd. The solution stability of GLP-1-Hydrophobic-core-carrier (C18-20PLPEG555) complex was tested by monitoring the amount of GLP-1 bound to the carrier after the complex traverses a size exclusion column (0.78×30 cm). A total of 2 mg GLP-1 each was loaded to various amounts of C18-carrier using acetone method outlined in FIG. 34. The solution containing both complexed (bound) and free GLP-1 was eluted through size exclusion chromatography (n=5) and monitored at 220 nm. Free GLP-1 comes out at total volume (Vt) while the carrier comes out at void volume (Vo). The carrier alone was used as a blank to quantify the area of GLP-1 associated with the carrier that comes out at Vo of BioSeptember 2000 column (0.78×30 cm; Phenomenex). The complex is stable and the Kd of 249 nM is consistent with the result of this stability test (FIG. 38).

Example 18

Protection of GLP-1 by PGC-HC18 from Rapid Degradation by DPP4.

Figure 39:
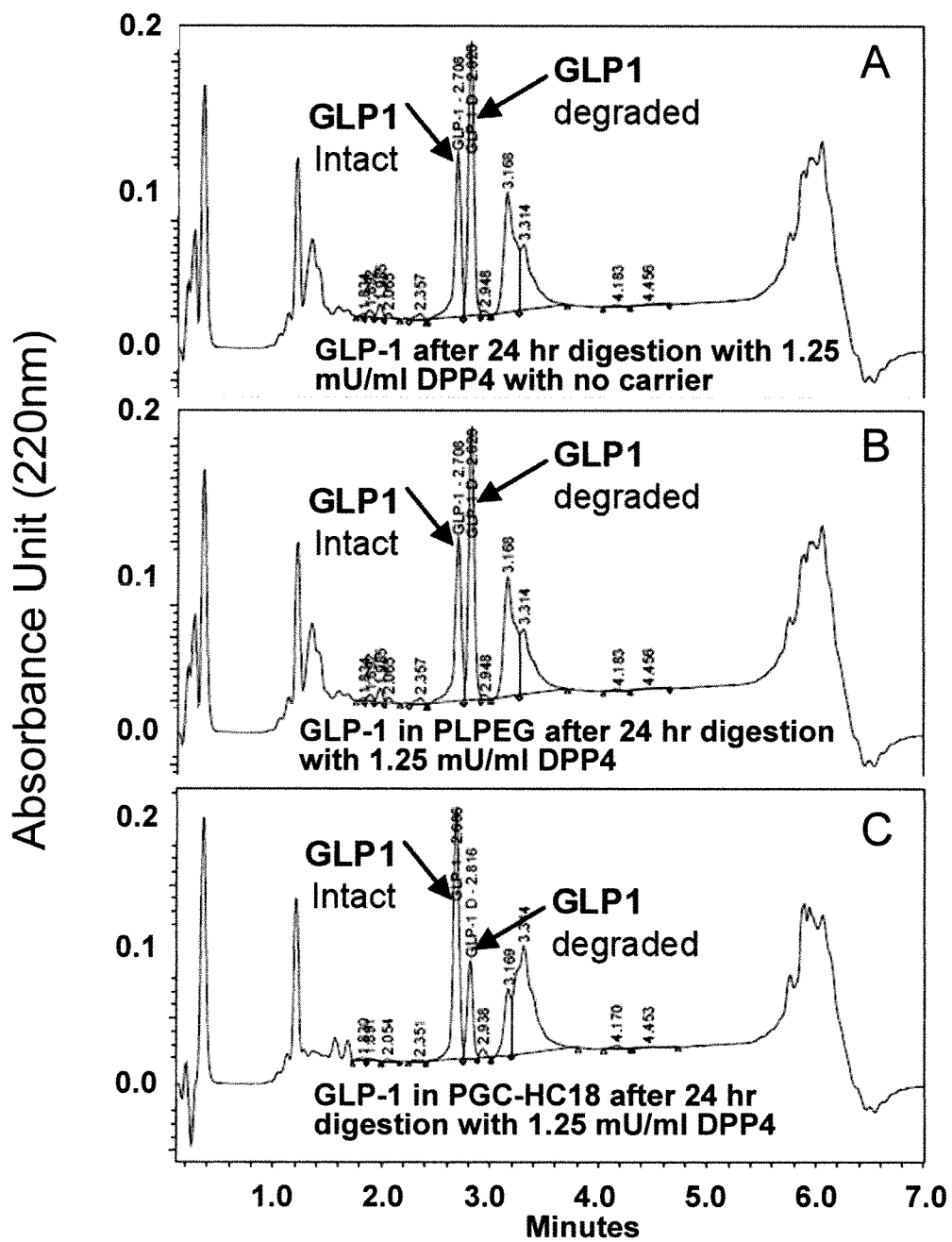
FIG. 39. Shown are sample chromatograms of in vitro digestion of GLP1 by DPP4 in Phosphate Buffered Saline in the presence and absence of PGC-HC18 carrier (this hydrophobic core carrier is a 20 kDa polylysine where 55% of the amino groups were reacted with PEG succinate of 5 kDa molecular weight and the remaining aminogroups were reacted with stearic acid or C18) or 20PLPEG5-55 (this is a carrier is a 20 kDa polylysine where 55% of the amino groups were reacted with PEG succinate of 5 kDa molecular weight and the remaining aminogroups were unreacted). Intact GLP 1 is the early eluting peak (right pointing arrows). The degradation product of GLP 1 (Histidine residue is removed and is less charged, at pH 2 chromatographic condition) elutes at a later time (left pointing arrows). In the presence of PGC-HC 18 carrier, the degradation of GLP 1 by DPP4 is significantly retarded. Both the controls (GLP1 alone and GLP1 with 20PLPEG5-55 are degraded to similar extent. This analysis was performed many times and the results are very conclusive. The HPLC analysis uses Mercury SynergyMax-RP from Phenomenex (0.4×2 cm) eluted at a flow rate of 1.5 ml/min with a gradient of 25-50% Acetonitrile/water/0.1% TFA over 5 minutes and the eluent was monitored at 220 nm. The GLP1 solutions, with and without carrier, were incubated for 24 hours with 1.25 mU/ml DPP4 and the digestion was terminated by addition of DPP4 inhibitor prior to HPLC analysis.

PGC-HC18 is a 20 kDa polylysine where 55% of the amino groups were reacted with MPEG succinate of 5 kDa molecular weight and the remaining aminogroups were reacted with stearic acid or C18. To determine whether the PGC-HC18 will protect GLP-1 from rapid degradation with DPP-4, GLP-1 (1 mg/ml) aliquots in Phosphate Buffered Saline (PBS; pH 7.4) were digested with DPP4 (1.25 mU/ml; Sigma Chem. Co. St Louis, Mo.) in the presence or absence of PGC-HC18 (10 mg/ml) or a control carrier without C18 fatty acid or PGC. The PGC is a 20 kDa polylysine where 55% of the amino groups were reacted with PEG succinate of 5 kDa molecular weight and the remaining aminogroups were unreacted. After 24 hrs of incubation, the digestion was terminated by addition of DPP4 inhibitor prior to HPLC analysis of 10 ul aliquot of each solution (FIG. 39). The HPLC (Waters Co. Milford, Mass.) analysis uses Mercury SynergyMax-RP from Phenomenex (0.4×2 cm) eluted at a flow rate of 1.5 ml/min with a gradient from 25% Acetonitrile/water/0.1% TFA to 50% Acetonitrile/water/0.1% TFA over 5 minutes and the eluent was monitored at 220 nm. Chromatograms of in vitro digestion of GLP 1 by DPP4 in PBS show the intact GLP 1 as the early eluting peak (right pointing arrows, FIG. 39). The degradation product of GLP1 (Histidine residue is removed and is less charged, at pH 2 chromatographic condition) elutes at a later time (left pointing arrows). The other peaks are DPP4 peaks (and protease inhibitors (3-4 min peaks). In the presence of PGC-HC18 carrier, the degradation of GLP 1 by DPP4 is significantly retarded while the GLP 1 alone and GLP 1 with PGC (carrier without fatty acid) are degraded to similar extent. This analysis was performed many times and the results are very conclusive.

Example 19

GLP-1-PGC-HC18 Complex has Enough Free GLP-1 to Bind to Cellular Receptor and Stimulate Ca-Influx.

Figure 40:
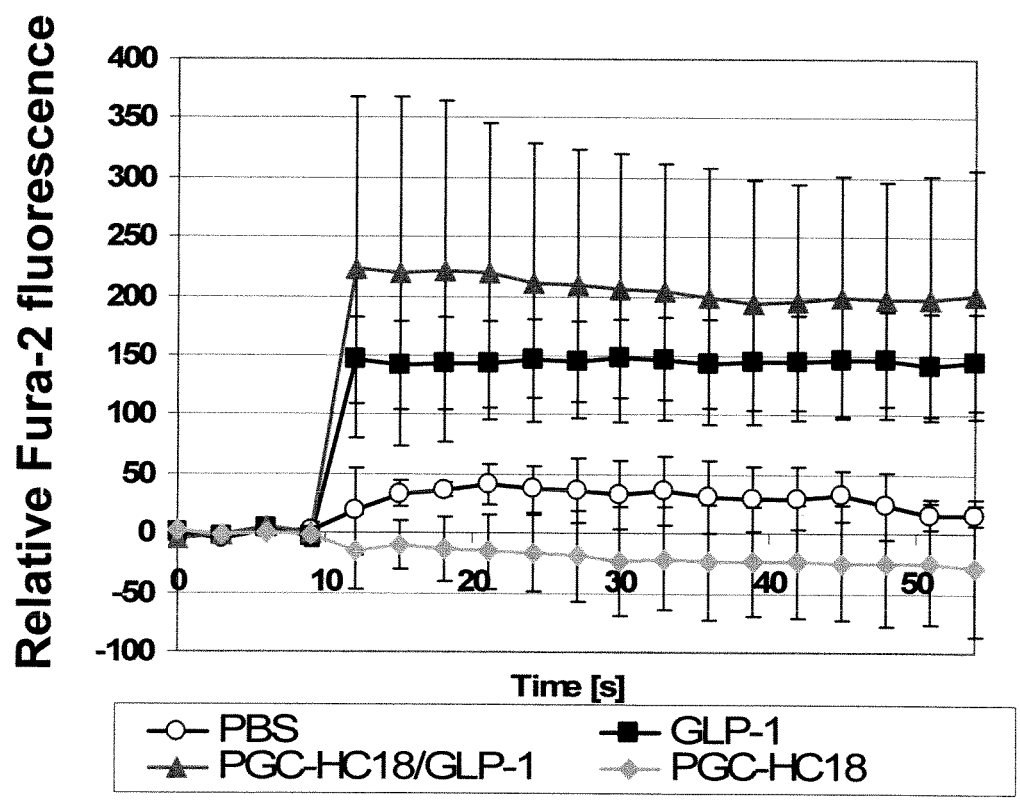
FIG. 40. Calcium Influx induced by GLP1 and by GLP1 contained in the hydrophobic core carrier (PGC-HC18; this hydrophobic core carrier is a 20 kDa polylysine where 55% of the amino groups were reacted with PEG succinate of 5 kDa molecular weight and the remaining aminogroups were reacted with stearic acid or C18). Shown is the Calcium influx induced by GLP1 (20 nM) and GLP1 formulation (3.3 ug/ml PGC-HC18; with 20 nM GLP1) in INS cells. Cells were loaded with Fura-2 (Molecular probes) and the intracellular fluorescence were determined over time before (1-9 sec) and after (11-60 sec) addition of PBS (phosphate buffered saline), GLP-1, C18 formulation (3.3 ug/ml PGC-HC18; with 20 nM GLP1), and C18 carrier (3.3 ug/ml PGC-HC18). As can be seen, the PGC-HC18 formulated GLP1 (C18-formulation) is biologically active in this in vitro test (n=5).

By interacting with the GLP-1 receptor on pancreatic islet cells, GLP-1 leads to a cascade of signaling reactions, including an increase of the intracellular $Ca^{2+}$-concentration, resulting in an increased exocytosis of insulin-containing granules in a strictly glucose-dependent manner (at glucose concentrations >4.5 mM). Since the affinity of GLP-1 for the carrier (Kd 249 nM) is less than that of GLP-1 for its receptor (Kd 1 nM), we anticipated that, in the presence of the receptor, the equilibrium would be shifted in favor of free GLP-1 being released. We tested the ability of formulated GLP-1 to activate GLP-1 receptors on cultured islet cells by evaluating the ability to stimulate calcium influx. Rat insulinoma cells (INS-1 cells) were plated in 96 well plates at 200,000 cells per well and allowed to attached overnight at 37° C./5% $CO_2$/100% relative humidity in 200 ul medium containing RPMI, 10% Fetal Bovine Serum (FBS), 11.1 mM glucose, 10 mM HEPES (pH 7.4), 1 mM sodium pyruvate, and 50 uM 2-mercaptoethanol. The next day, medium was replaced with 20 ul of Phosphate Buffered Saline (PBS) with 2% FBS, 11.1 mM glucose and 0.5 ug/ml Fura 2 (Molecular Probes, Eugine, Oreg.). After 30 minutes, 180 ul PBS with 2% FBS and 11.1 mM glucose and the wells were monitored for background fluorescence (Excitation 340 nm; Emision 510 nm) using Chemeleon (BioScan, Washington D.C.). After 10 seconds, 20 ul of PBS with and without 300 nM GLP 1, 300 nM GLP1 with 150 nM PGC-HC18, or 150 nM PGC-HC18, were each injected into wells (n=5) and the fluorescence of each well was monitored for 60 seconds (Excitation 340 nm; Emision 510 nm). As shown in FIG. 40, PGC-HC18 formulated GLP-1 stimulated calcium influx in INS-1 islet cells confirming its ability to release sufficient GLP-1 to bind and activate the GLP-1 receptor.

Example 20

GLP-1-PGC-HC18 Complex has Enough Free GLP-1 to Bind to Cellular Receptor and Enhance Glucose Stimulated Insulin Secretion.

Figure 41:
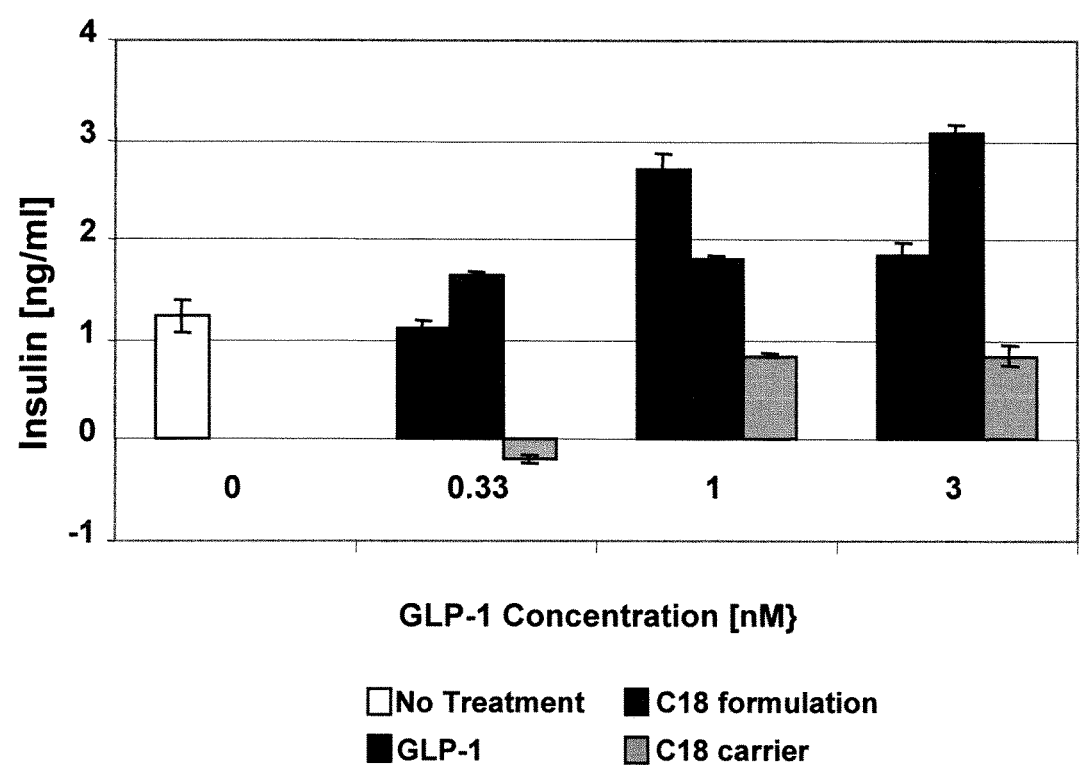
FIG. 41. Formulated GLP1 causes enhancement of glucose stimulated insulin release. Shown is the level of glucose stimulated insulin released by INS cells in the presence of various concentrations of GLP 1 and formulated GLP 1 (PGC-HC18 containing 2% by weight of GLP 1). The PGC-HC18 used in the formulation is a 20 kDa polylysine where 55% of the amino groups were reacted with PEG succinate of 5 kDa molecular weight and the remaining aminogroups were reacted with stearic acid or C18. Insulinoma cells or INS cells (50,000) were plated in 96 well plate and allowed to attached overnight in regular medium (with 11.1 mM glucose), the glucose in the medium was lowered to 5.5 mM overnight. The next day, insulin release was induced by serum free medium containing 11.1 mM glucose and various concentrations of formulated and unformulated GLP 1 (x-axis). Insulin released over 15 minutes was measured using LINCO Elisa kit (n=3).

To further confirm the activity of the formulated GLP 1, the effect of GLP 1 and formulated GLP-1 on the enhancement of glucose stimulated of insulin release that occurs as a result of GLP receptor activation was tested. Rat insulinoma cells (INS-1 cells) were plated in 96 well plates at 50,000 cells per well and allowed to attached overnight at 37° C./5% $CO_2$/100% relative humidity in 100 ul medium containing RPMI, 10% Fetal Bovine Serum (FBS), 11.1 mM glucose, 10 mM HEPES (pH 7.4), 1 mM sodium pyruvate, and 50 uM 2-mercaptoethanol. The next day, additional 100 ul medium without glucose was added, resulting in total glucose concentration of 5.5 mM. The cells were further incubated overnight. The glucose stimulated insulin release was induced by replacing the medium with 200 ul of serum free medium containing glucose (11.1 mM) and different amounts of GLP 1 (0, 0.33, 1 and 3 nM), PGC-HC18 (0, 0.17, 0.33 and 1 nM), GLP1 (0, 0.33, 1 and 3 nM) in PGC-HC18 (0, 0.17, 0.33 and 1 nM). The PGC-HC18 used is 0.5 molar equivalent of GLP-1 used. After 30 minute, the supernatant was collected and the amount of insulin released by the cells was determined by ELISA assay kit from Linco (Linco Research, St Charles, Mo.). The results show that GLP-1 formulation enhances insulin secretion in INS cells similar to free GLP-1 confirming the activity of the formulation (FIG. 41). The GLP-1 formulation also enhances synthesis of insulin similar to free GLP-1 as detected in extracts of INS-1 cells stimulated with GLP-1 and GLP-1 formulation.

Example 21

PGC-HC Prolongs the Biological Half-Life of GLP-1.

Figure 43:
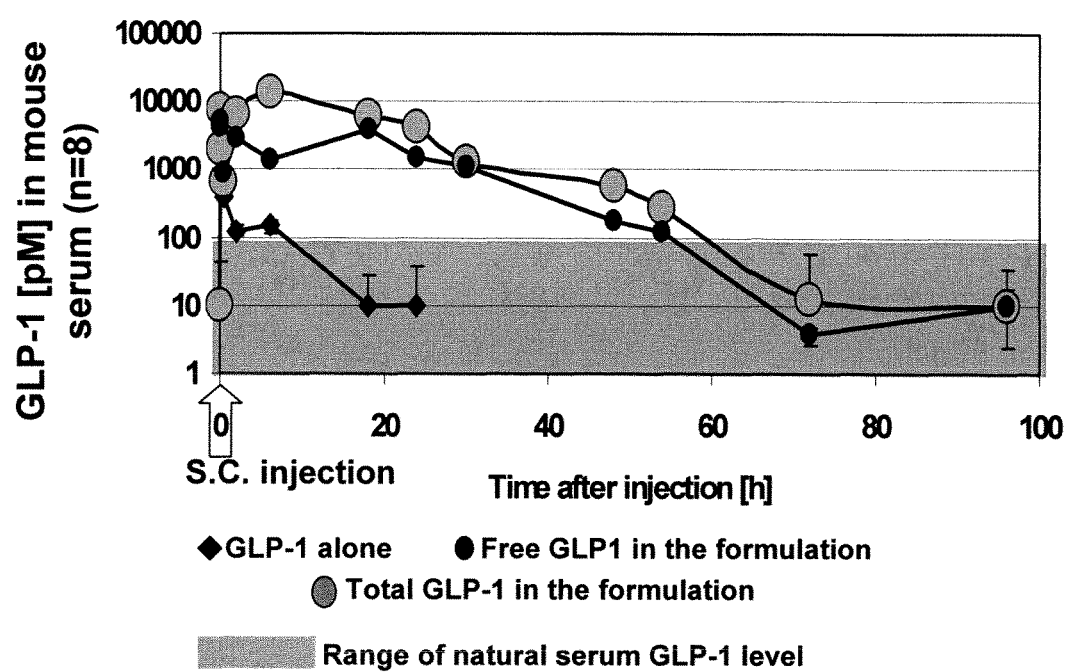
FIG. 43. Time dependent decrease in Total GLP1 in the blood after subcutaneous (s.c.) administration of GLP1 and formulated GLP1 (PGC-HC18 containing 2% by weight of GLP1). The PGC-HC18 used in the formulation is a 20 kDa polylysine where 55% of the amino groups were reacted with PEG succinate of 5 kDa molecular weight and the remaining aminogroups were reacted with stearic acid or C18. The elimination half-life of GLP 1 administered alone is just a few minutes while the formulated GLP1 has half-life of at least 24 hours. Female Balb/c mice were injected s.c.

For this in vivo protocol female Balb/c mice (retired breeders, Charles River) weighing about 25 g were used. Before use the animals were fasted (16 h) in order to avoid lipemia which will interfere with GLP-1 analysis. Seven mice were sacrificed per group at the time of blood collection by decapitation under isoflurane anesthesia. At the t=−1 time point when no drug has been administered seven mice were sacrificed to determine the base line for the groups. At t=0 mice were injected with 50 pmol GLP-1 unformulated or 50 pmol GLP-1 in 25 pmol in PGC-HC18 formulation in 100 ul saline. The injections were given as a bolus by lateral tail vein injection. Identical experiment was also done by administering the drug subcutaneously dorsally near the tail base. This was essential to determine the changes in pharmacokinetics of GLP-1 formulations using two different routes of administrations. This allowed us to confirm that the skin tissue administration further prolongs the half-life formulated GLP-1 in the blood. Seven mice per group were sacrificed at various times after administration by decapitation and the blood samples were collected in microcentrifuge tube containing DPP4 inhibitor used according to manufacturers instructions (Linco Research, St Charles, Mo.). The total GLP-1 in the serum was measured using GLP-1 ELISA assay kit from Linco (Linco Research, St Charles, Mo.). To determine the amount of free GLP-1 in the blood as compared to carrier-bound GLP-1, diluted sera were filtered through the 100 kDa molecular weight cut-off regenerated cellulose filters (Millipore, Bedford, Mass.) and 43 show that the PGC-HC18 prolongs the half-life of GLP-1 in vivo and that subcutaneous administration further enhances the half-life of GLP-1. In addition, subcutaneous administration allows the release of the PGC-HC carrier from the skin as shown in FIG. 43, where the free GLP1 is much less than the total GLP-1 in the serum (note that the y-axis is in a log scale). Similar experiment was done in rats. Briefly, for this in vivo protocol male Sprague Dawley (HSD) rats weighing 350-370 g with pre-implanted jugular cannulation were used. Before use the animals were fasted (16 h) in order to avoid lipemia which will interfere with GLP-1 analysis. Blood samples (250 ul) were drawn at t=−1 min before GLP-1 (50 nmol) or PGC:GLP-1 formulation administration. At t=0 min, 1 ml of phosphate buffered saline containing GLP-1 (50 nmol) or GLP-1 (50 nmol) in PGC-HC18 (25 nmol) was given as a bolus by lateral tail vein injection. Blood samples were drawn at various time points from the cannulated jugular vein. At the end of 96 hrs the animals will be sacrificed by giving IP injection overdose of pentobarbital (200 mg/kg). The result of this experiment confirmed that the GLP-1 formulated with PGC-HC18 has longer biological half-life that the unformulated GLP-1 (FIG. 44).

Example 22

The Use of GLP-1 Formulated in PGC-HC18 for the Treatment of Diabetes.

Briefly for this in vivo protocol, 12-week old male Sprague-Dawley (HSD) rats (Harlan, Indianapolis, Ind.) were housed at 23±1° C. in a 12:12-h light:dark cycle, and were given access to food and water ad libitium (diet LM-485, Teklad, Madison, Wis.). All rats were weighed prior to the start of the experiment and found to be all within 240-260 grams. Diabetes was induced in 20 of these rats by lateral tail vein injection of streptozotocin (STZ; 100 mg/kg) in 200 ul 50 mM Na-Citrate buffer at pH 4.5. Non-fasting blood sugar levels were monitored daily from day 2 by tail-tip snip blood collection (5 ul) and blood sugar levels were measured using Glucometer (Ascensia Elite, Bayer Co. Mishawaka, Ind.) and test strips (Bayer Co. Mishawaka, Ind.). After 10 days, those animals (19) with 95% destruction of beta cell mass based on the average non-fasting blood glucose levels of 340-380 mg/dl were selected for the study. These animals were divided in four groups: STZ treated (n=4), STZ-treated followed by treatment with PGC-HC18 alone without GLP-1 (n=5), STZ treated followed by GLP-1 treatment (n=5), and STZ-treated followed by treatment with GLP-1 in PGC-HC18 formulation (n=5). Subsequent treatments after diabetic induction were administered subcutaneously every 2 days (Monday, Wednesday, Friday) for 4 weeks. The treatment doses included phosphate buffered saline, GLP-1 (20 ug), GLP-1 (20 ug) in PGC-HC18 (1 mg), PGC-HC18 (1 mg). The GLP-1, PGC-HC18, and GLP-1 in PGC-HC18 formulations were reconstituted in 1 ml phosphate saline and administered every 2 days (Monday, Wednesday, Friday) for 4 weeks by subcutaneous injection into the skin of the dorsal shoulder followed by tail blood collection for glucose measurement. At the end of the last injection or treatment and blood collection, the rats were weighed to determine the severity of diabetes (total weight lost from the start of the experiment) since they all started at about the same weight. The rats were then fasted for 16 hr for i.p. glucose tolerance test the next day. Fasting was necessary for glucose tolerance test. Rats were put under anesthesia and then given 2 ml i.p. injection of glucose (1.0 mg/g body weight) and 5'-Bromo-2'-deoxyuridine (BrdU) (50 mg/kg body weight) as islet cell neogenesis marker. Blood (250 ul) will be collected from tail vein at time −2, 0, 2, 5, 10, 20, 30, and 60 minutes after glucose/BrdU injection for insulin and glucose measurement. At the end of 60 minutes the animals were sacrificed by exsanguinations under Isoflurane anesthesia by severing the inferior vena cava before harvesting the pancreas for immunohistochemistry. The pancreata were harvested for immunohistochemical analysis of BrdU incorporation, apoptosis, insulin, and beta cell mass determination. The rats treated with PGC- HC18 formulated GLP-1 have lower average cumulative glucose level than the control groups, indicating that the GLP-1 formulated in PGCHC18 has positive impact on alleviating the severity of diabetes in these rats (FIG. 45). In addition the severe weight loss associated with diabetes was prevented by treatment with PGC-HC18 formulated GLP-1 compared to control groups (FIG. 46). The pancreata from these animals were stained for BrDU to determine the number of dividing cells in the islet (FIG. 47).

Example 23

A Non-Peptide Organic Compound Binds to PGC-HC18.

Doxorubicin is a non-peptide organic compound used for the treatment of various human cancers. To demonstrate the universality of the PGC-HC capability, the PGC-HC18 was loaded with doxorubicin and the dissociation constant (Kd) was determined. Initial analysis of Doxorubicin by HPLC indicated that it elutes at much lower organic solvent concentration than GLP-1, and thus expected to have a higher Kd than GLP-1 for PGC-HC18 binding. For this experiment, doxorubicin (Mw=580) was used at 0.006, 0.012, 0.018, 0.024, 0.030, 0.036 mg for binding to 2 mg of C-18 carrier. Fifteen mg of carrier was dissolved in 1.5 ml water and 200 ul aliquots were placed in each tube and dried. One and half mg of doxorubicin was dissolved 0.75 ml of water (2 mg/ml). Aliquots of 0, 3 (0.006 mg or 0.3%), 6 (0.012 mg or 0.6%), 9 (0.018 mg or 0.9%), 12 (0.024 mg or 1.2%), 15 ul (0.030 mg or 1.5%), and 18 ul (0.036 mg or 1.8%), of doxorubicin was added to each aliquot of dried carrier and blank tubes without the carrier. The tubes were made up to 72 ul with 50% tert-butanol followed by evaporative drying. The dried samples were dissolved in 250 ul of PBS (pH 7.3) and after 2 hrs of equilibration, each sample was filtered using 100 MWCO regenerated cellulose filter (Millipore, Bedford, Mass.) by centrifugation at 10,000×g for 12 minutes. The doxorubicin in the filtrate (free or unbound doxorubicin) was quantified by HPLC (Waters2975 with diode array detector, Milford, Mass.). The HPLC analysis uses Mercury SynergyMax-RP from Phenomenex (0.4×2 cm) eluted at a flow rate of 1.5 ml/min with a gradient of 25-50% Acetonitrile in water with 0.1% TFA over 5 minutes and the eluent was monitored at 220 nm. The free doxorubicin was subtracted from the total doxorubicin to obtain the bound (FIG. 48). The regenerated cellulose filter used for filtration does not bind significant amount of doxorubicin to interfere with the analysis. The Bound/Free values were calculated and plotted against bound values (FIG. 49). The slopes of the regression line of the linear regions represented −1/Kd from which Kds were calculated. It was found that doxorubicin interacts with PGC-HC 18 with Kd of 315 uM.

Although the foregoing invention has been described in some detail by way of illustration and example for the purposes of clarity of understanding, one skilled in the art will easily ascertain that certain changes and modifications may be practiced without departing from the spirit and scope of the appended claims.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The embodiments of the invention in which an exclusive property or priviledge is claimed are defined as follows:

1. A composition, consisting of:
(i) a polymeric carrier;
(ii) a plurality of first hydrophobic groups, wherein each first hydrophobic group of the plurality of first hydrophobic groups is covalently linked to the carrier, is capable of binding a load molecule, comprises an alkyl group of 8-36 carbons, and has a molecular weight between 150 to 1000 Daltons independent of the carrier weight;
(iii) a plurality of first protective side chains, wherein each first protective side chain is covalently linked to the carrier and has a molecular weight between about 400 and 20,000 Daltons independent of the carrier weight, and wherein each first protective side chain is polyethylene glycol, polypropylene glycol, a co-polymer of polyethylene glycol and polypropylene glycol, or an alkoxy derivative thereof;
(iv) optionally a plurality of second hydrophobic groups, wherein each second hydrophobic group is covalently linked at a first end to the carrier and is linked at a second end to a second protective side chain having a molecular weight between 400 and 20,000 Daltons independent of the carrier weight,
wherein each second hydrophobic group is capable of binding a load molecule, has a molecular weight of less than 1,000 Daltons independent of the carrier weight, and
wherein each second protective side chain is polyethylene glycol, polypropylene glycol, a co-polymer of polyethylene glycol and polypropylene glycol, or an alkoxy derivative thereof; and
(v) a load molecule dissociably linked to the hydrophobic groups; and
(vi) a pharmaceutically acceptable excipient;
wherein a weight ratio of total protective side chains to total hydrophobic groups is more than 17:1 and the composition is soluble in aqueous buffer.

2. The composition of claim 1, wherein each second hydrophobic group, when present, comprises an alkyl group of 8-36 carbons and has a molecular weight between 150 to 1000 Daltons independent of the carrier and protective side chain weights.

3. The composition of claim 1, wherein the pharmaceutically acceptable excipient is selected from a starch, a sugar, a sugar alcohol, a salt, an amino acid, water, a buffer, a an antioxidant, a preserving agent, a polyol, an antiadhesive, a stabilizer, or a combination thereof.

4. The composition of claim 1, wherein the pharmaceutically acceptable excipient is one or more of an excipient selected from water, a buffer, a preserving agent, and a stabilizer.

5. The composition of claim 1, wherein the pharmaceutically acceptable excipient consists of a buffer, a preserving agent, and a stabilizer.

6. The composition of claim 1, wherein the load molecule is a therapeutic agent selected from the group consisting of glucagon-like-peptide, exenatide, Gastric inhibitory polypeptide (GIP), Epidermal Growth Factor (EGF) receptor ligand, Transforming Growth Factor alpha (TGF-alpha), Betacellulin, Gastrin/Cholecystokinin receptor ligand, interferon, interleukin, tumor necrosis factor, insulin, insulin-like growth factor, growth hormone, nerve growth factor, brain-derived neurotrophic factor, endostatin, angiostatin, thrombospondin, blood clotting factor VII, blood clotting factor VIII, granulocyte-macrophage colony-stimulating factor (GM-CSF), granulocyte colony-stimulating factor (G-CSF), thrombopoietin, calcitonin, parathyroid hormone (PTH), erythropoietin, vasopressin, terlipressin, atrial natriuretic factor, somatostatin, adrenocorticotropin, gonadotropin releasing hormone, oxytocin, leutinizing-hormone-releasing-hormone, follicle stimulating hormone, vasopressin, terlipressin, desmopressin, vasoactive intestinal peptide (VIP), anti-bacterial agents, anti-fungal agents, anti-viral agents, doxorubicin, auristatin, and vitamins.

7. The composition of claim 1, wherein the load molecule is glucagon-like-peptide, Epidermal Growth Factor (EGF) receptor ligand, Transforming Growth Factor alpha (TGF-alpha), Betacellulin, Gastrin/Cholecystokinin receptor ligand, vasopressin, terlipressin, or atrial natriuretic factor.

8. A composition, consisting of:
  (i) a polymeric carrier;
  (ii) a plurality of first hydrophobic groups, wherein each first hydrophobic group of the plurality of first hydrophobic groups is covalently linked to the carrier, is capable of binding a load molecule, comprises an alkyl group of 8-36 carbons, and has a molecular weight between 150 to 1000 Daltons independent of the carrier weight;
  (iii) a plurality of first protective side chains, wherein each first protective side chain is covalently linked to the carrier and has a molecular weight between about 400 and 20,000 Daltons independent of the carrier weight, and wherein each first protective side chain is polyethylene glycol, polypropylene glycol, a co-polymer of polyethylene glycol and polypropylene glycol, or an alkoxy derivative thereof;
  (iv) optionally a plurality of second hydrophobic groups, wherein each second hydrophobic group is covalently linked at a first end to the carrier and is linked at a second end to a second protective side chain having a molecular weight between 400 and 20,000 Daltons independent of the carrier weight,
  wherein each second hydrophobic group is capable of binding a load molecule, has a molecular weight of less than 1,000 Daltons independent of the carrier weight,
  wherein each second protective side chain is polyethylene glycol, polypropylene glycol, a co-polymer of polyethylene glycol and polypropylene glycol, or an alkoxy derivative thereof;
  (v) a load molecule dissociably linked to the hydrophobic groups;
  (vi) an orienting molecule covalently linked to the carrier, wherein the orienting molecule is selected from the group consisting of sulfate, sulfonate, phosphate, phosphonate, bisphosphonate, lysine, and arginine;
  (vii) optionally a targeting molecule covalently linked to the first protective side chains; and
  (viii) a pharmaceutically acceptable excipient;
  wherein a weight ratio of total protective side chains to total hydrophobic groups is more than 17:1 and the composition is soluble in aqueous buffer.

9. The composition of claim 8, wherein each second hydrophobic group, when present, comprises an alkyl group of 8-36 carbons and has a molecular weight between 150 to 1000 Daltons independent of the carrier and protective side chain weights.

10. The composition of claim 8, wherein the pharmaceutically acceptable excipient is selected from a starch, a sugar, a sugar alcohol, a salt, an amino acid, water, a buffer, a an antioxidant, a preserving agent, a polyol, an antiadhesive, a stabilizer, or a combination thereof.

11. The composition of claim 8, wherein the pharmaceutically acceptable excipient is one or more of an excipient selected from water, a buffer, a preserving agent, and a stabilizer.

12. The composition of claim 8, wherein the pharmaceutically acceptable excipient consists of a buffer, a preserving agent, and a stabilizer.

13. The composition of claim 8, wherein the load molecule is further dissociably linked to the orienting molecule.

14. The composition of claim 8, wherein the load molecule is a therapeutic agent selected from the group consisting of glucagon-like-peptide, exenatide, Gastric inhibitory polypeptide (GIP), Epidermal Growth Factor (EGF) receptor ligand, Transforming Growth Factor alpha (TGF-alpha), Betacellulin, Gastrin/Cholecystokinin receptor ligand, interferon, interleukin, tumor necrosis factor, insulin, insulin-like growth factor, growth hormone, nerve growth factor, brain-derived neurotrophic factor, endostatin, angiostatin, thrombospondin, blood clotting factor VII, blood clotting factor VIII, granulocyte-macrophage colony-stimulating factor (GM-CSF), granulocyte colony-stimulating factor (G-CSF), thrombopoietin, calcitonin, parathyroid hormone (PTH), erythropoietin, vasopressin, terlipressin, atrial natriuretic factor, somatostatin, adrenocorticotropin, gonadotropin releasing hormone, oxytocin, leutinizing-hormone-releasing-hormone, follicle stimulating hormone, vasopressin, terlipressin, desmopressin, vasoactive intestinal peptide (VIP), anti-bacterial agents, anti-fungal agents, anti-viral agents, doxorubicin, auristatin, and vitamins.

15. The composition of claim 8, wherein the load molecule is glucagon-like-peptide, Epidermal Growth Factor (EGF) receptor ligand, Transforming Growth Factor alpha (TGF-alpha), Betacellulin, Gastrin/Cholecystokinin receptor ligand, vasopressin, terlipressin, or atrial natriuretic factor.

16. The composition of claim 8, wherein the targeting molecule, when present, is selected from the group consisting of monocyte chemotactic protein 1, N-formyl-methionyl-leucyl-phenylalanine, granulocyte-macrophage colony-stimulating factor (GM-CSF), colony stimulating factor-1, granulocyte-macrophage colony-stimulating factor (GM-CSF) receptors, granulocyte-macrophage colony-stimulating factor (GM-CSF) antibodies, colony stimulating factor-1 receptors, colony stimulating factor-1 antibodies, platelet factor 4; TGF-fl growth factor, VEGF growth factor, E-selectin, VCAM-1 adhesive cell-surface glycoprotein, VCAM1fl adhesive cell-surface glycoprotein, 11C-deoxy-D-glucose, C1 component of vascular inflammatory response, C1q component of vascular inflammatory response, C1r component of vascular inflammatory response, C1s component of vascular inflammatory response, C2 component of vascular inflammatory response, C3 component of vascular inflammatory response, C3a component of vascular inflammatory response, C3b component of vascular inflammatory response, C4 component of vascular inflammatory response, C4C2 component of vascular inflammatory response, C4C2C3b component of vascular inflammatory response, C5a component of vascular inflammatory response, C5b component of vascular inflammatory response, C5a component of vascular inflammatory response, interleukin 1, interleukin 10, interleukin 2, interleukin 3, interleukin 6, interleukin 7, interleukin 8, interferon α, interferon γ, tumor necrosis factor TNF-α, polyethylene glycol coated liposomes, cholesterol, esters of cholesterol, LDL lipoprotein, HDL lipoprotein, and oxidized LDL lipoprotein.

17. A composition, consisting of:
(i) a polymeric carrier;
(ii) a plurality of first hydrophobic groups, wherein each first hydrophobic group of the plurality of first hydrophobic groups is covalently linked to the carrier, is capable of binding a load molecule, comprises an alkyl group of 8-36 carbons, and has a molecular weight between 150 to 1000 Daltons independent of the carrier weight;
(iii) a plurality of first protective side chains, wherein each first protective side chain is covalently linked to the carrier and has a molecular weight between and 20,000 Daltons independent of the carrier weight, and wherein each first protective side chain is polyethylene glycol, polypropylene glycol, a co-polymer of polyethylene glycol and polypropylene glycol, or an alkoxy derivative thereof;
(iv) optionally a plurality of second hydrophobic groups, wherein each second hydrophobic group is covalently linked at a first end to the carrier, and is linked at a second end to a second protective side chain having a molecular weight between 400 and 20,000 Daltons independent of the carrier weight,
wherein each second hydrophobic group is capable of binding a load molecule, has a molecular weight of less than 1,000 Daltons independent of the carrier weight, and wherein each second protective side chain is polyethylene glycol, polypropylene glycol, a co-polymer of polyethylene glycol and polypropylene glycol, or an alkoxy derivative thereof;
(v) a load molecule dissociably linked to the hydrophobic groups;
(vi) a targeting molecule covalently linked to the first protective side chains; and
(vii) a pharmaceutically acceptable excipient;
wherein a weight ratio of total protective side chains to total hydrophobic groups is more than 17:1 and the composition is soluble in aqueous buffer.

18. The composition of claim 17, wherein each second hydrophobic group, when present, comprises an alkyl group of 8-36 carbons and has a molecular weight between 150 to 1000 Daltons independent of the carrier and protective side chain weights.

19. The composition of claim 17, wherein the pharmaceutically acceptable excipient is selected from a starch, a sugar, a sugar alcohol, a salt, an amino acid, water, a buffer, a an antioxidant, a preserving agent, a polyol, an antiadhesive, a stabilizer, or a combination thereof.

20. The composition of claim 17, wherein the pharmaceutically acceptable excipient is one or more of an excipient selected from water, a buffer, a preserving agent, and a stabilizer.

21. The composition of claim 17, wherein the pharmaceutically acceptable excipient consists of a buffer, a preserving agent, and a stabilizer.

22. The composition of claim 17, wherein the load molecule is a therapeutic agent selected from the group consisting of glucagon-like-peptide, exenatide, Gastric inhibitory polypeptide (GIP), Epidermal Growth Factor (EGF) receptor ligand, Transforming Growth Factor alpha (TGF-alpha), Betacellulin, Gastrin/Cholecystokinin receptor ligand, interferon, interleukin, tumor necrosis factor, insulin, insulin-like growth factor, growth hormone, nerve growth factor, brain-derived neurotrophic factor, endostatin, angiostatin, thrombospondin, blood clotting factor VII, blood clotting factor VIII, granulocyte-macrophage colony-stimulating factor (GM-CSF), granulocyte colony-stimulating factor (G-CSF), thrombopoietin, calcitonin, parathyroid hormone (PTH), erythropoietin, vasopressin, terlipressin, atrial natriuretic factor, somatostatin, adrenocorticotropin, gonadotropin releasing hormone, oxytocin, leutinizing-hormone-releasing-hormone, follicle stimulating hormone, vasopressin, terlipressin, desmopressin, vasoactive intestinal peptide (VIP), anti-bacterial agents, anti-fungal agents, anti-viral agents, doxorubicin, auristatin, and vitamins.

23. The composition of claim 17, wherein the load molecule is glucagon-like-peptide, Epidermal Growth Factor (EGF) receptor ligand, Transforming Growth Factor alpha (TGF-alpha), Betacellulin, Gastrin/Cholecystokinin receptor ligand, vasopressin, terlipressin, or atrial natriuretic factor.

24. The composition of claim 17, wherein the targeting molecule is selected from the group consisting of monocyte chemotactic protein 1, N-formyl-methionyl-leucyl-phenylalanine, granulocyte-macrophage colony-stimulating factor (GM-CSF), colony stimulating factor-1, granulocyte-macrophage colony-stimulating factor (GM-CSF) receptors, granulocyte-macrophage colony-stimulating factor (GM-CSF) antibodies, colony stimulating factor-1 receptors, colony stimulating factor-1 antibodies, platelet factor 4; TGF-fl growth factor, VEGF growth factor, E-selectin, VCAM-1 adhesive cell-surface glycoprotein, VCAM1fl adhesive cell-surface glycoprotein, 11C-deoxy-D-glucose, C1 component of vascular inflammatory response, C1q component of vascular inflammatory response, C1r component of vascular inflammatory response, C1s component of vascular inflammatory response, C2 component of vascular inflammatory response, C3 component of vascular inflammatory response, C3a component of vascular inflammatory response, C3b component of vascular inflammatory response, C4 component of vascular inflammatory response, C4C2 component of vascular inflammatory response, C4C2C3b component of vascular inflammatory response, C5a component of vascular inflammatory response, C5b component of vascular inflammatory response, C5a component of vascular inflammatory response, interleukin 1, interleukin 10, interleukin 2, interleukin 3, interleukin 6, interleukin 7, interleukin 8, interferon α, interferon γ, tumor necrosis factor TNF-α, polyethylene glycol coated liposomes, cholesterol, esters of cholesterol, LDL lipoprotein, HDL lipoprotein, and oxidized LDL lipoprotein.

25. A composition, comprising:
(i) a polymeric carrier;
(ii) a plurality of first hydrophobic groups, wherein each first hydrophobic group of the plurality of first hydrophobic groups is covalently linked at a first end to the carrier, is capable of binding a load molecule, comprises an alkyl group of 8-36 carbons, and has a molecular weight between 150 to 1000 Daltons independent of the carrier weight;
(iii) a plurality of first protective side chains, wherein each first protective side chain is covalently linked to a second end of the first hydrophobic group, and has a molecular weight between 400 and 20,000 Daltons independent of the carrier weight, and wherein each first protective side chain is polyethylene glycol, polypropylene glycol, a co-polymer of polyethylene glycol and polypropylene glycol, or an alkoxy derivative thereof;
(iv) optionally a plurality of second hydrophobic groups, wherein each second hydrophobic group is covalently linked to the carrier, is capable of binding a load molecule, and has a molecular weight of less than 1,000 Daltons independent of the carrier weight;
(v) optionally a plurality of second protective side chains, wherein each second protective side chain is covalently linked to the carrier and has a molecular weight between 400 and 20,000 Daltons independent of the carrier weight, and wherein each second protective side chain is polyethylene glycol, polypropylene glycol, a co-polymer of polyethylene glycol and polypropylene glycol, or an alkoxy derivative thereof;
(vi) a load molecule dissociably linked to the hydrophobic groups;
(vii) optionally an orienting molecule covalently linked to the carrier, wherein the orienting molecule is selected from the group consisting of sulfate, sulfonate, phosphate, phosphonate, bisphosphonate, lysine, and arginine;
(viii) optionally a targeting molecule covalently linked to the first protective side chains; and
(ix) a pharmaceutically acceptable excipient;
wherein the weight ratio of the total protective side chains to the total hydrophobic groups is more than 17:1 and the composition is soluble in aqueous buffer.

26. The composition of claim 25, wherein each second hydrophobic group comprises an alkyl group of 8-36 carbons and has a molecular weight between 150 to 1000 Daltons independent of the carrier and protective side chain weights.

27. The composition of claim 25, wherein the pharmaceutically acceptable excipient is selected from a starch, a sugar, a sugar alcohol, a salt, an amino acid, water, a buffer, a an antioxidant, a preserving agent, a polyol, an antiadhesive, a stabilizer, or a combination thereof.

28. The composition of claim 25, wherein the pharmaceutically acceptable excipient is one or more of an excipient selected from water, a buffer, a preserving agent, and a stabilizer.

29. The composition of claim 25, wherein the pharmaceutically acceptable excipient consists of a buffer, a preserving agent, and a stabilizer.

30. The composition of claim 25, wherein the load molecule is a therapeutic agent selected from the group consisting of glucagon-like-peptide, exenatide, Gastric inhibitory polypeptide (GIP), Epidermal Growth Factor (EGF) receptor ligand, Transforming Growth Factor alpha (TGF-alpha), Betacellulin, Gastrin/Cholecystokinin receptor ligand, interferon, interleukin, tumor necrosis factor, insulin, insulin-like growth factor, growth hormone, nerve growth factor, brain-derived neurotrophic factor, endostatin, angiostatin, thrombospondin, blood clotting factor VII, blood clotting factor VIII, granulocyte-macrophage colony-stimulating factor (GM-CSF), granulocyte colony-stimulating factor (G-CSF), thrombopoietin, calcitonin, parathyroid hormone (PTH), erythropoietin, vasopressin, terlipressin, atrial natriuretic factor, somatostatin, adrenocorticotropin, gonadotropin releasing hormone, oxytocin, leutinizing-hormone-releasing-hormone, follicle stimulating hormone, vasopressin, terlipressin, desmopressin, vasoactive intestinal peptide (VIP), anti-bacterial agents, anti-fungal agents, anti-viral agents, doxorubicin, auristatin, and vitamins.

31. The composition of claim 25, wherein the load molecule is glucagon-like-peptide, Epidermal Growth Factor (EGF) receptor ligand, Transforming Growth Factor alpha (TGF-alpha), Betacellulin, Gastrin/Cholecystokinin receptor ligand, vasopressin, terlipressin, or atrial natriuretic factor.

32. The composition of claim 25, wherein the targeting molecule, when present, is selected from the group consisting of monocyte chemotactic protein 1, N-formyl-methionyl-leucyl-phenylalanine, granulocyte-macrophage colony-stimulating factor (GM-CSF), colony stimulating factor-1, granulocyte-macrophage colony-stimulating factor (GM-CSF) receptors, granulocyte-macrophage colony-stimulating factor (GM-CSF) antibodies, colony stimulating factor-1 receptors, colony stimulating factor-1 antibodies, platelet factor 4; TGF-fl growth factor, VEGF growth factor, E-selectin, VCAM-1 adhesive cell-surface glycoprotein, VCAM1fl adhesive cell-surface glycoprotein, 11C-deoxy-D-glucose, C1 component of vascular inflammatory response, C1q component of vascular inflammatory response, C1r component of vascular inflammatory response, C1s component of vascular inflammatory response, C2 component of vascular inflammatory response, C3 component of vascular inflammatory response, C3a component of vascular inflammatory response, C3b component of vascular inflammatory response, C4 component of vascular inflammatory response, C4C2 component of vascular inflammatory response, C4C2C3b component of vascular inflammatory response, C5a component of vascular inflammatory response, C5b component of vascular inflammatory response, C5a component of vascular inflammatory response, interleukin 1, interleukin 10, interleukin 2, interleukin 3, interleukin 6, interleukin 7, interleukin 8, interferon α, interferon γ, tumor necrosis factor TNF-α, polyethylene glycol coated liposomes, cholesterol, esters of cholesterol, LDL lipoprotein, HDL lipoprotein, and oxidized LDL lipoprotein.

* * * * *

UNITED STATES PATENT AND TRADEMARK OFFICE
CERTIFICATE OF CORRECTION

PATENT NO. : 10,507,248 B2  
APPLICATION NO. : 15/672802  
DATED : December 17, 2019  
INVENTOR(S) : G. Castillo et al.

Page 1 of 1

It is certified that error appears in the above-identified patent and that said Letters Patent is hereby corrected as shown below:

In the Claims

| Column | Line | |
|---|---|---|
| 79 | 29 | Claim 8 change "between about 400" to -- between 400 -- |
| 81 | 15 | Claim 17 change "between and" to -- between 400 and -- |

Signed and Sealed this  
Eighth Day of December, 2020

Andrei Iancu  
*Director of the United States Patent and Trademark Office*